(12) United States Patent
Okajima et al.

(10) Patent No.: US 8,299,459 B2
(45) Date of Patent: Oct. 30, 2012

(54) DIINDENOPICENE COMPOUND AND ORGANIC LIGHT EMITTING DEVICE USING THE SAME

(75) Inventors: Maki Okajima, Kawasaki (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/063,811

(22) PCT Filed: Sep. 28, 2010

(86) PCT No.: PCT/JP2010/067326
§ 371 (c)(1),
(2), (4) Date: Mar. 14, 2011

(87) PCT Pub. No.: WO2011/040631
PCT Pub. Date: Apr. 7, 2011

(65) Prior Publication Data
US 2011/0204349 A1    Aug. 25, 2011

(30) Foreign Application Priority Data
Oct. 1, 2009  (JP) ................................. 2009-229314

(51) Int. Cl.
*H01L 29/08* (2006.01)
(52) U.S. Cl. ........................................... 257/40; 438/99
(58) Field of Classification Search ............. 257/40; 438/99
See application file for complete search history.

(56) References Cited

U.S. PATENT DOCUMENTS
7,709,832 B2    5/2010 Negishi et al.
(Continued)

FOREIGN PATENT DOCUMENTS
JP    09-241629 A    9/1997
(Continued)

OTHER PUBLICATIONS

Kajigaeshi et al., "Selective Preparation of Fluorene Derivatives Using the *t*-Butyl Function as a Positional Protective Group", Bull. Chem. Soc. Jpn., vol. 59, pp. 97-103 (1986), January.
(Continued)

*Primary Examiner* — Marcos D. Pizarro
*Assistant Examiner* — Bilkis Jahan
(74) *Attorney, Agent, or Firm* — Fitzpatrick, Cella, Harper & Scinto

(57) ABSTRACT

The present invention provides an organic light emitting device which shows a blue light emission hue of remarkably good color purity and has a high-efficiency and high-luminance optical output. An organic light emitting device including an anode 2, a cathode 4 and an organic compound layer sandwiched between the anode 2 and the cathode 4, wherein at least one diindenopicene compound represented by general formula [1] described below is contained in the organic compound layer:

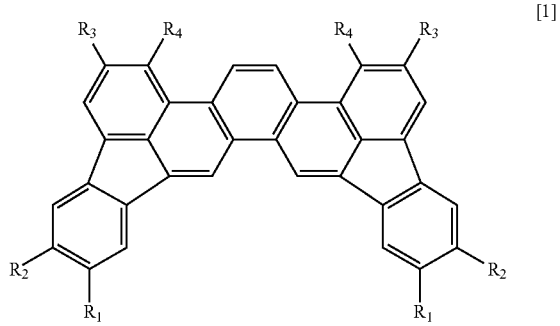

6 Claims, 2 Drawing Sheets

U.S. PATENT DOCUMENTS

| | | |
|---|---|---|
| 7,883,388 B2 * | 2/2011 | Lee et al. .................. 445/24 |
| 7,932,592 B2 | 4/2011 | Saitoh et al. |
| 7,939,185 B2 * | 5/2011 | Yamada et al. ............. 428/690 |
| 2009/0033210 A1 | 2/2009 | Saitoh et al. |
| 2009/0066227 A1 | 3/2009 | Okinaka et al. ............. 313/504 |
| 2009/0096368 A1 | 4/2009 | Kamatani et al. |
| 2009/0102371 A1 | 4/2009 | Hashimoto et al. |
| 2009/0189518 A1 | 7/2009 | Yamada et al. ............. 313/504 |
| 2010/0019661 A1 | 1/2010 | Yamada et al. |
| 2010/0032658 A1 | 2/2010 | Lee et al. ................... 257/40 |
| 2010/0127618 A1 * | 5/2010 | Ohrui et al. ................ 313/504 |
| 2010/0237328 A1 | 9/2010 | Horiuchi et al. |
| 2011/0024737 A1 | 2/2011 | Horiuchi et al. |
| 2011/0049479 A1 | 3/2011 | Yamada et al. |

FOREIGN PATENT DOCUMENTS

| | | |
|---|---|---|
| JP | 2002-069044 A | 3/2002 |
| JP | 2007-318063 A | 12/2007 |
| JP | 2008-290999 A | 12/2008 |
| JP | 2009-001499 A | 1/2009 |
| JP | 2009-126848 A | 6/2009 |
| JP | 2009-149612 A | 7/2009 |
| JP | 2010-018574 A | 1/2010 |
| JP | 2010-059147 A | 3/2010 |
| JP | 2010-143879 A | 7/2010 |
| JP | 2010-143880 A | 7/2010 |
| WO | 2007/072741 A1 | 6/2007 |
| WO | 2010/008034 | 1/2010 |
| WO | 2010/071223 | 6/2010 |
| WO | 2010/071224 | 6/2010 |

OTHER PUBLICATIONS

Machine translation of JP 2008-290999.
Machine translation of JP 2009-001499.
Machine translation of JP 2009-149612.
Machine translation of JP 2002-069044.
Machine translation of JP 09-241629.

* cited by examiner

DIINDENOPICENE COMPOUND AND ORGANIC LIGHT EMITTING DEVICE USING THE SAME

TECHNICAL FIELD

The present invention relates to a diindenopicene compound and an organic light emitting device using the diindenopicene compound.

BACKGROUND ART

An organic light emitting device is a device in which a thin film containing a fluorescent or phosphorescent organic compound is sandwiched in between a pair of electrodes. An exciton of the fluorescent or phosphorescent organic compound is generated by injecting electrons and holes (positive holes) from each of the electrodes, and when the exciton returns to its ground state, the organic light emitting device emits light. Recent progress in technology of organic light emitting devices is remarkable. As characteristics of organic light emitting devices, for example, high luminance by application of low voltage, versatility of light emission wavelengths, high-speed responsibility, slimming down of a light emitting device, and weight reduction can be achieved. This suggests that organic light emitting devices have the potential for being adaptable to a wide variety of applications.

However, in light of commercial application and practical use to a full-color display and the like, it is essential for organic light emitting devices to improve their light emitting efficiency, color purity and operating life of the devices. Especially for blue-color light emitting devices, the development of a material with high color purity and high light emitting efficiency is desired; however, there are a few materials that can satisfy the requirements because of difficulties of the development.

Meanwhile, with a view to achieving high light efficiency and improving the stability of an organic light emitting device which emits blue light, a variety of materials and device configurations have been proposed. For example, PTL 1 proposes a host material having a pyrene skeleton and a light emitting dopant having a fluoranthene skeleton. Here, a material having a pyrene skeleton is excellent in electron transportability, whereas a light emitting dopant having a fluoranthene skeleton functions as an electron trap. Thus, with use of these materials, the carrier off-balance and an eccentric distribution of light emission areas can be eliminated, and the light emitting efficiency and continuous driving of a light emitting device are improved.

As other examples of a condensed hydrocarbon having a fluoranthene skeleton in its molecule, as typified by PTL 1, for example, the compounds disclosed in PLTS 2 and 3 are exemplified. Although most of these compounds are improved to have high light emitting efficiency and high stability due to their possession of the electron trapping function, they cannot sufficiently satisfy the color purity required for blue color light emitting materials. Accordingly, further improvements are desired to provide a material satisfying the requirements.

CITATION LIST

Patent Literature

PTL 1: Japanese Patent Application Laid-Open No. 2007-318063

PTL 2: Japanese Patent Application Laid-Open No. 2002-69044

PTL 3: Japanese Patent Application Laid-Open No. 09-241629

Non Patent Literature

NPL 1: Bulletin of Chemical Society of Japan, Vol. 59, 97-103 (1986)

SUMMARY OF INVENTION

The present invention has been made to solve the above-mentioned conventional problems, and an object of the present invention is to provide an organic light emitting device which shows a blue light emission hue of remarkably excellent color purity and has a high-efficiency and high-luminance optical output.

SOLUTION TO PROBLEM

Therefore, the present invention provides a diindenopicene compound represented by general formula [1] described below:

Formula 1

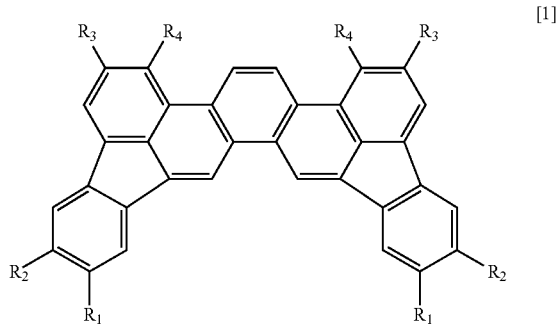

[1]

wherein $R_1$ to $R_4$ are each a hydrogen atom, an alkyl group, an unsubstituted phenyl group or a phenyl group substituted by an alkyl group, provided that a combination of substituents represented by $R_1$ to $R_4$ is any of the following (1) to (4):

(1) $R_1$, $R_2$, $R_3$ and $R_4$ are all hydrogen atoms;

(2) $R_1$ and $R_4$ are each an alkyl group, an unsubstituted phenyl group or a phenyl group substituted by an alkyl group, and $R_2$ and $R_3$ are each a hydrogen atom, wherein $R_1$ and $R_4$ may be each identical or different;

(3) $R_2$ and $R_3$ are each an alkyl group, an unsubstituted phenyl group or a phenyl group substituted by an alkyl group, and $R_1$ and $R_4$ are each a hydrogen atom, wherein $R_2$ and $R_3$ may be each identical or different;

(4) $R_1$ is an alkyl group, an unsubstituted phenyl group or a phenyl group substituted by an alkyl group, $R_2$ and $R_4$ are each a hydrogen atom, and $R_3$ is a hydrogen atom, an unsubstituted phenyl group or a phenyl group substituted by an alkyl group, wherein when both $R_1$ and $R_3$ are an unsubstituted phenyl group or a phenyl group substituted by an alkyl group, $R_1$ and $R_3$ may be each identical or different).

Further features of the present invention will become apparent from the following description of exemplary embodiments with reference to the attached drawings.

DESCRIPTION OF EMBODIMENTS

Figure 1A:
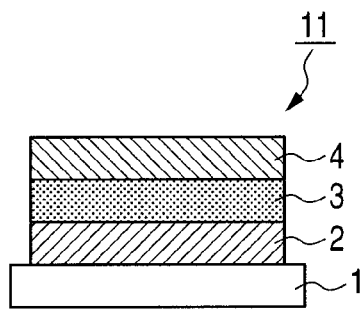
FIGS. 1A, 1B, 1C, 1D and 1E are a cross-sectional schematic diagram illustrating an exemplary embodiment in an organic light emitting device according to the present invention.

Hereinafter, the present invention will be described in detail.

First, a diindenopicene compound of the present invention will be described.

The diindenopicene compound of the present invention is a compound represented by general formula [1] described below:

Formula 2

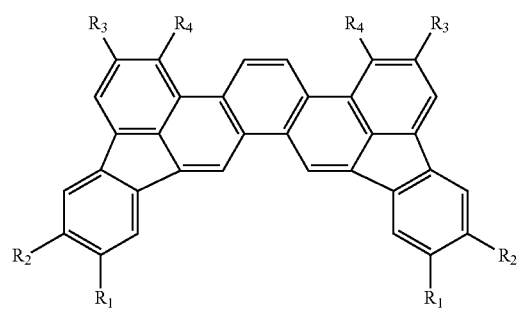

[1]

wherein $R_1$ to $R_4$ are each a hydrogen atom, an alkyl group, an unsubstituted phenyl group or a phenyl group substituted by an alkyl group.

Examples of the alkyl group represented by $R_1$ to $R_4$ include a methyl group, an ethyl group, an n-propyl group, an iso-propyl group, an n-butyl group, an iso-butyl group, a sec-butyl group, a tert-butyl group, an n-pentyl group, an iso-pentyl group, a neo-pentyl group, a tert-pentyl group, a hexyl group, a heptyl group, and an octyl group.

When $R_1$ to $R_4$ are a phenyl group, the phenyl group may be further substituted by an alkyl group. Examples of the alkyl group by which the phenyl group may be substituted include a methyl group, an ethyl group, an n-propyl group, an iso-propyl group, an n-butyl group, an iso-butyl group, a sec-butyl group, a tert-butyl group, an n-pentyl group, an iso-pentyl group, a neo-pentyl group, a tert-pentyl group, a hexyl group, a heptyl group, and an octyl group. Note that the above-mentioned alkyl group may be substituted in a plurality of sites of the phenyl group. In addition, when the alkyl group may be substituted in a plurality of sites of the phenyl group, the alkyl group to be substituted may be identical or different.

Provided that a combination of substituents represented by $R_1$ to $R_4$ is any of the following (1) to (4):

(1) $R_1$, $R_2$, $R_3$ and $R_4$ are all hydrogen atoms;

(2) $R_1$ and $R_4$ are each an alkyl group, an unsubstituted phenyl group or a phenyl group substituted by an alkyl group, and $R_2$ and $R_3$ are each a hydrogen atom, wherein $R_1$ and $R_4$ may be each identical or different;

(3) $R_2$ and $R_3$ are each an alkyl group, an unsubstituted phenyl group or a phenyl group substituted by an alkyl group, and $R_1$ and $R_4$ are each a hydrogen atom, wherein $R_2$ and $R_3$ may be each identical or different;

(4) $R_1$ is an alkyl group, an unsubstituted phenyl group or a phenyl group substituted by an alkyl group, $R_2$ and $R_4$ are each a hydrogen atom, and $R_3$ is a hydrogen atom, an unsubstituted phenyl group or a phenyl group substituted by an alkyl group, wherein when both $R_1$ and $R_3$ are an unsubstituted phenyl group or a phenyl group substituted by an alkyl group, $R_1$ and $R_3$ may be each identical or different.

Next, basic synthesis methods for the diindenopicene compound of the present invention will be described.

The diindenopicene compound of the present invention is synthesized according to the following synthesis method/synthesis scheme.

Specifically, when the combination of substituents represented by $R_1$ to $R_4$ is (1) described above, the diindenopicene compound can be synthesized by using 1,4-bromo-2,3-dimethylbenzen and fluorene as starting materials. The synthesis method will be described in detail in the paragraphs of Examples.

When the combination of substituents represented by $R_1$ to $R_4$ is (2) or (3), the diindenopicene compound can be synthesized according to the following synthesis scheme.

Formula 3

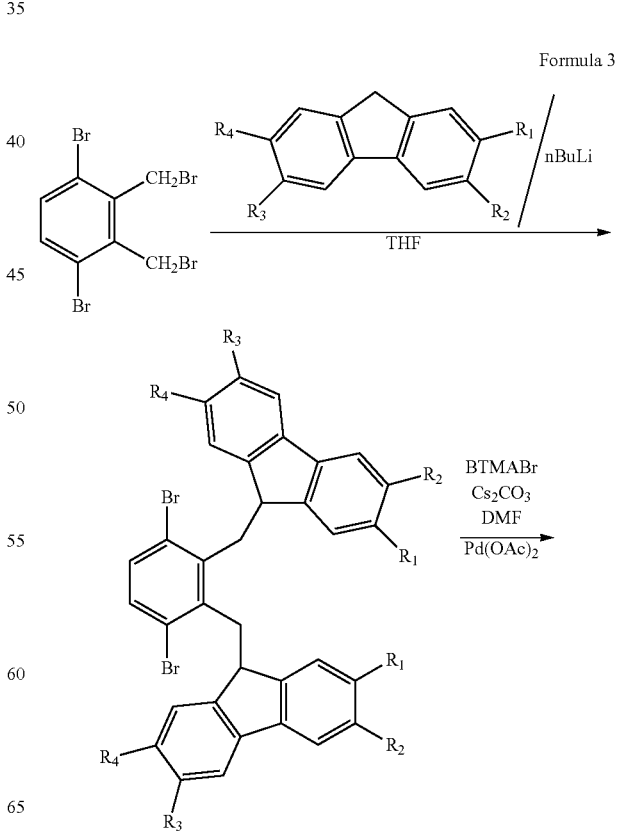

-continued

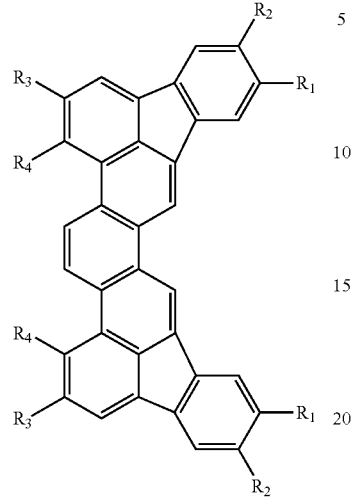

In the above synthesis scheme, $R_1$ to $R_4$ are identical to $R_1$ to $R_4$ in general formula [1]. Here, specific examples of the combination of fluorene derivatives serving as a starting material and exemplary compounds to be synthesized (the structural formulas thereof will be described later) are shown in the following Table 1.

TABLE 1

| Fluorene Derivative | Exemplary Compound |
|---|---|
| 2,7-dimethylfluorene | B-1 |
| 2-phenyl-7-methylfluorene | C-4 |
| 3,6-dimethylfluorene | D-1 |
| 3-(3,5-di-tert-butyl)phenyl-6-phenylfluorene | E-102 |
|  | E-103 |

When the combination of substituents represented by $R_1$ to $R_4$ is (4) and $R_3$ is a hydrogen atom, the diindenopicene compound can be synthesized according to the following synthesis scheme.

Formula 4

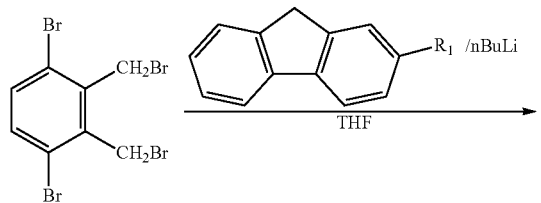

-continued

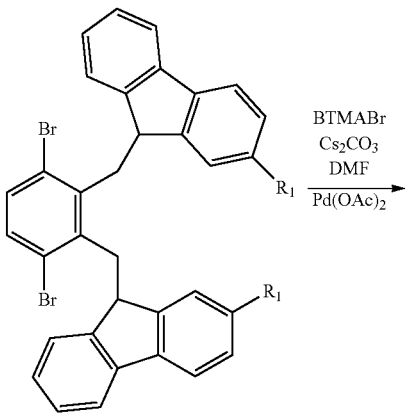

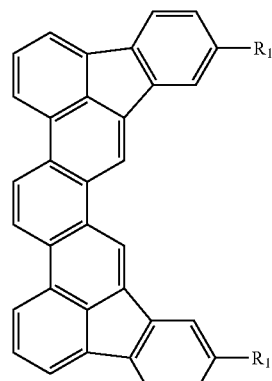

In the above synthesis scheme, $R_1$ is identical to $R_1$ in general formula [1]. Here, when the fluorene derivative serving as a starting material is 2-phenylfluorene, Exemplary Compound F-3 is synthesized. The structural formula of Exemplary Compound F-3 will be described later.

When the combination of substituents represented by $R_1$ to $R_4$ is (4) and $R_3$ is an unsubstituted phenyl group or a phenyl group substituted by an alkyl group, the diindenopicene compound can be synthesized according to the following synthesis scheme.

Formula 5

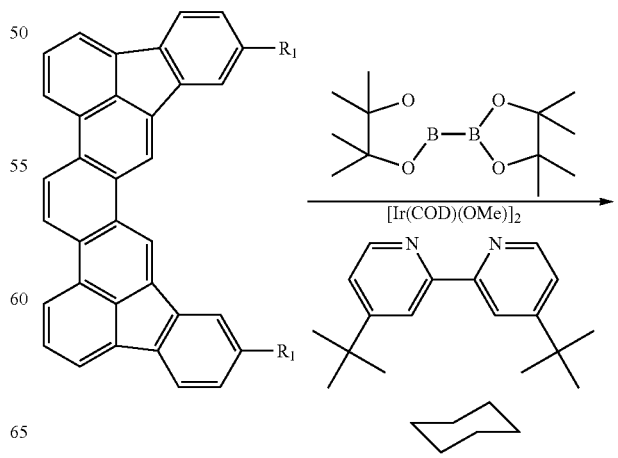

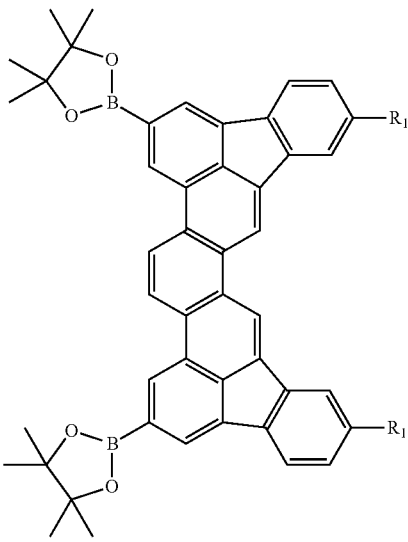

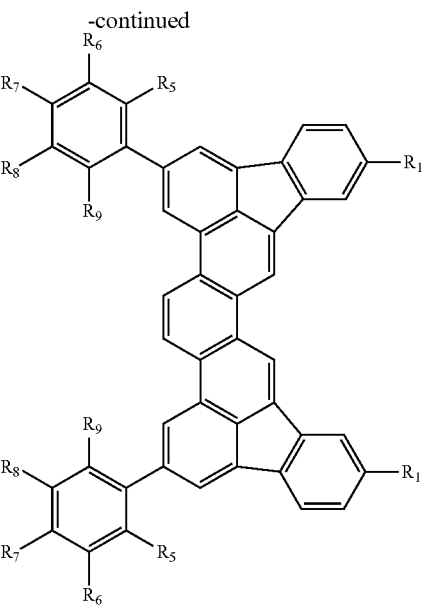

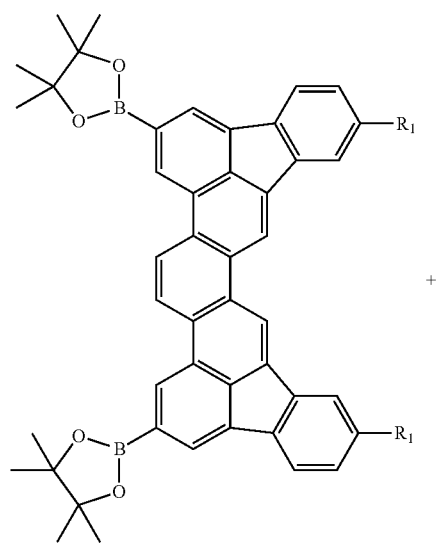

+

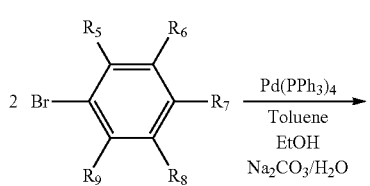

In the above synthesis scheme, $R_1$ is identical to $R_1$ in general formula [1]; and $R_5$ to $R_9$ are each a hydrogen atom or an alkyl group such as a methyl group, an ethyl group, an n-propyl group, an iso-propyl group, an n-butyl group, an iso-butyl group, a sec-butyl group, a tert-butyl group, an n-pentyl group, an iso-pentyl group, a neo-pentyl group, a tert-pentyl group, a hexyl group, a heptyl group, and an octyl group, and $R_5$ to $R_9$ may be identical or different. Here, when the fluorene derivative serving as a starting material is 2-(4-methyl)phenylfluorene and $R_5$ to $R_9$ are a hydrogen atom, Exemplary Compound G-2 is synthesized. The structural formula of Exemplary Compound G-2 will be described later.

Generally, as for a condensed polycyclic hydrocarbon compound having a fluoranthene skeleton, the lowest unoccupied molecular orbital (LUMO) can be established to be deeper (electron affinity becomes larger). For this reason, the condensed polycyclic hydrocarbon compound having a fluoranthene skeleton is excellent in electron injection property. Further, when the condensed polycyclic hydrocarbon compound having a fluoranthene skeleton is used as a guest (light emitting dopant) of a light emitting layer, in combination with a host material in which the lowest unoccupied molecular orbital (LUMO) is shallow (electron affinity is small), the guest functions as an electron trapping material. With this, the carrier off-balance and an eccentric distribution of light emission areas can be eliminated. As a result, the light emitting efficiency and the operating life of the device during continuous driving can be greatly improved.

The condensed polycyclic hydrocarbon compound having a fluoranthene skeleton has a tendency that the higher in the number of five-membered ring than the number of six-membered rings, the deeper the lowest unoccupied molecular orbital (LUMO) (the larger the electron affinity) becomes. That is, there is a tendency that the more the number of fluoranthene skeletons in its molecule, the deeper the lowest unoccupied molecular orbital (LUMO) (the larger the electron affinity) becomes. However, an increase in the number of fluoranthene skeletons in a molecule makes a reduction in energy gap of the molecule itself. As a result, the emission color has a longer wavelength, and the material becomes unsuitable as a blue light emitting material.

On the other hand, the diindenopicene compound of the present invention contains a picene skeleton which has a relatively wide energy gap in the basic skeleton. Further, the diindenopicene compound of the present invention can be considered, from a different point view, to have two fluoranthene skeletons in the molecule in a state where a picene skeleton and two benzene rings interfere with each other. Therefore, the diindenopicene compound of the present invention can emit blue light having remarkably excellent color purity, while maintaining the lowest unoccupied molecular orbital (LUMO) deeper (maintaining the electron affinity larger) in the molecules.

In the diindenopicene compound of the present invention, since the substituents introduced into $R_1$ to $R_4$ in general formula [1] are an alkyl group, an unsubstituted phenyl group or a phenyl group substituted by an alkyl group, the diindenopicene compound can emit blue light having remarkably excellent color purity, without being influenced by the substituents. Here, to allow the diindenopicene compound to emit blue light excellent in color purity and to minimize the influence of the substituents, it is desired to select such a substituent that the substituents introduced are easily positioned perpendicularly to the plane formed by a diindenopicene skeleton in general formula [1]. Here, it is more preferable that the substituent introduced in any of $R_1$ to $R_4$ in general formula [1] be a phenyl group substituted by an alkyl group at any of the 2-position and the 6-position, because the resulting diindenopicene compound can emit blue light having remarkably excellent color purity. It is particularly preferable that the substituent introduced in any of $R_1$ to $R_4$ in general formula [1] be a phenyl group substituted by an alkyl group at the 2-position and the 6-position, for example, 2-6-dimethylphenyl group, from the view point of emitting blue light excellent in color purity.

In general, to increase the light emitting efficiency of an organic light emitting device, the light emitting material itself desirably has a high light emission quantum yield. Here, the diindenopicene compound of the present invention has a high oscillator strength, as determined by a molecular orbital calculation, and thus a high light emission quantum yield can be expected. In addition, when substituents are introduced into $R_2$ and $R_3$ in general formula [1] in the diindenopicene compound of the present invention, the oscillator strength is further increased, and thus a higher light emission quantum yield can be obtained.

When a substituent is introduced into any of $R_1$ to $R_4$ in general formula [1], it is possible to reduce a decrease in light emitting efficiency caused by molecule association. Particularly when substituents are introduced thereinto according to the above-mentioned conditions (2), the substituents are to be introduced into the vicinity of the center of the diindenopicene skeleton which is a main skeleton, and thus the effect of reducing a decrease in light emitting efficiency caused by molecule association is increased. Further, a steric hindrance can be given to the molecule itself, depending on the type of the substituent to be introduced, and thus the decrease in light emitting efficiency caused by molecule association can be reduced. Here, when a phenyl group substituted by an alkyl group at any of the 2-position and the 6-position is introduced into any of $R_1$ to $R_4$, the introduced substituent is easily positioned perpendicularly to the plane formed by the diindenopicene skeleton. Due to the substituent effect, the diindenopicene compound of the present invention has an increased effect of reducing a decrease in light emitting efficiency caused by molecule association. It is particularly desired that any of $R_1$ to $R_4$ be a phenyl group substituted by an alkyl group at the 2-position and the 6-position, for example, a 2,6-dimethylphenyl group, from the viewpoint of reducing a decrease in light emitting efficiency caused by molecule association.

Note that when the diindenopicene compound of the present invention is used as a constituent material of a light emitting layer, it can be used for both of the host and guest materials. In particular, when the diindenopicene compound of the present invention is used as a host of a light emitting layer, preferably, any of $R_1$ to $R_4$ has a substituent (an alkyl group, an unsubstituted phenyl group or a phenyl group substituted by an alkyl group), from the viewpoint that a material having a high glass transition temperature is preferred.

Specific structural formulae of the diindenopicene compound of the present invention are described below, which are, however, described by way of typical examples only, and the present invention shall not be construed as being limited thereto.

Formula 6

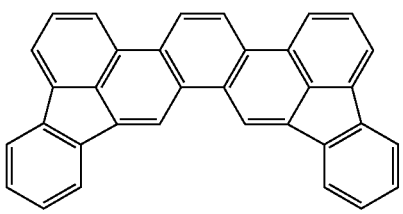

A-1

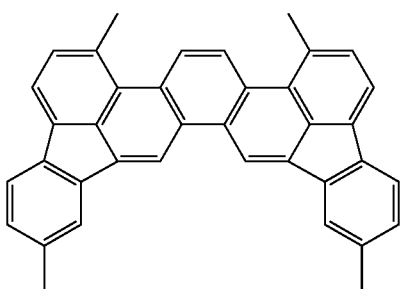

B-1

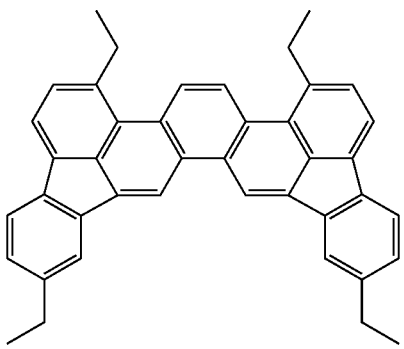

B-2

B-3
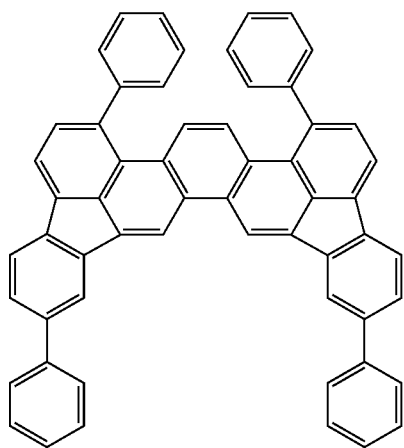
B-6
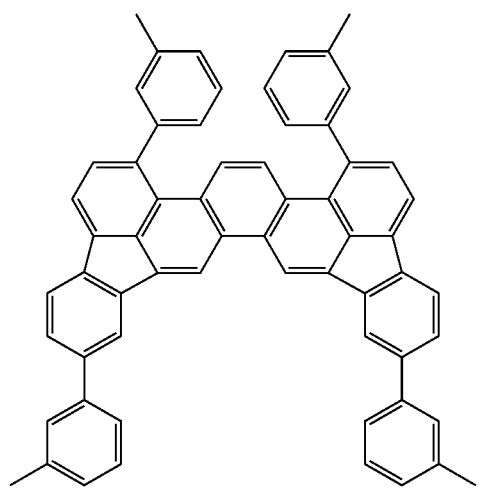
B-4
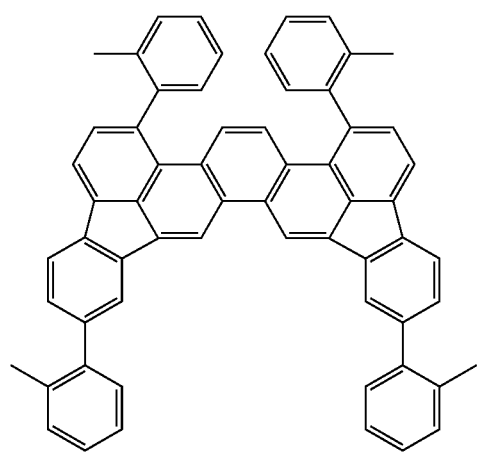
B-7
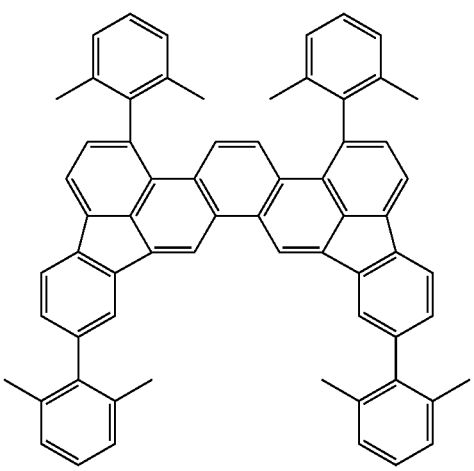
B-5
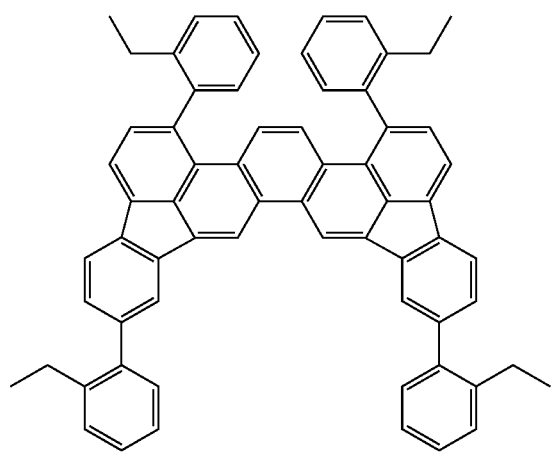
B-8
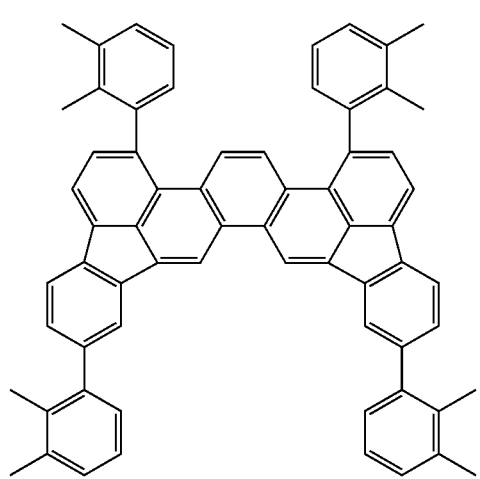

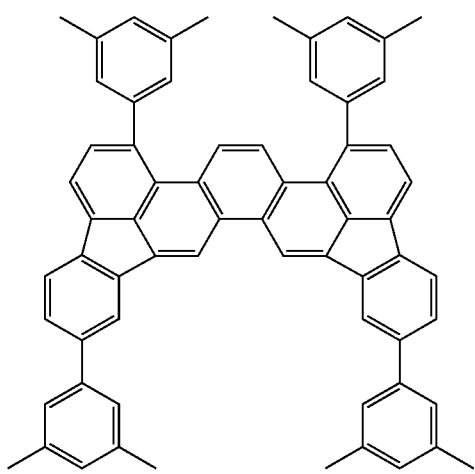
B-9
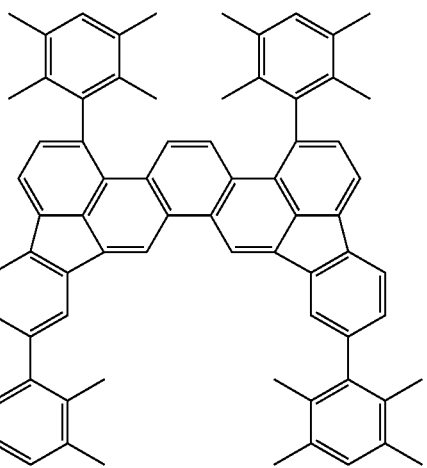
B-12
Formula 7
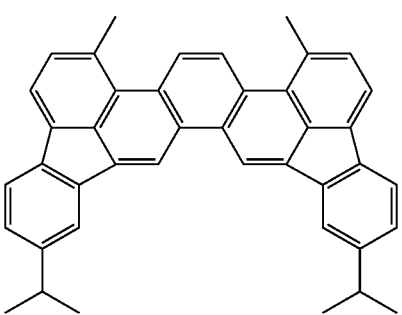
C-1
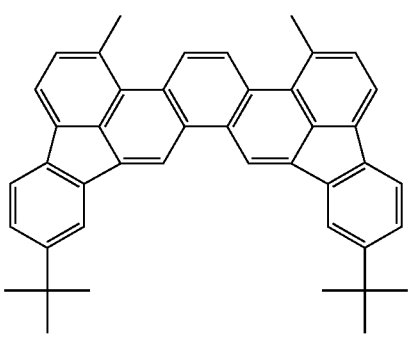
C-2
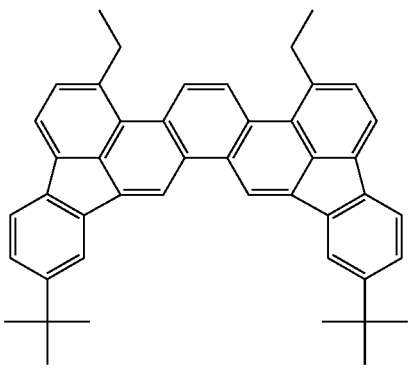
C-3

C-4
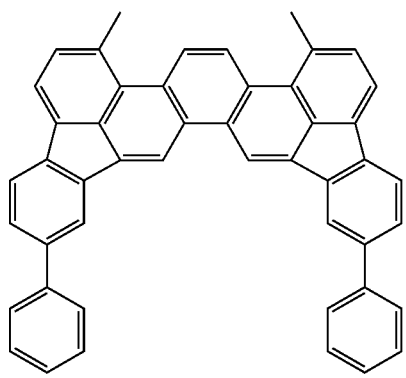
C-5
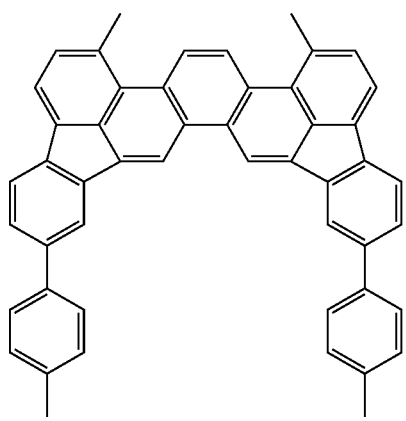
C-6
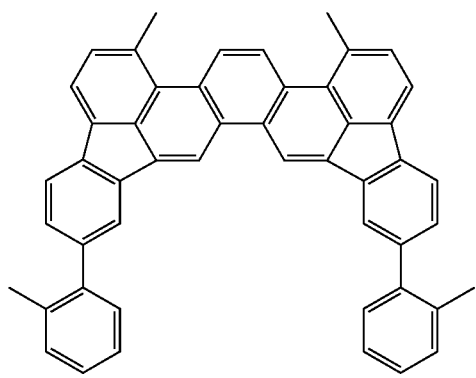
C-7
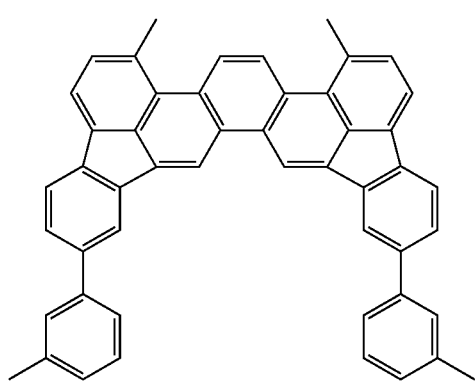
C-8
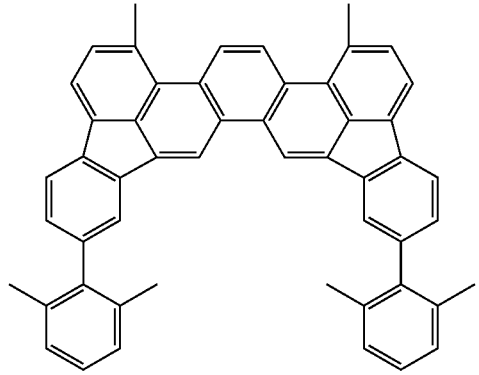
C-9
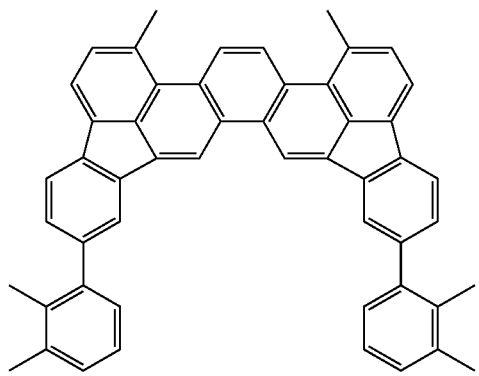
C-10
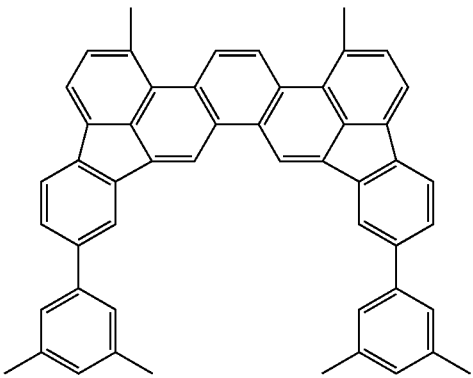
C-11
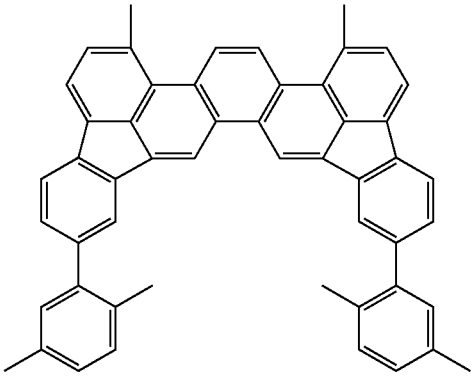

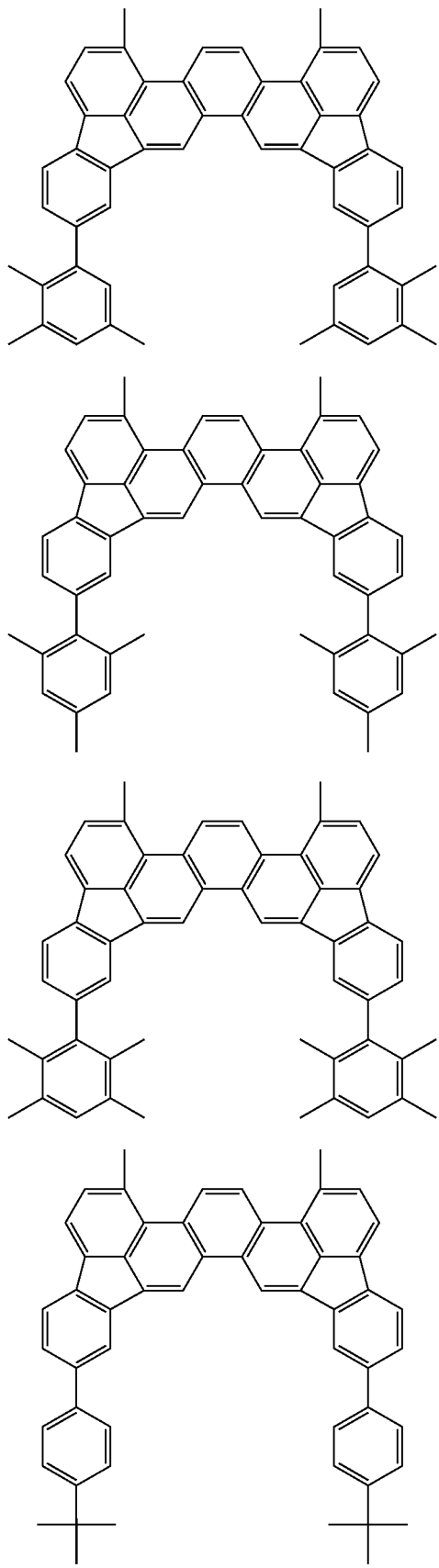
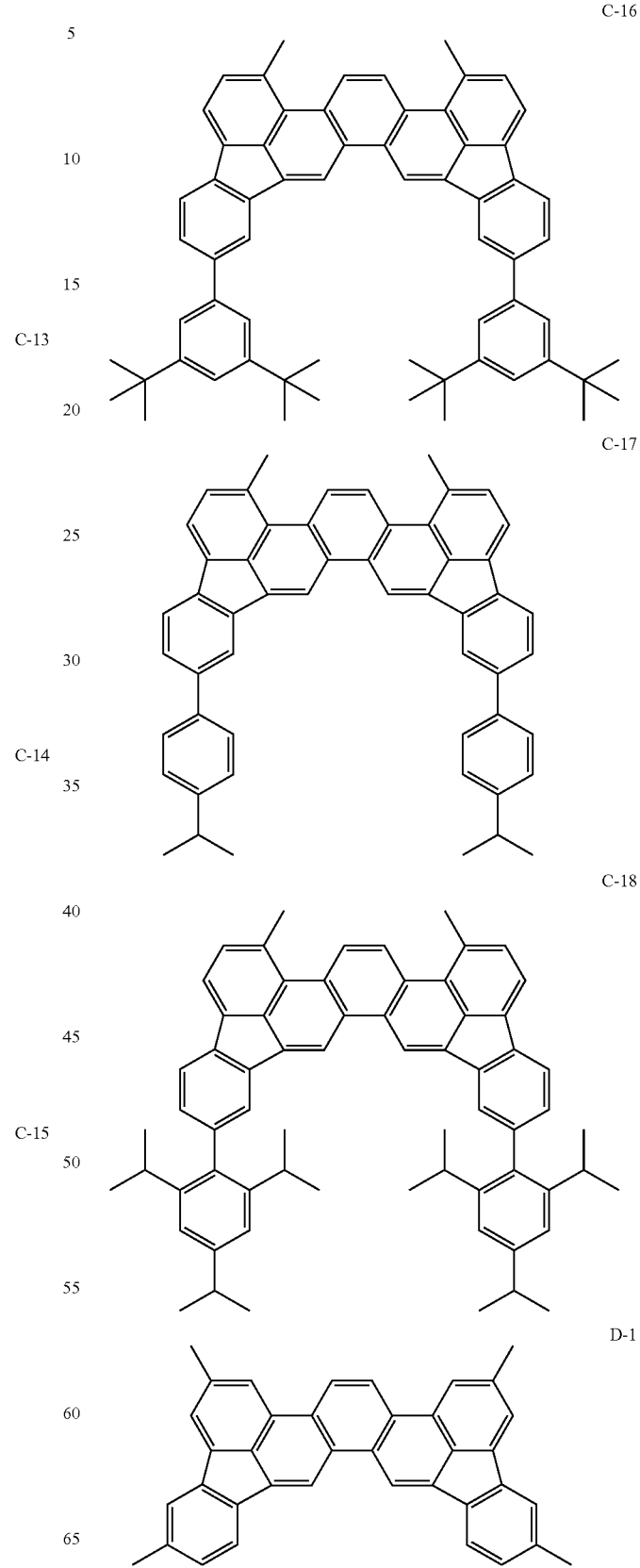

-continued
D-2
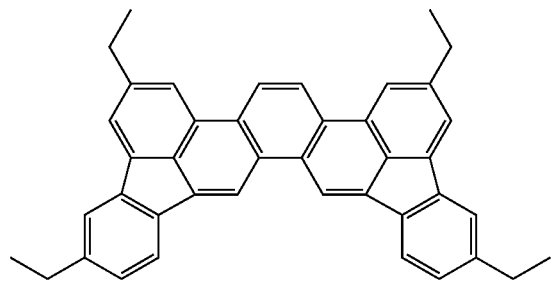
D-6
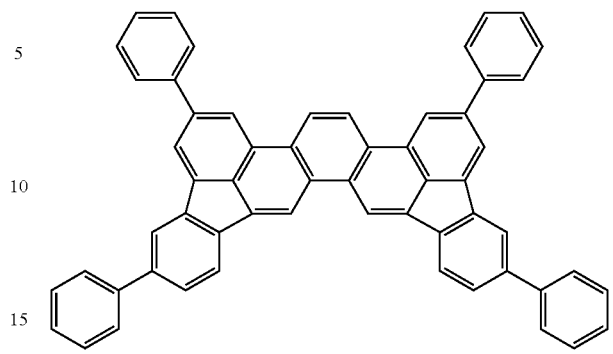
D-3
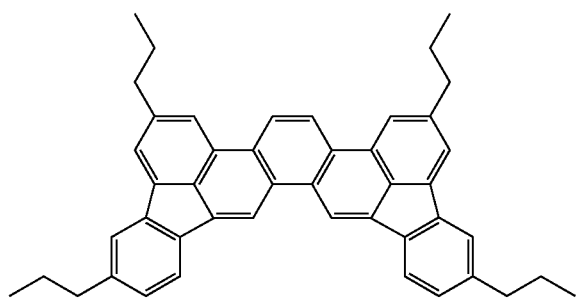
D-7
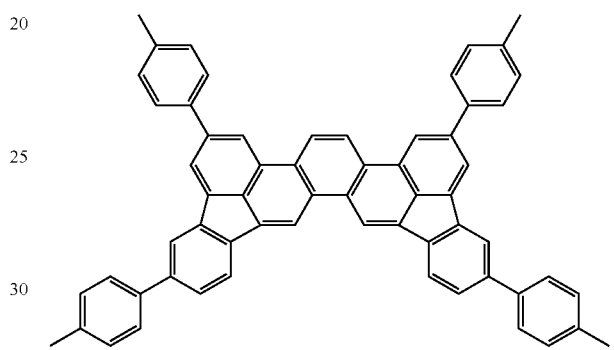
D-4
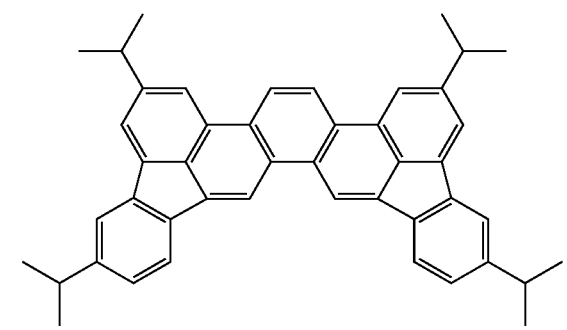
D-8
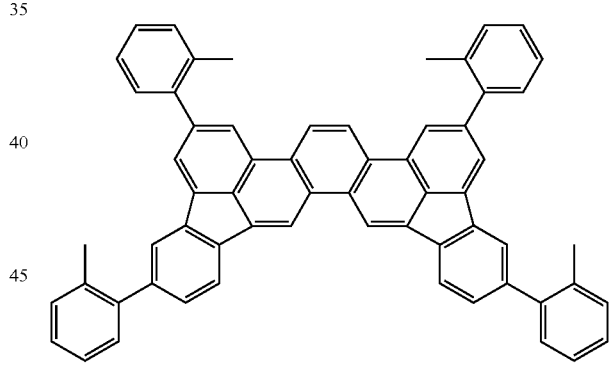
D-5
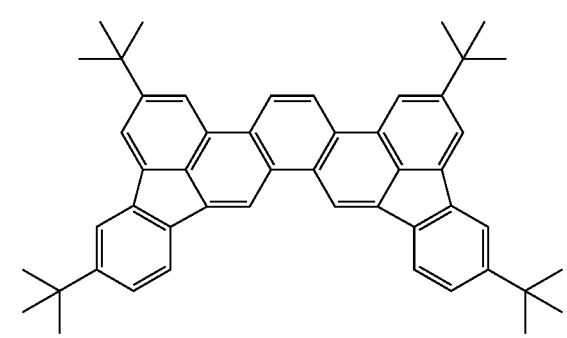
D-9
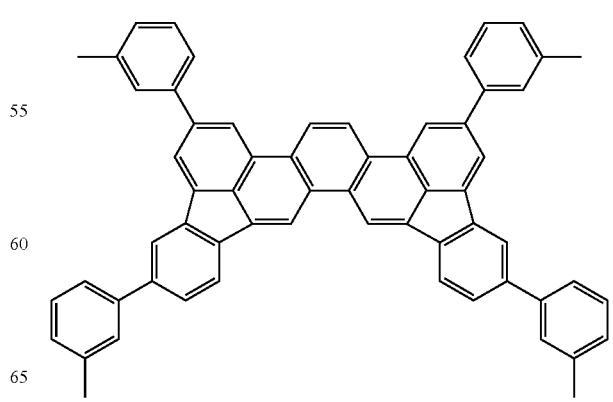

-continued
D-10
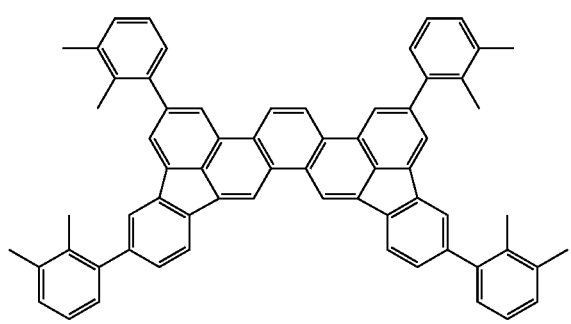
D-11
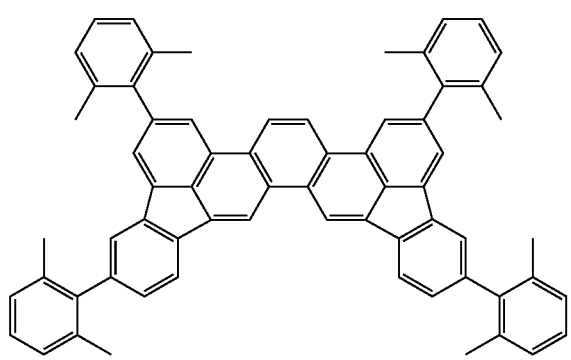
D-12
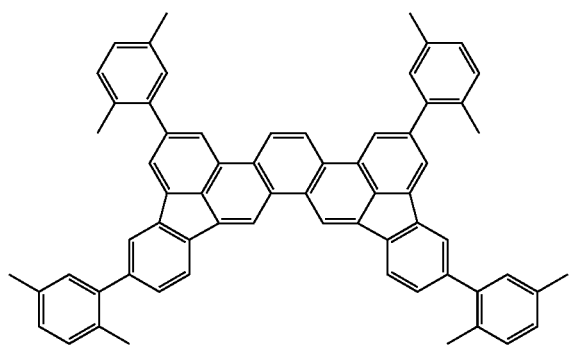
D-13
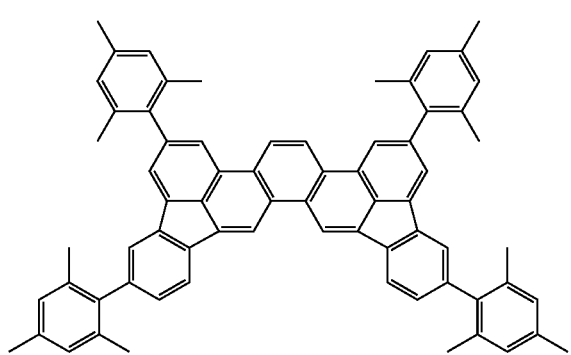
-continued
D-14
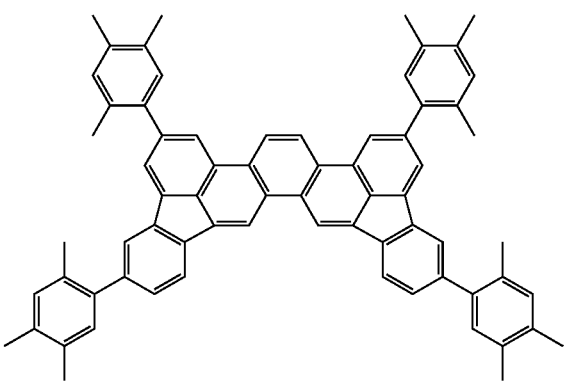
D-15
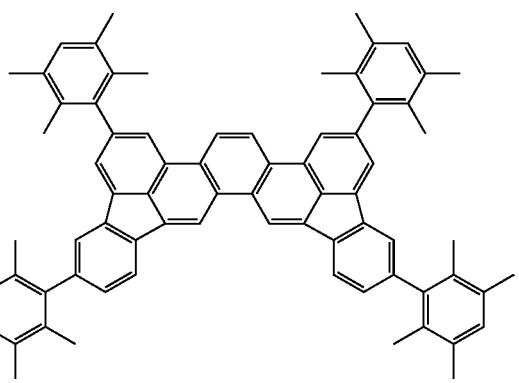
Formula 9
D-16
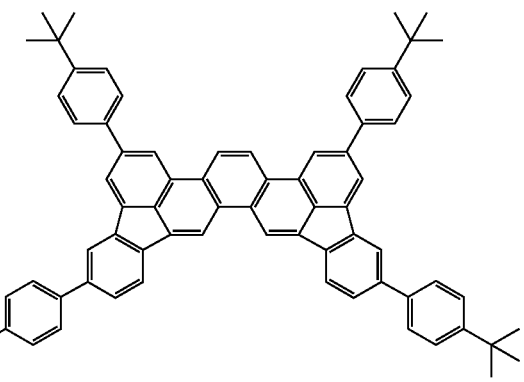
D-17
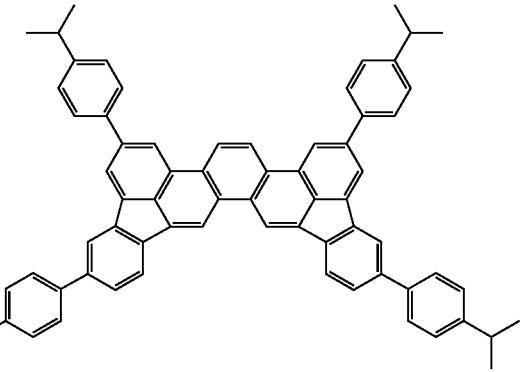

D-18
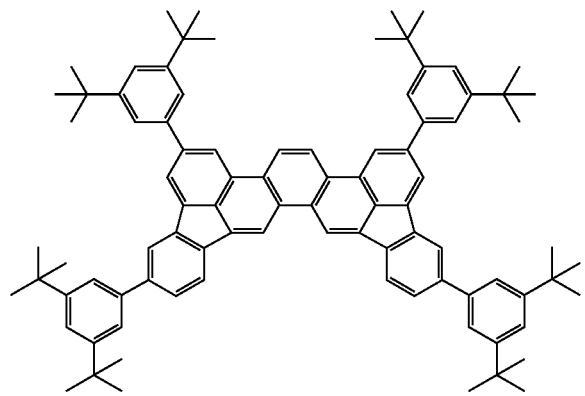
D-19
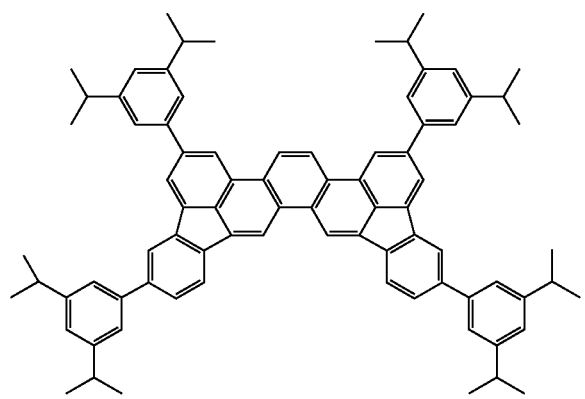
E-1
E-2
E-3
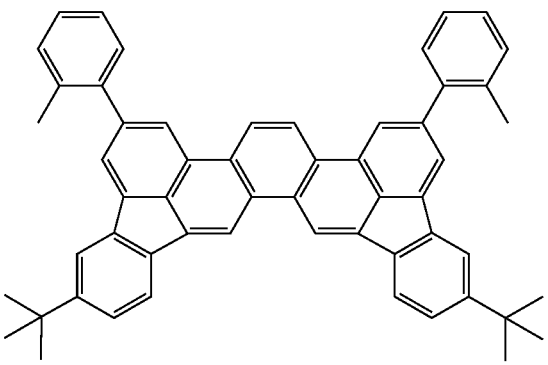
E-4
E-5
E-6
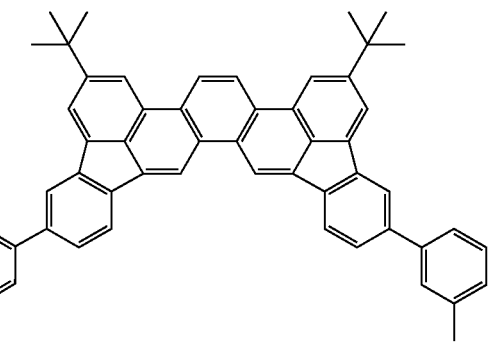

-continued
E-7
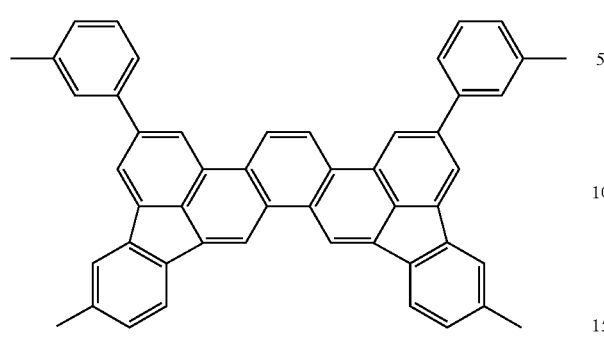
E-8
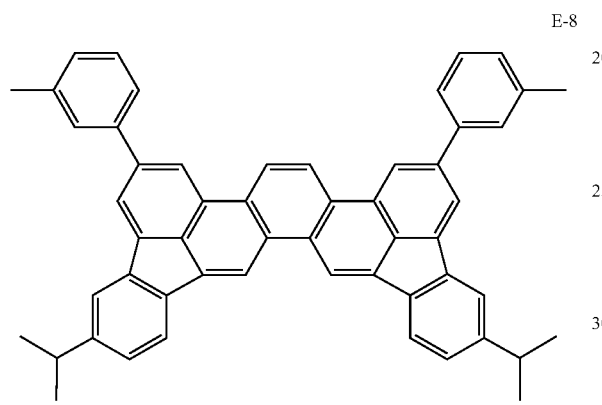
E-9
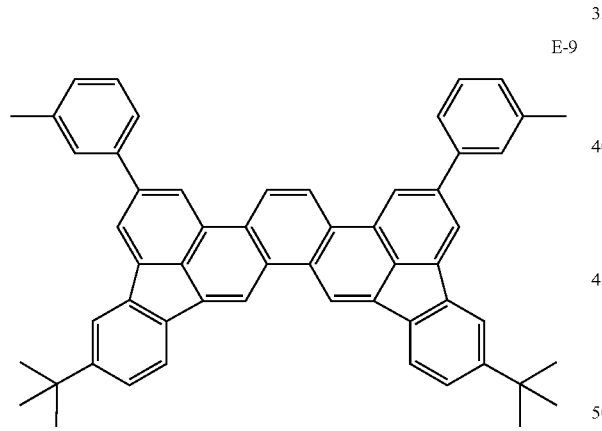
E-10
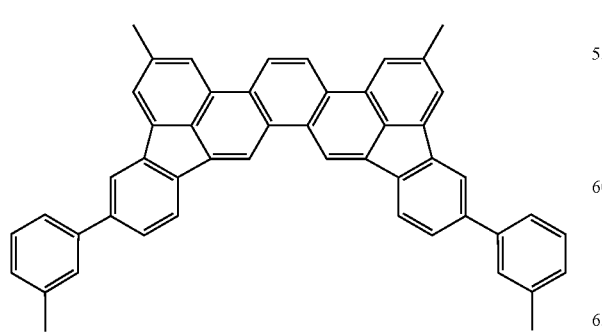
-continued
E-11
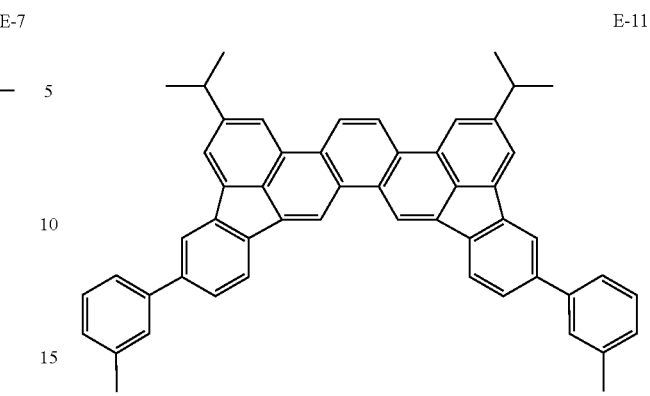
E-12
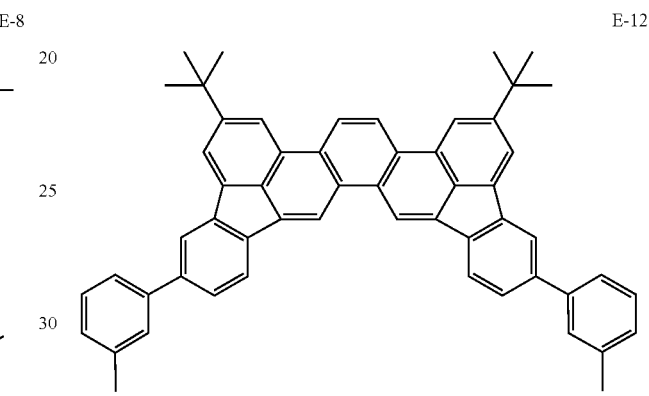
Formula 10
E-13
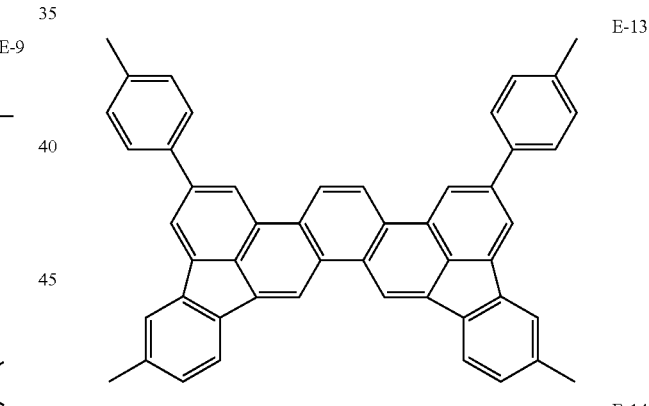
E-14
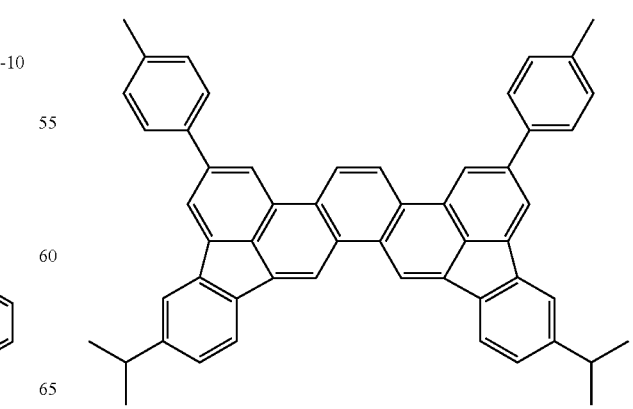

-continued
E-15
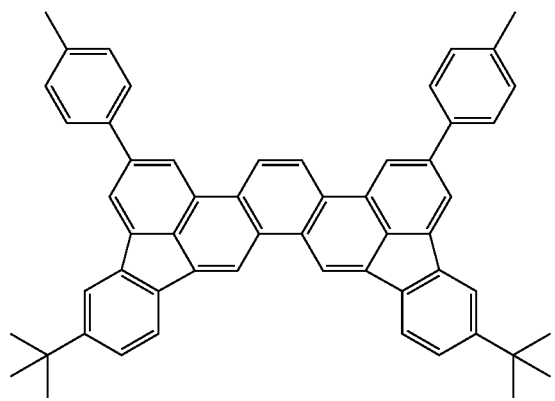
E-16
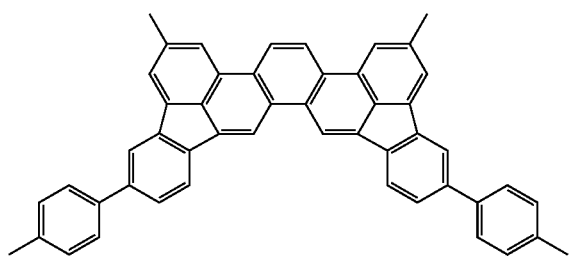
E-17
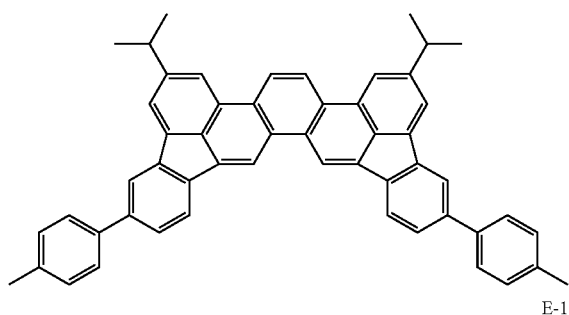
E-18
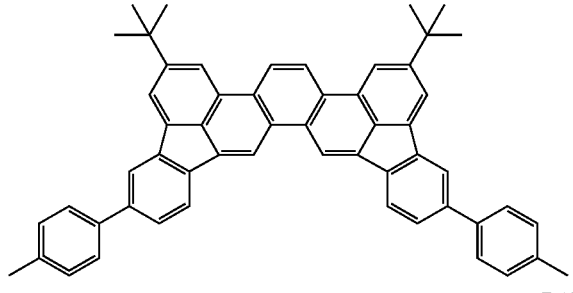
E-19
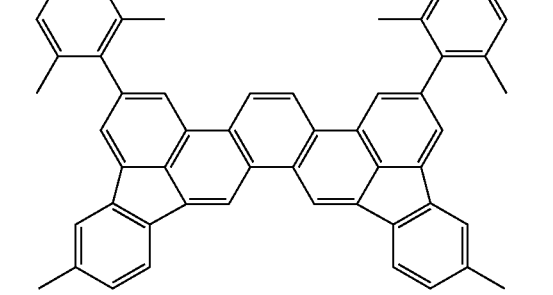
E-20
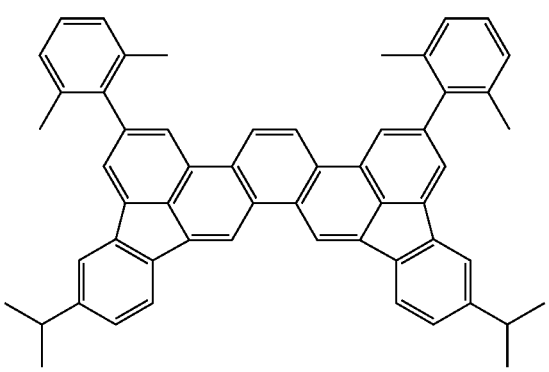
E-21
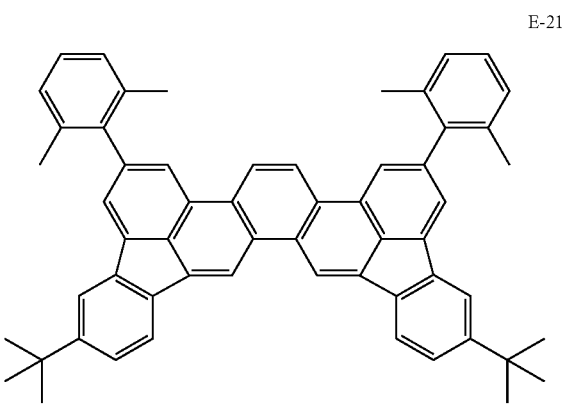
E-22
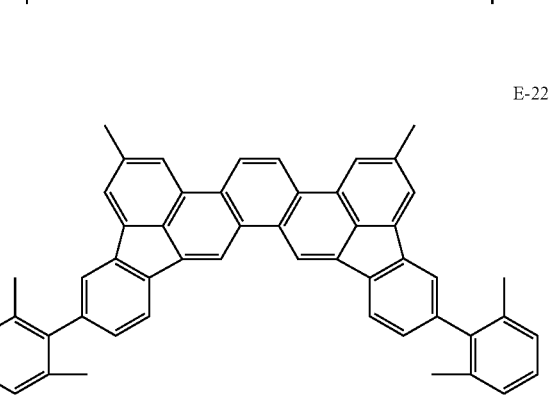
E-23
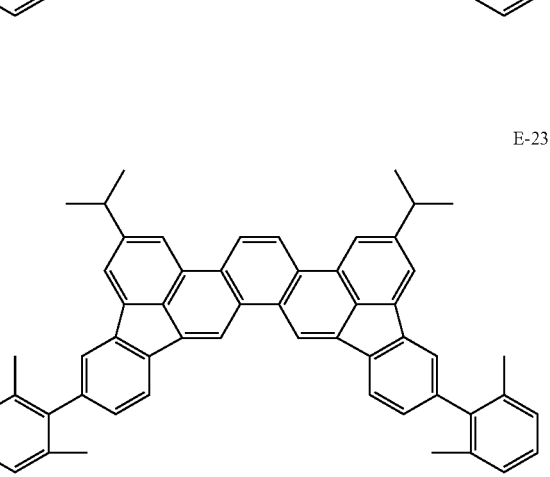

-continued
E-24
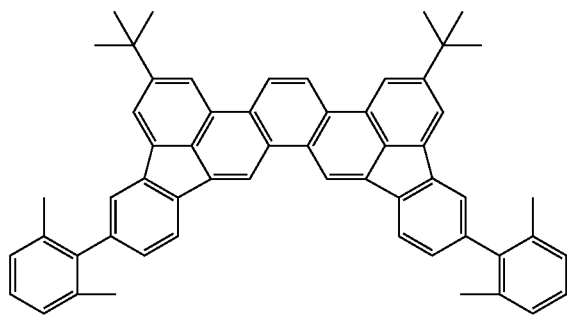
E-25
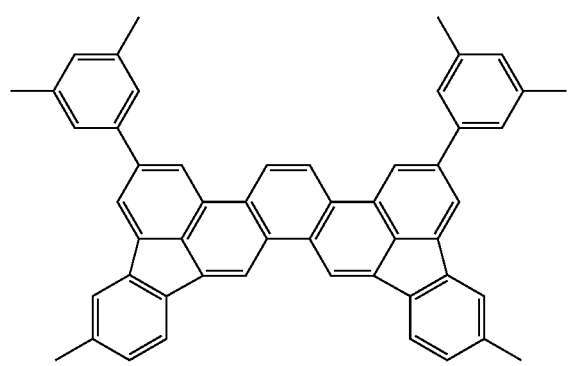
E-26
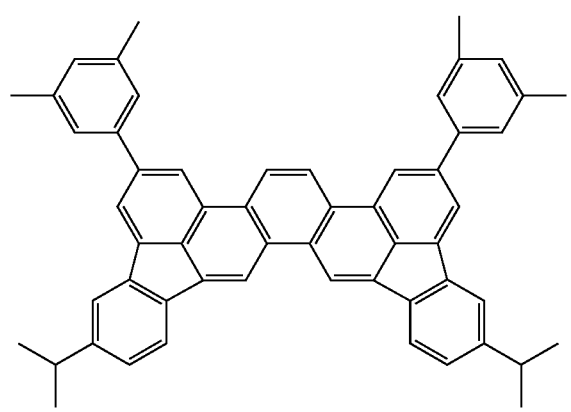
E-27
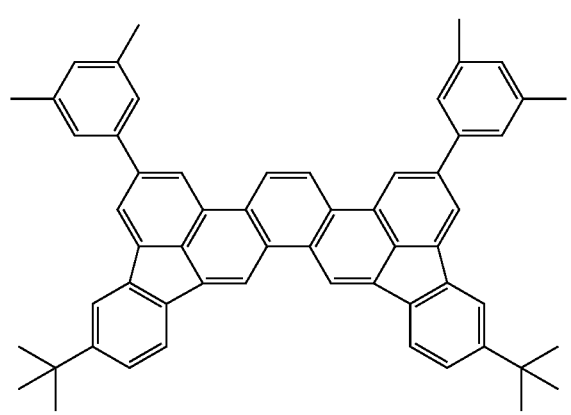
-continued
E-28
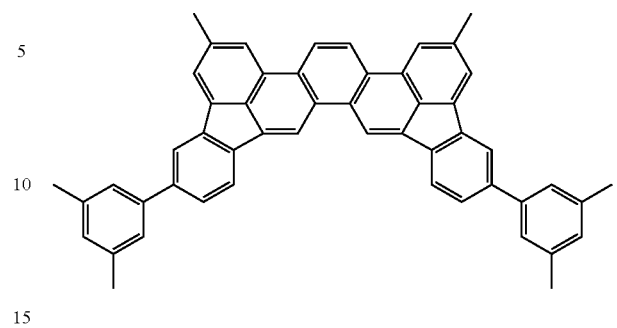
E-29
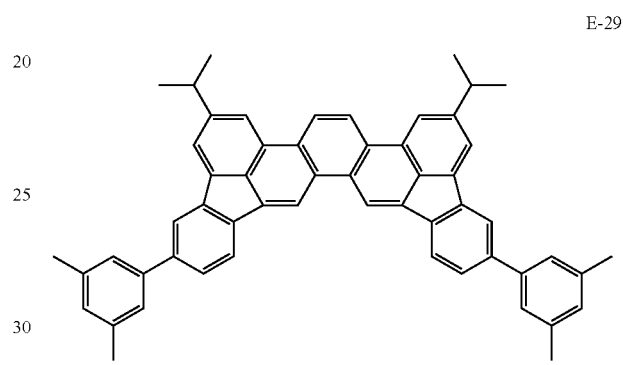
E-30
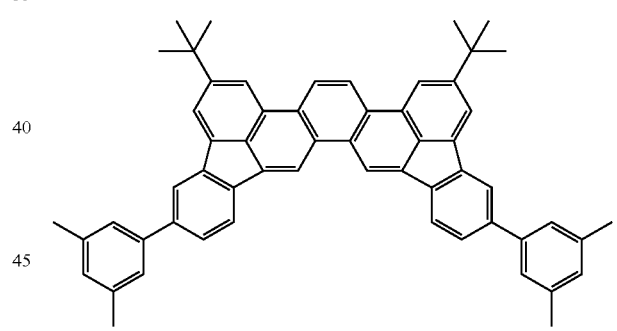
Formula 11
E-31
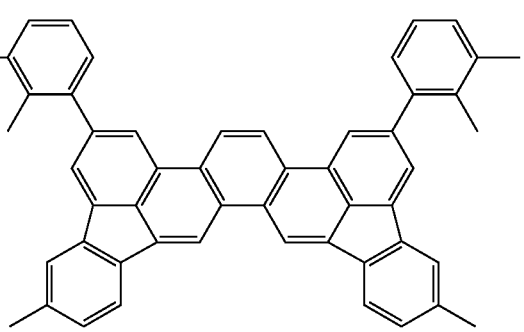

-continued
E-32
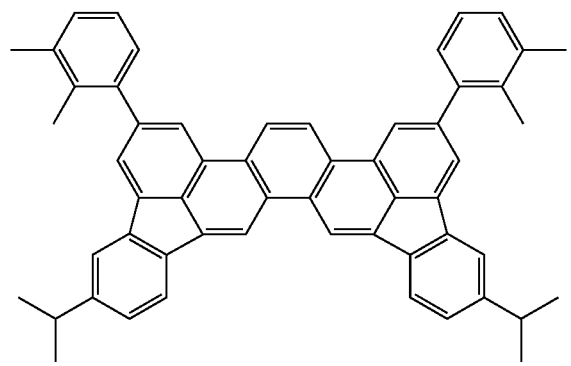
E-33
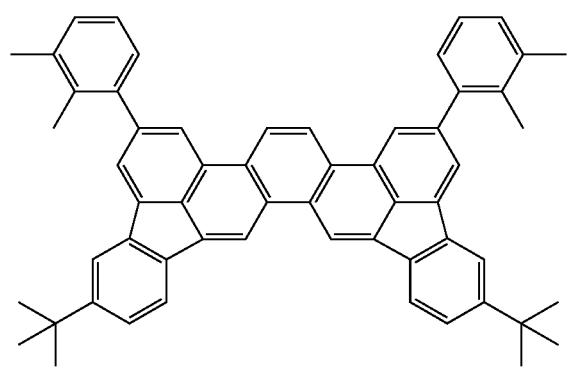
E-34
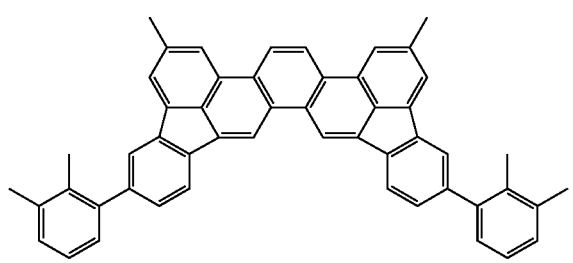
E-35
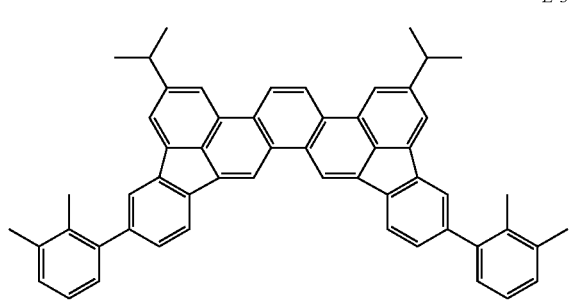
-continued
E-36
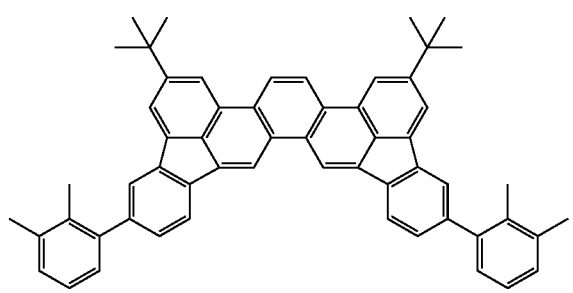
E-37
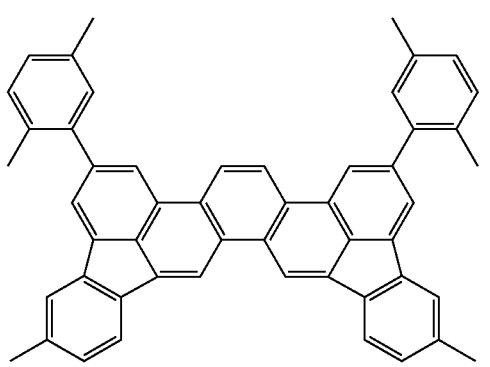
E-38
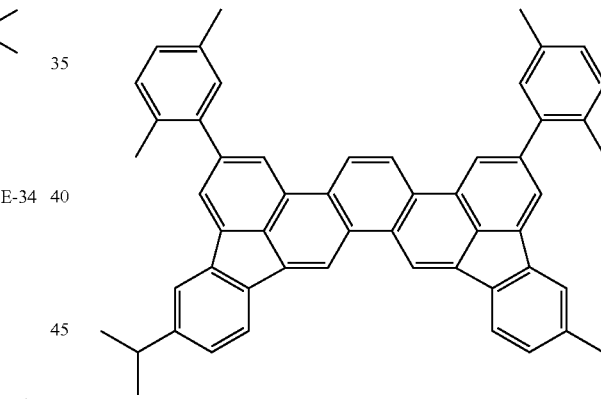
E-39
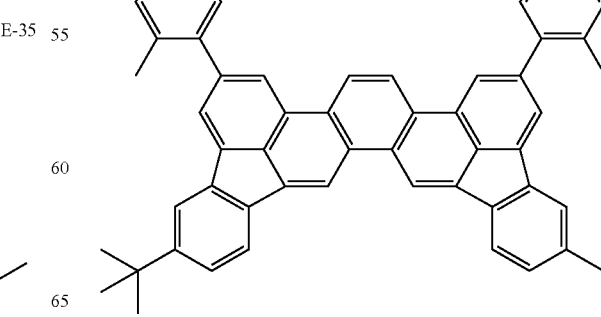

E-40
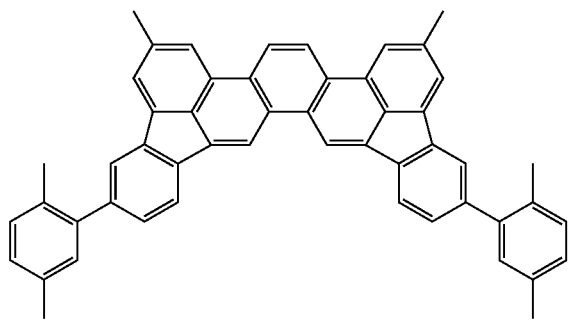
E-41
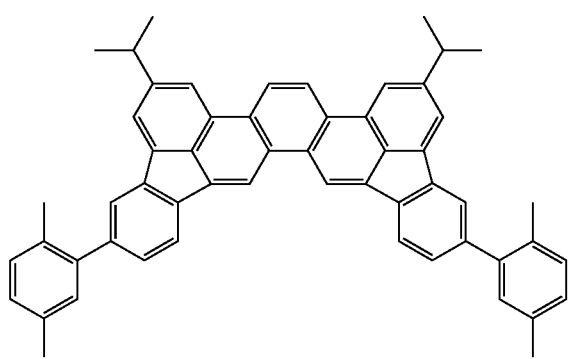
E-42
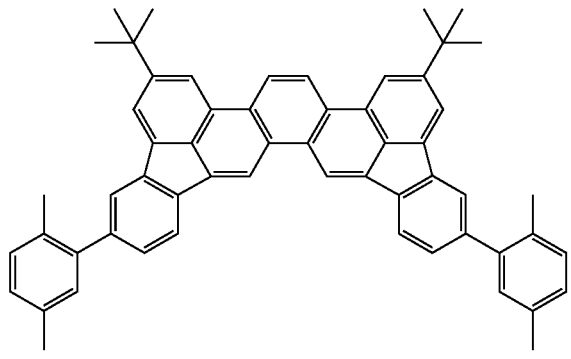
E-43
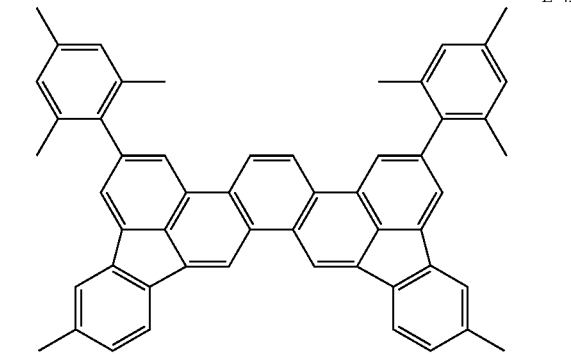
E-44
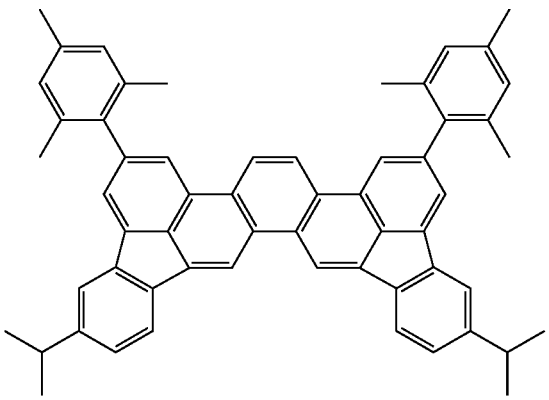
E-45
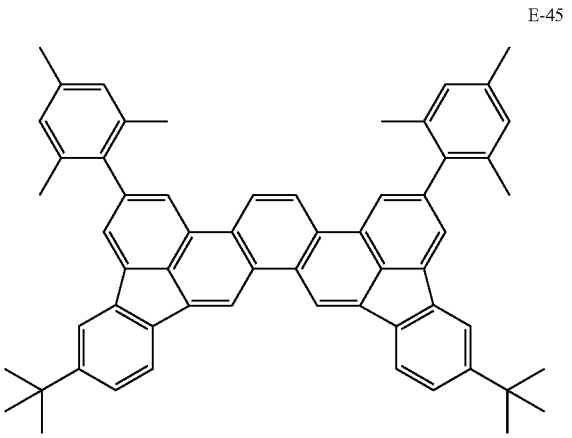
E-46
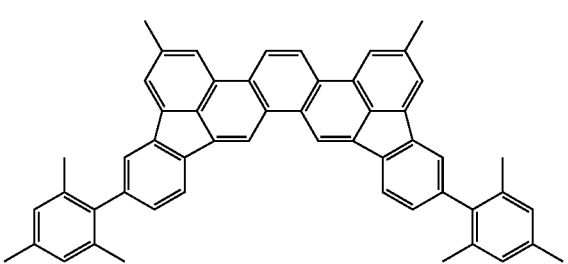
E-47
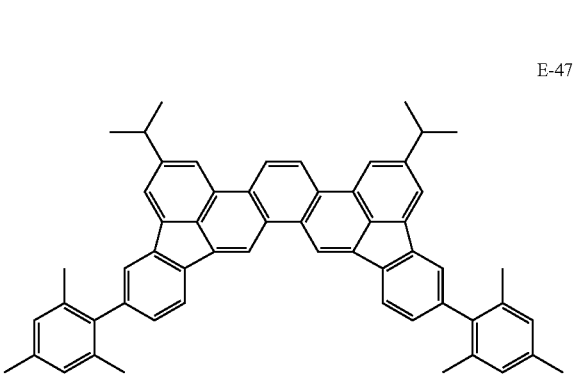

E-48
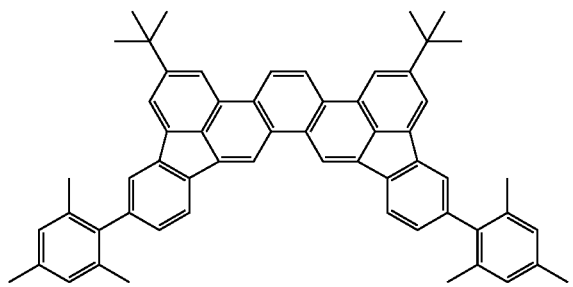
Formula 12
E-49
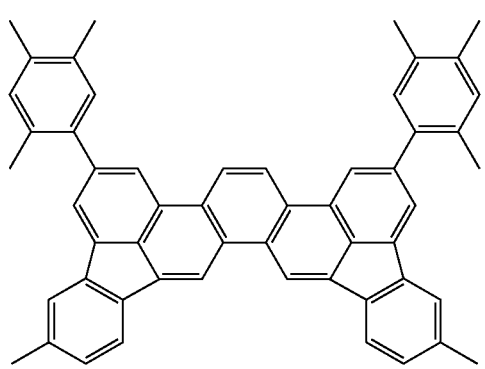
E-50
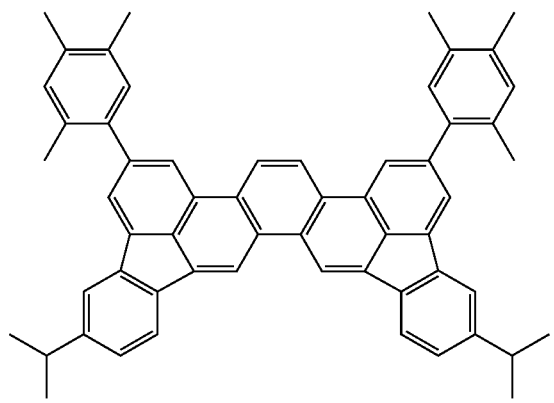
E-51
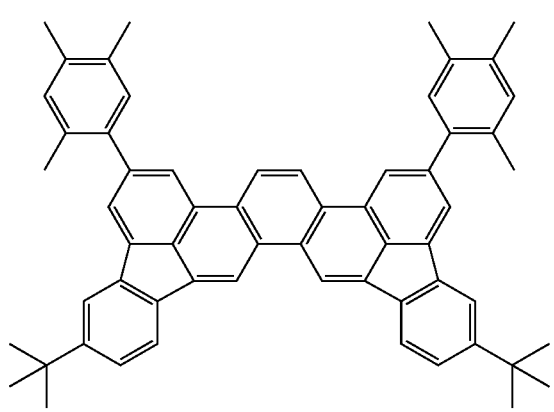
E-52
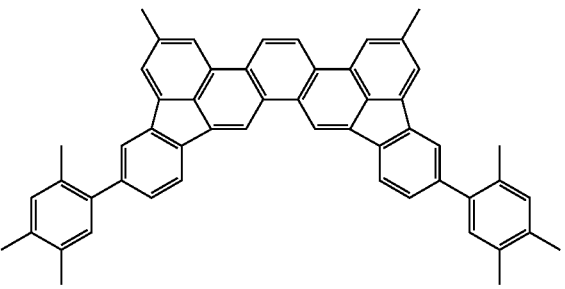
E-53
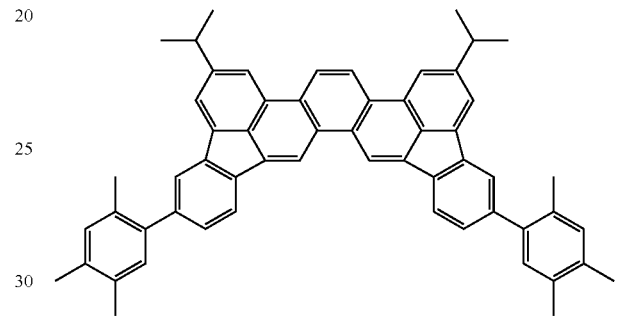
E-54
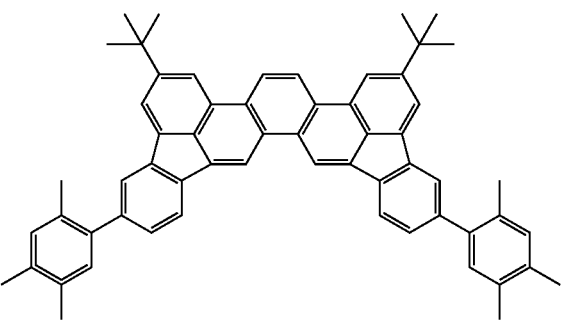
E-55
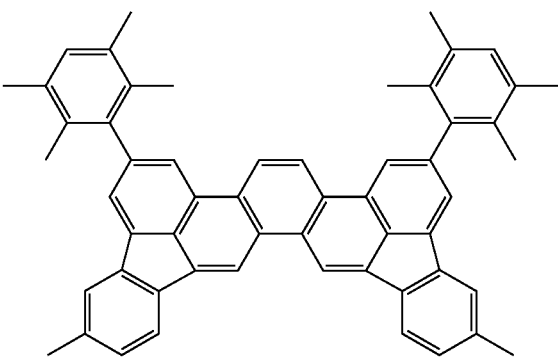

E-56
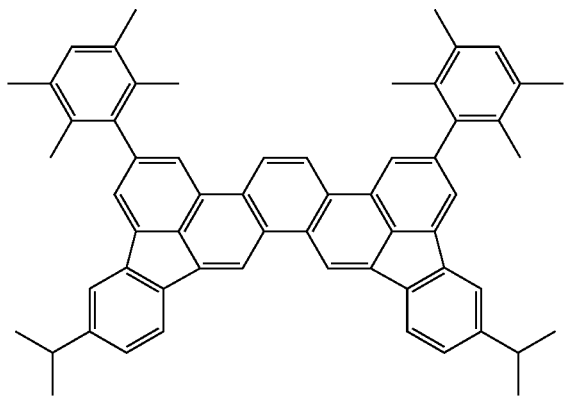
E-57
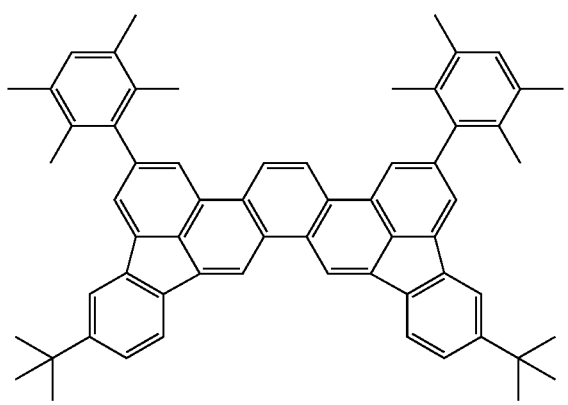
E-58
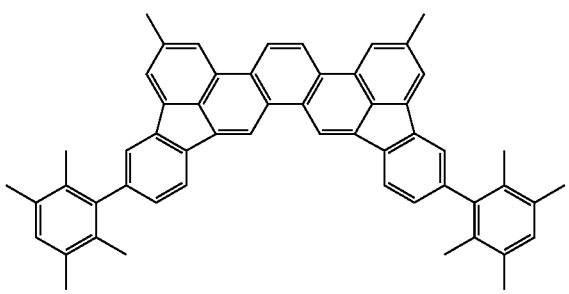
E-59
E-60
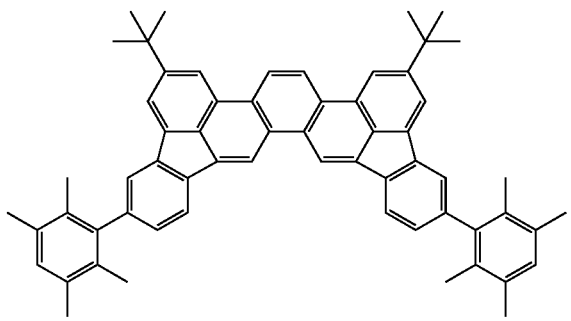
E-61
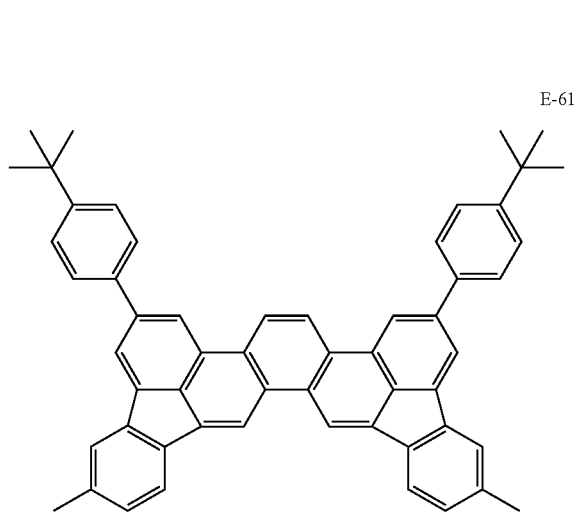
E-62
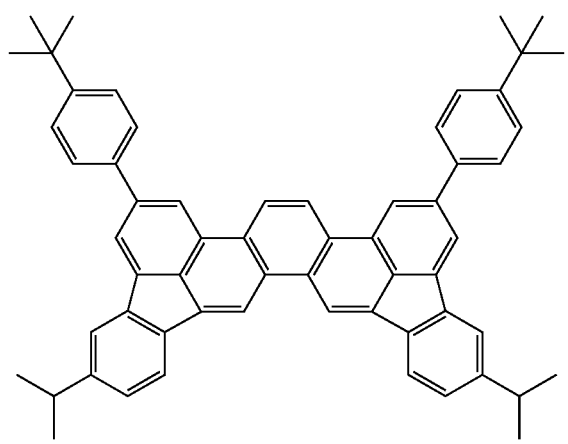

Formula 13
E-63
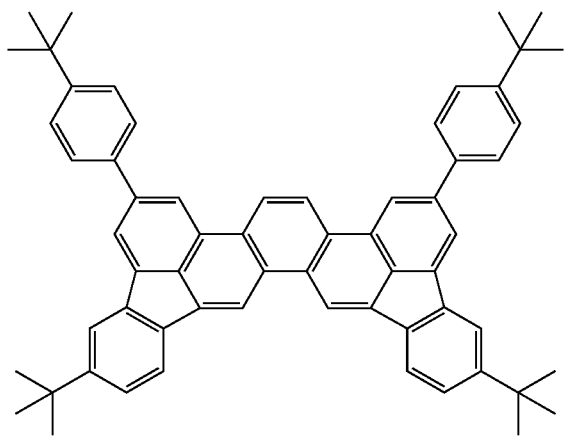
E-64
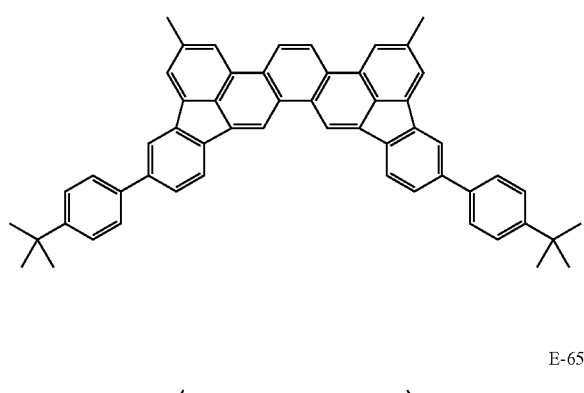
E-65
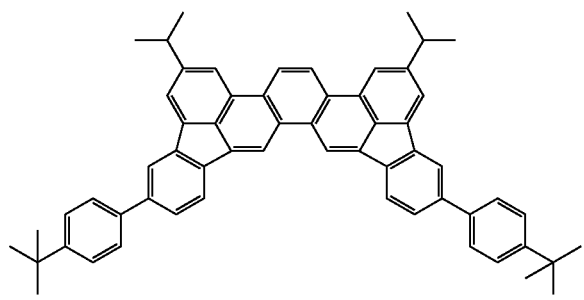
E-66
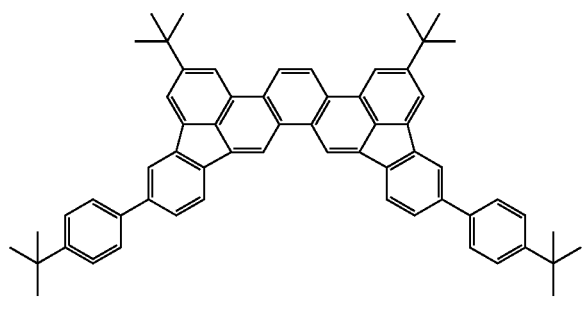
E-67
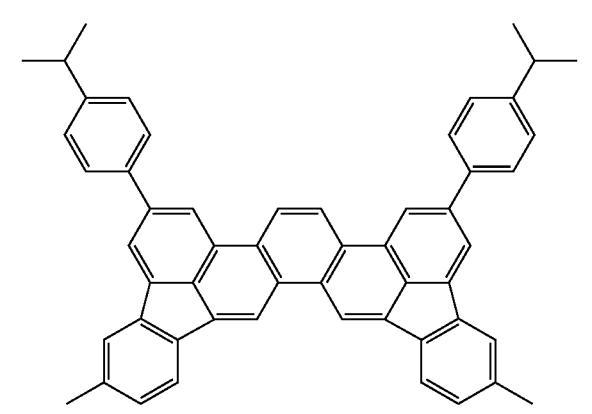
E-68
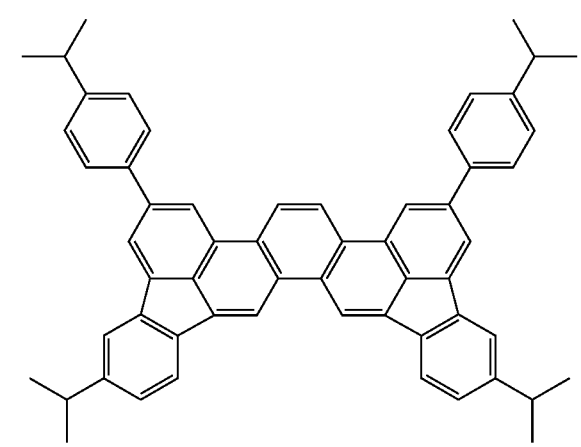
E-69
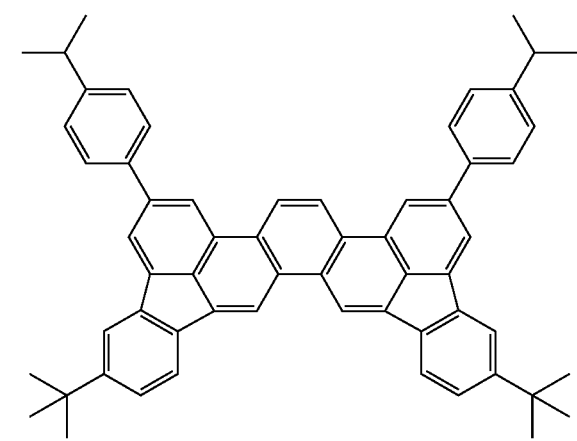
E-70
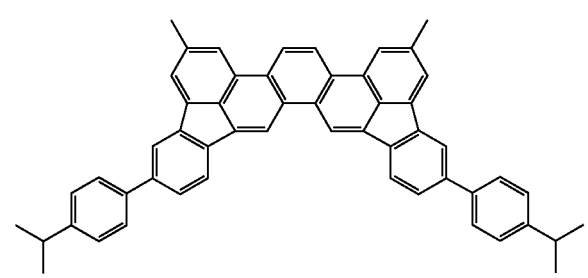

E-71
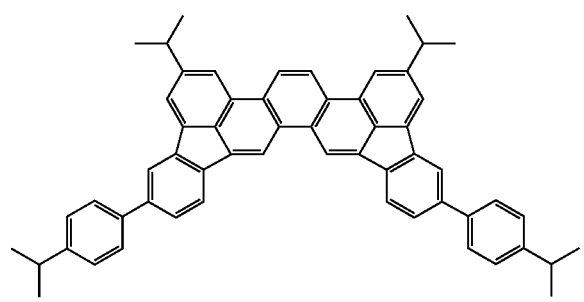
E-75
E-72
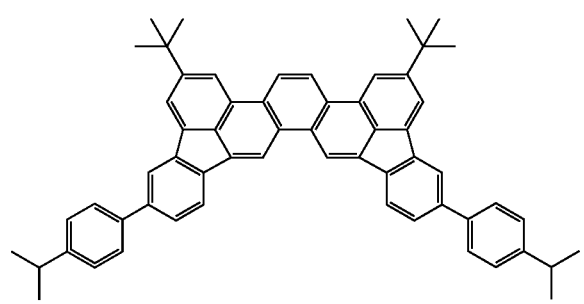
E-76
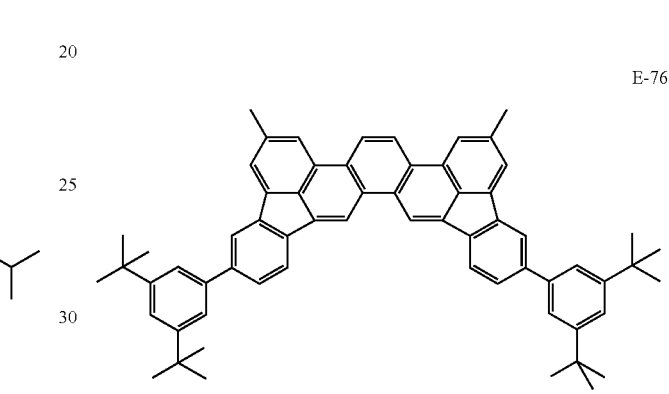
E-73
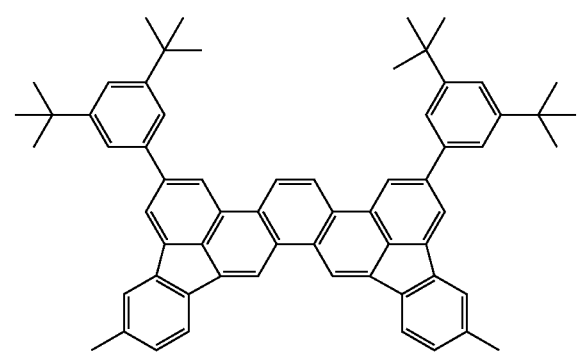
E-77
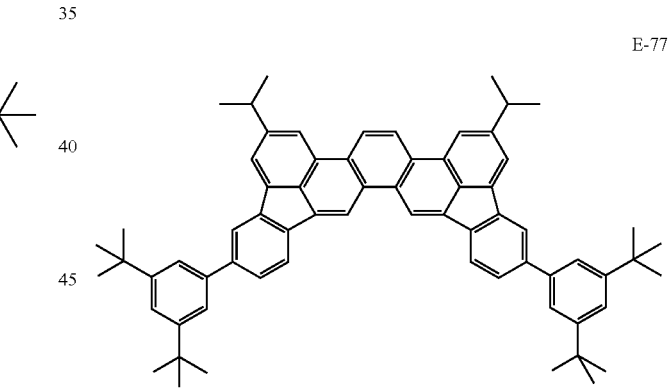
E-74
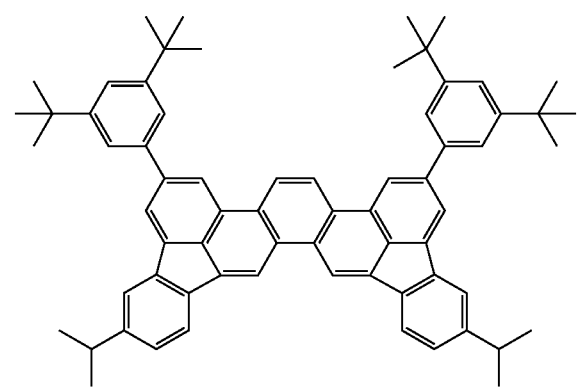
E-78
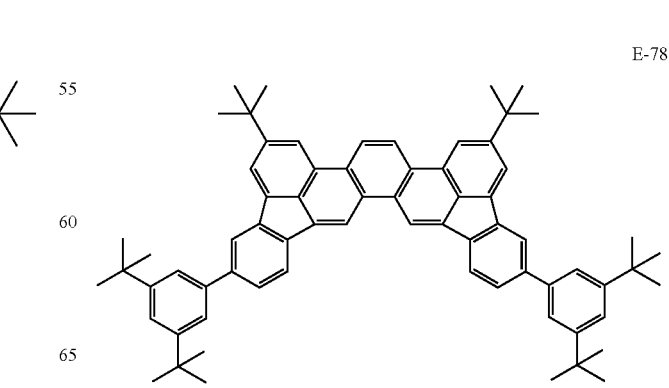

-continued
E-79
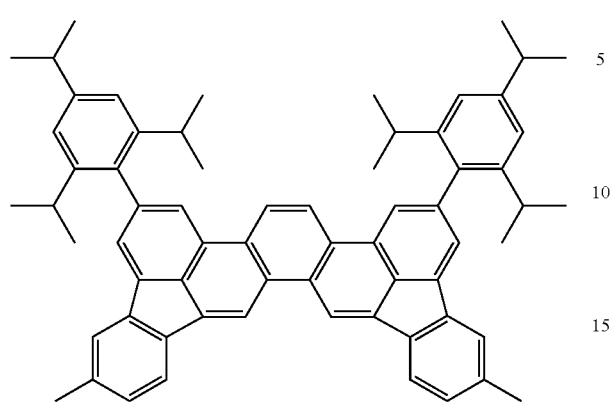
E-80
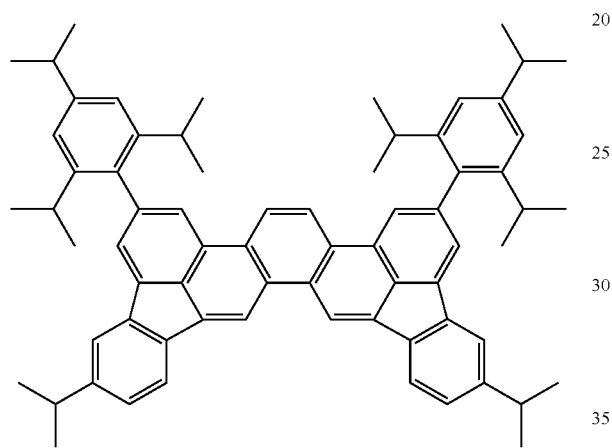
E-81
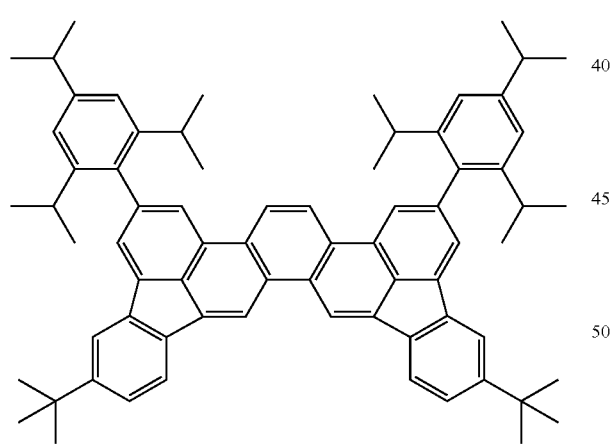
E-82
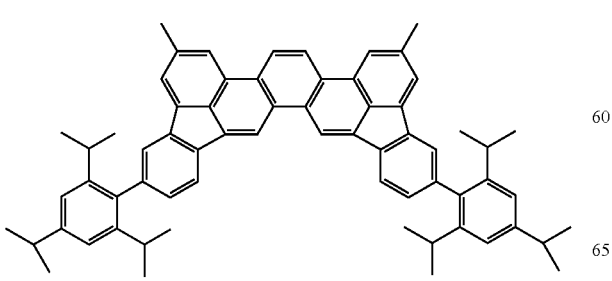
-continued
E-83
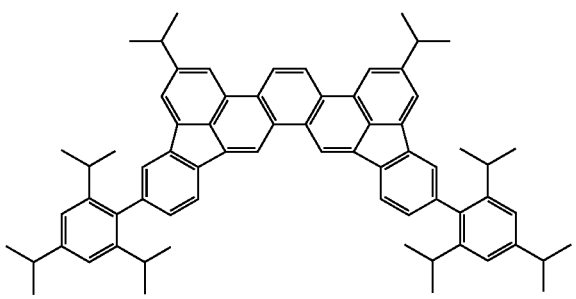
E-84
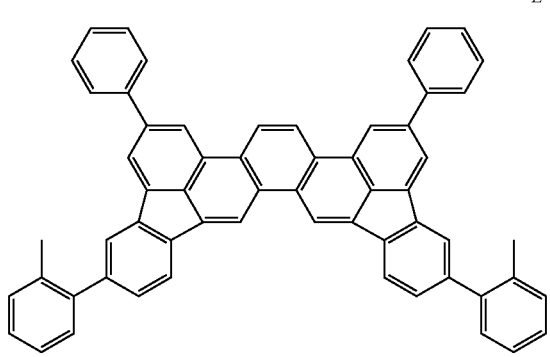
Formula 14
E-85
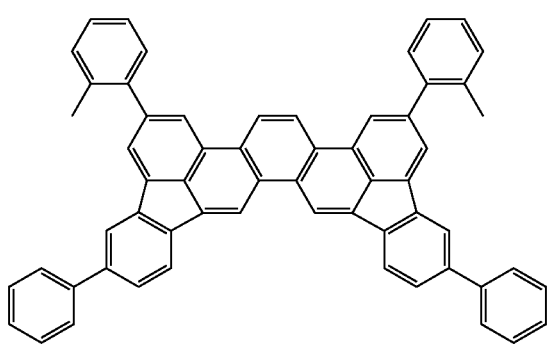
E-86

E-87
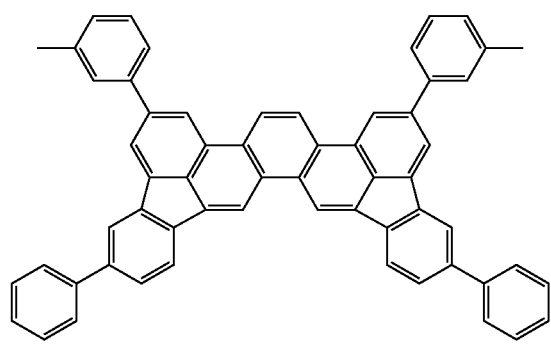
E-88
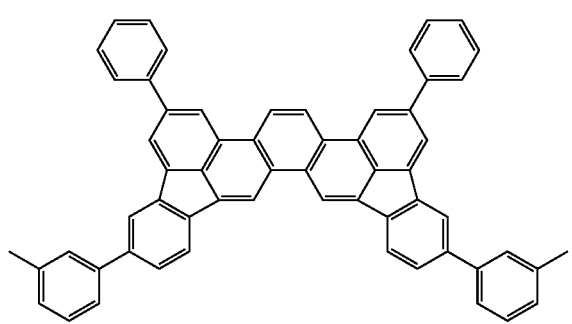
E-89
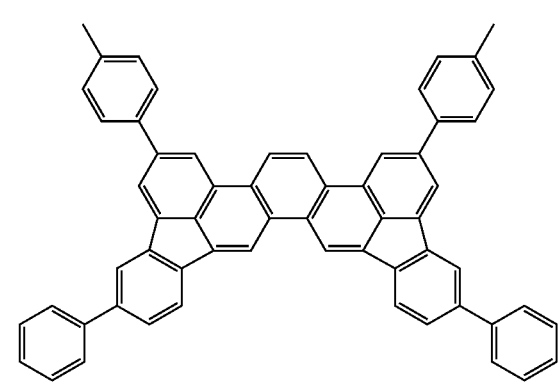
E-90
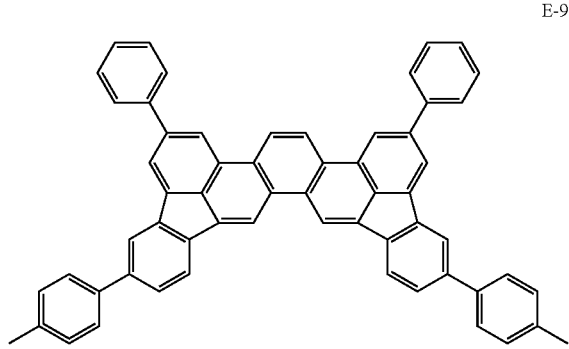
E-91
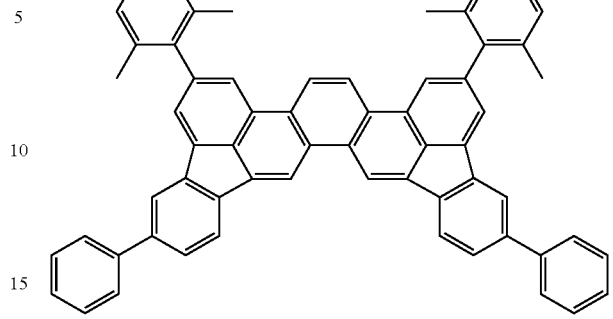
E-92
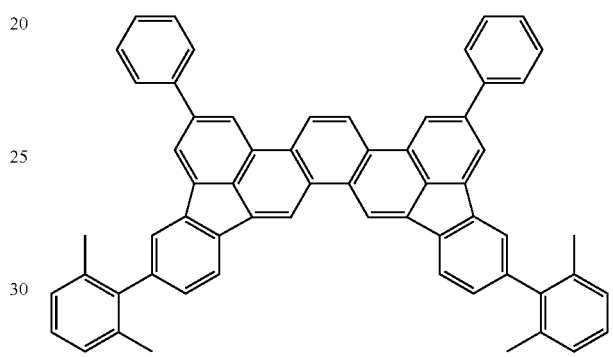
E-93
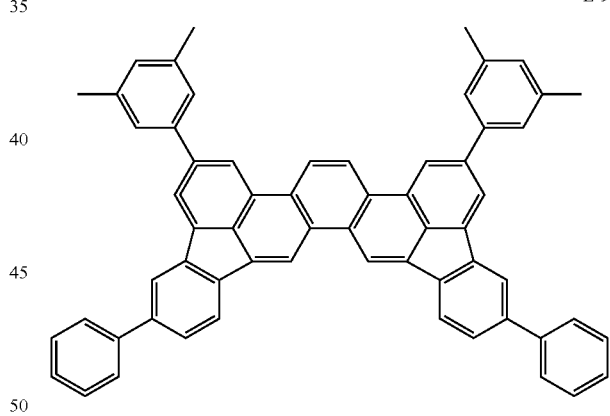
E-94
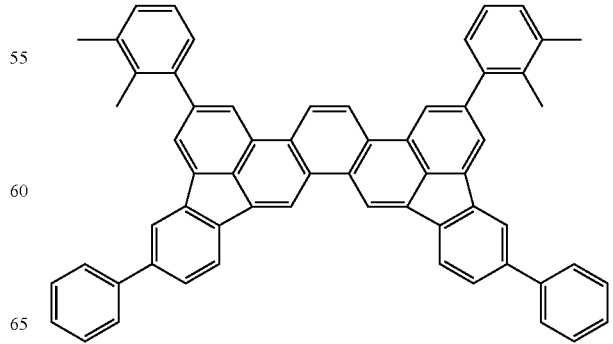

E-95
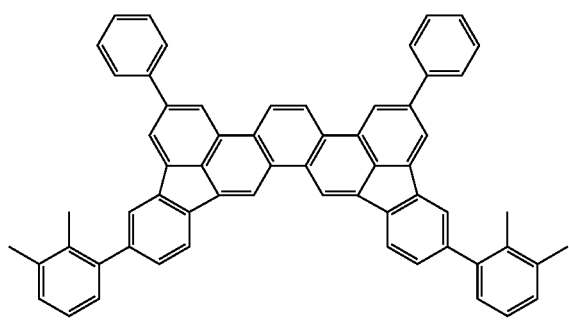
E-99
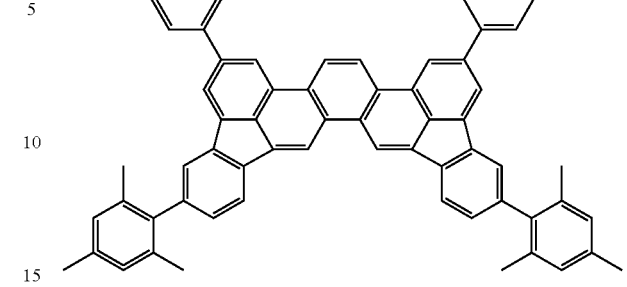
E-96
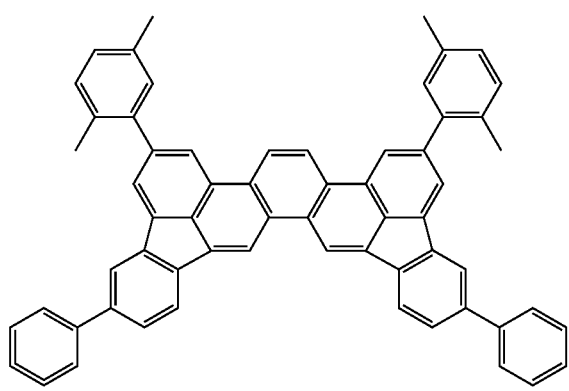
E-100
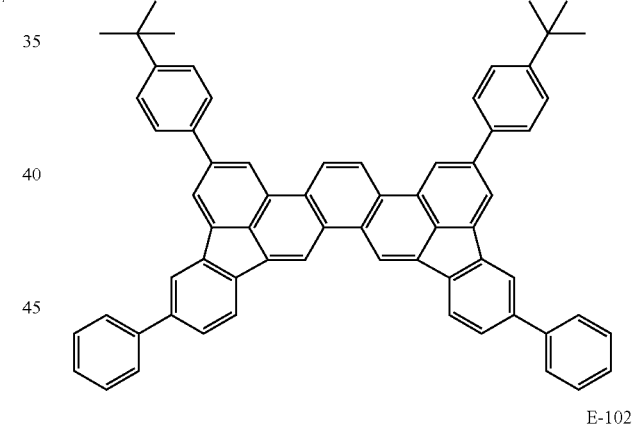
E-97
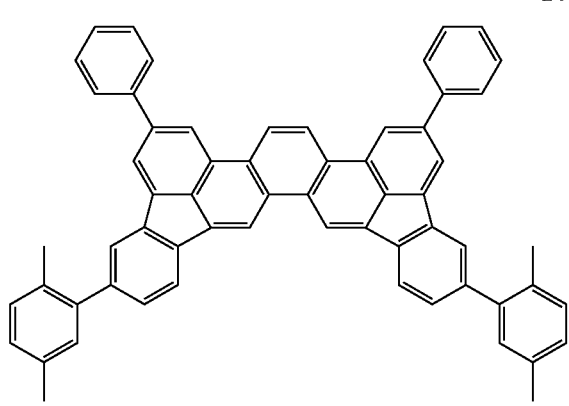
E-101
E-98
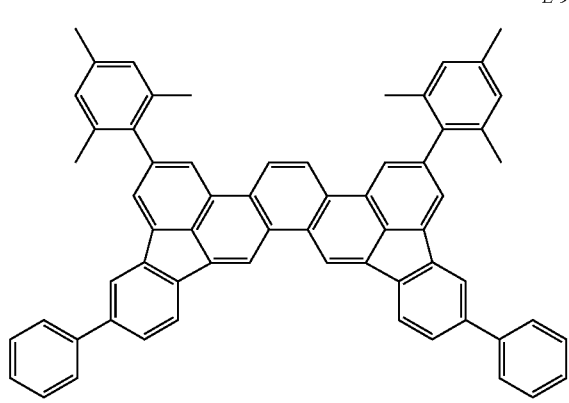
E-102
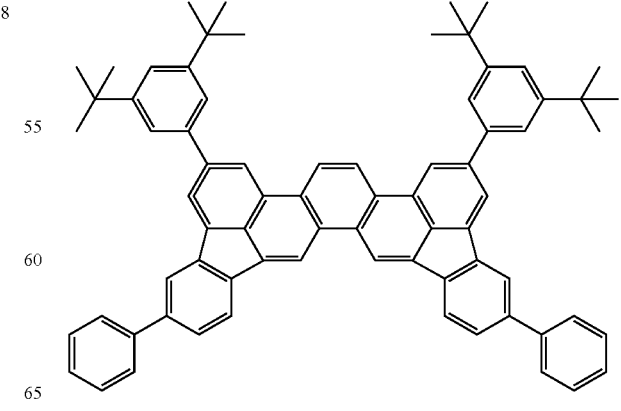

Formula 15
E-103
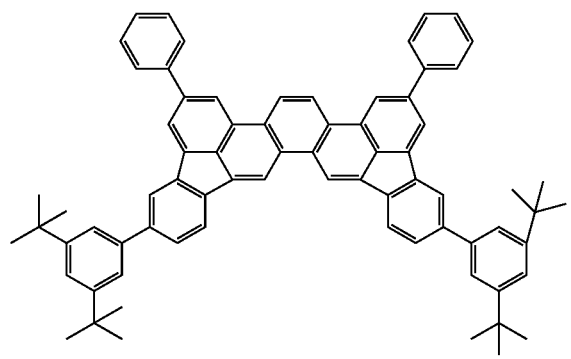
E-104
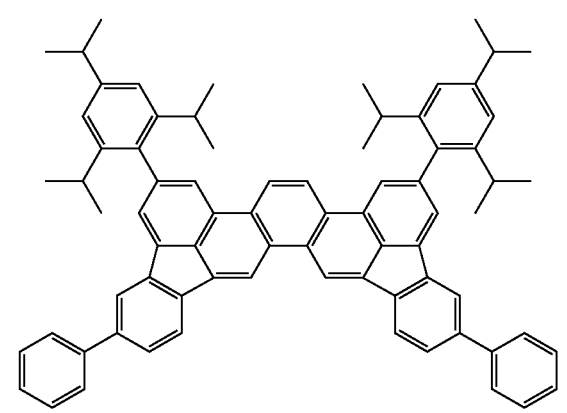
E-105
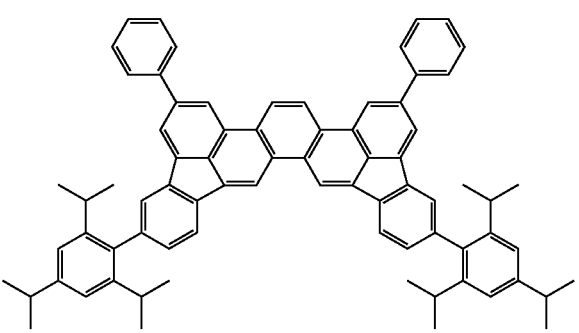
F-1
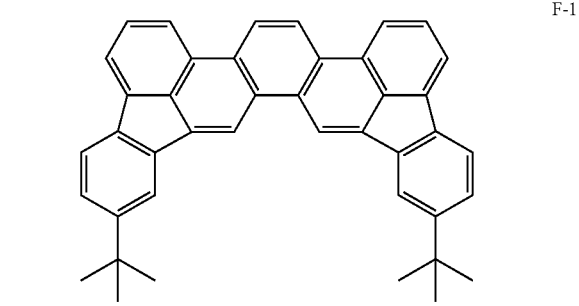
F-2
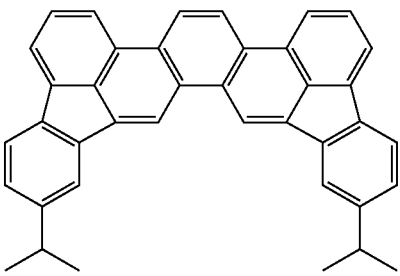
F-3
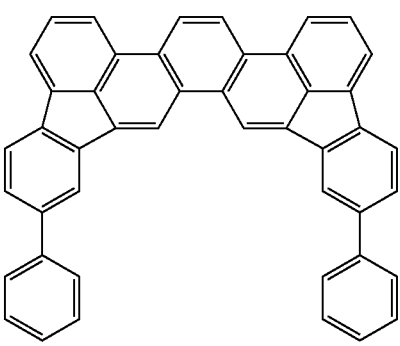
F-4
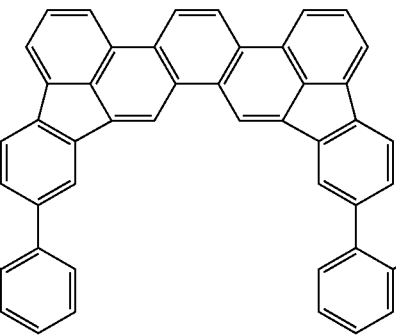
F-5
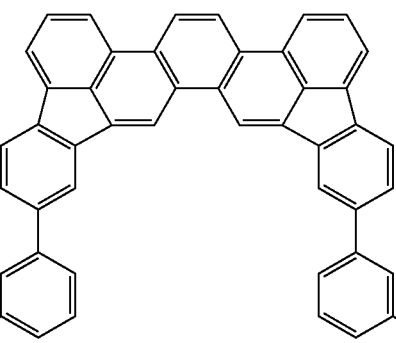

-continued
F-6
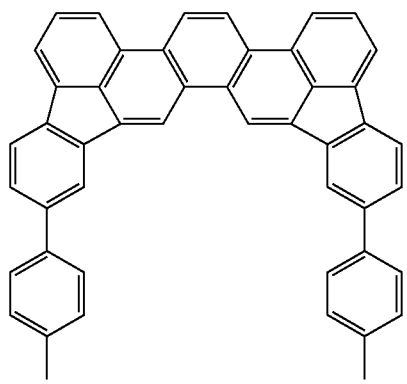
F-7
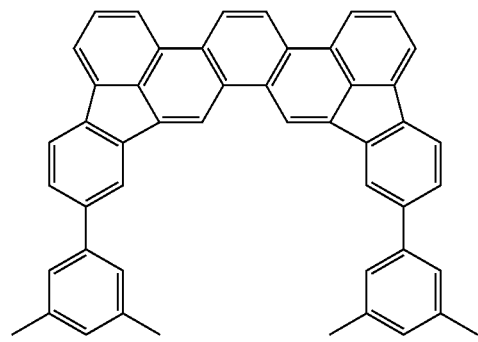
F-8
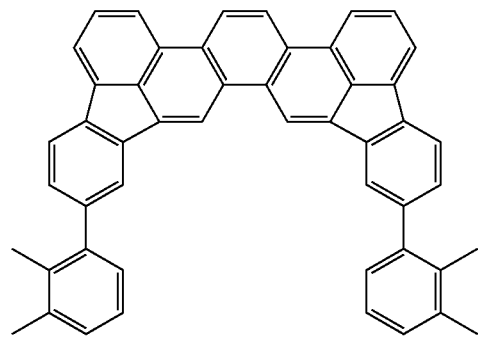
-continued
F-10
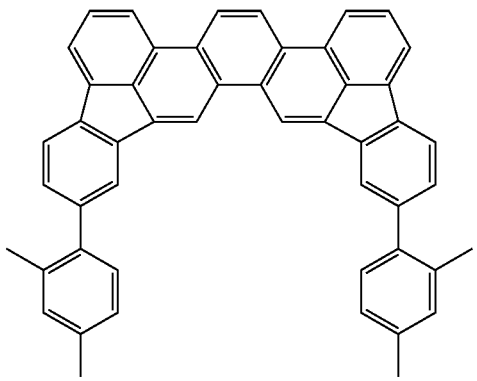
F-11
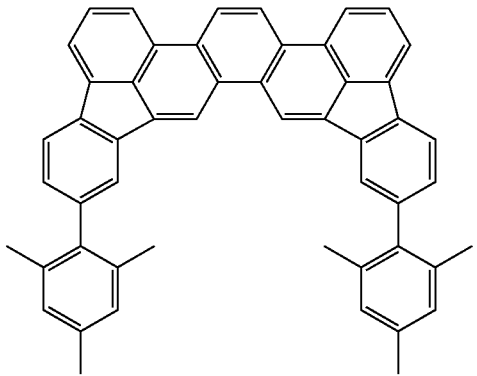
F-12
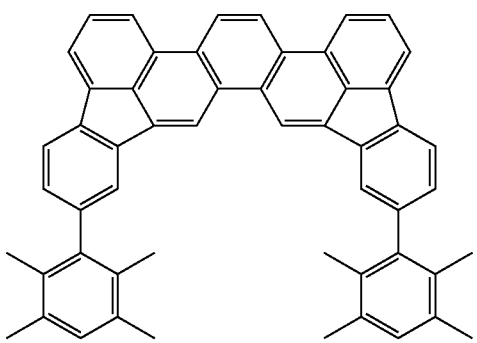
F-9
F-13

F-14
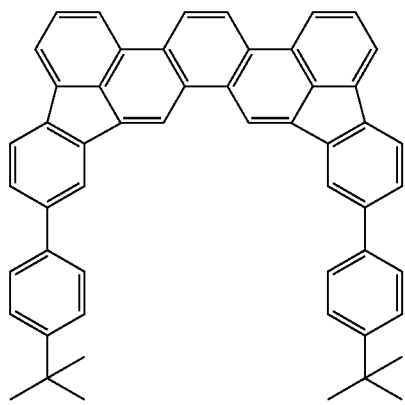
F-15
Formula 16
F-16
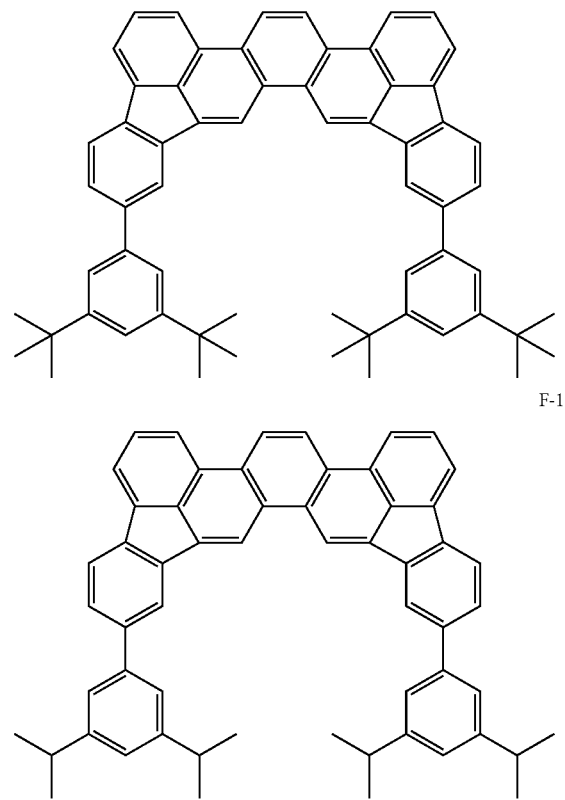
F-17
F-18
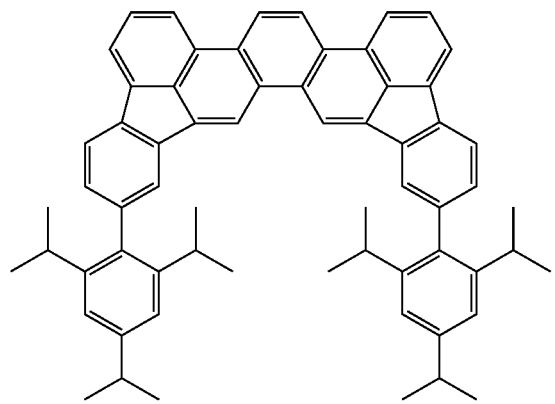
G-1
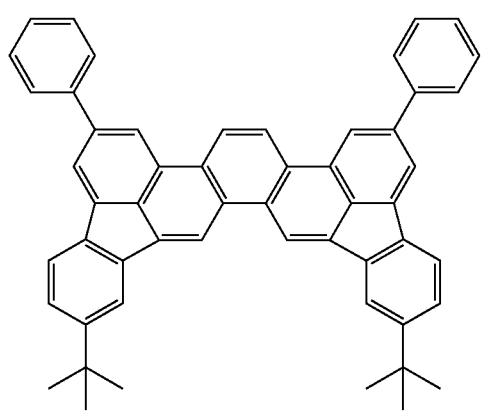
G-2
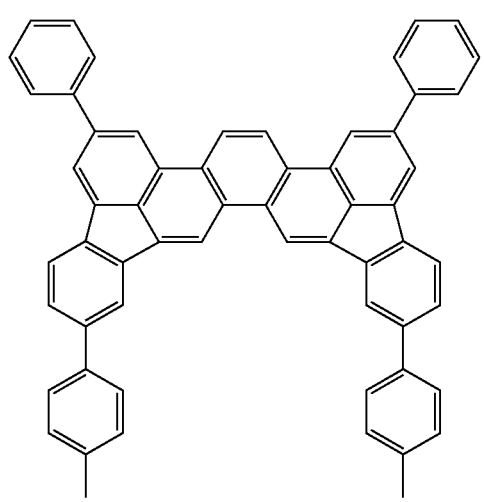

G-3
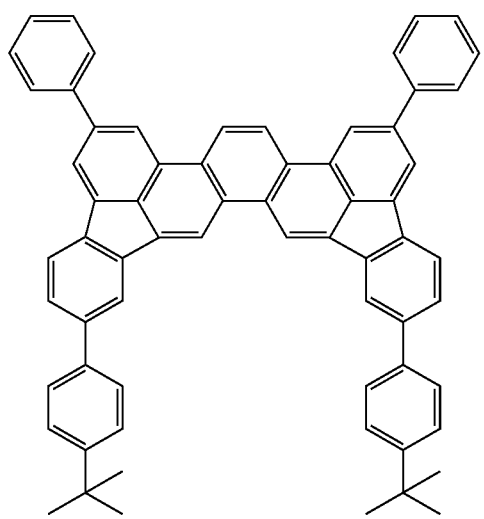
G-4
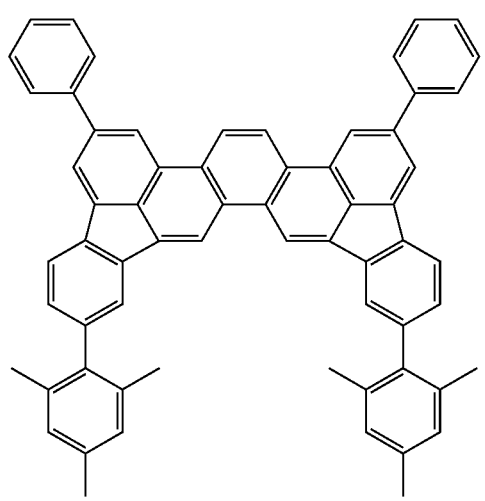
G-5
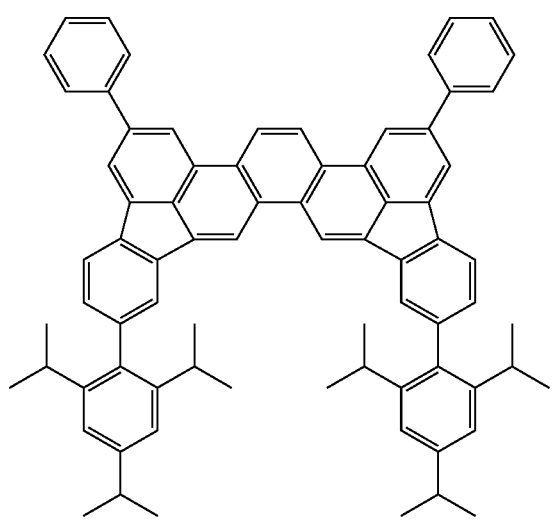
G-6
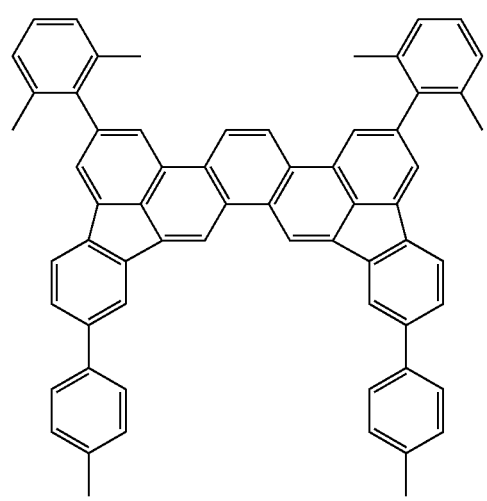
G-7
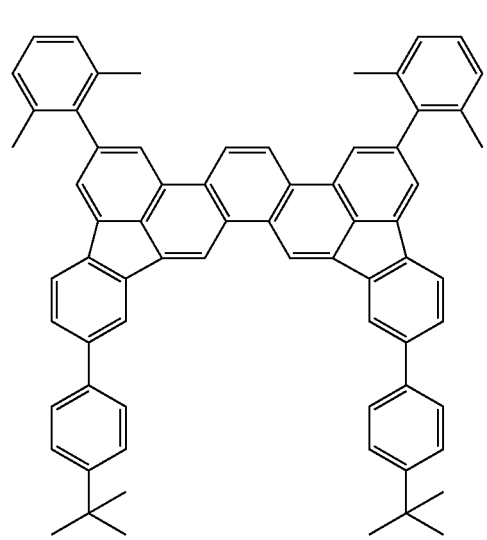
G-8
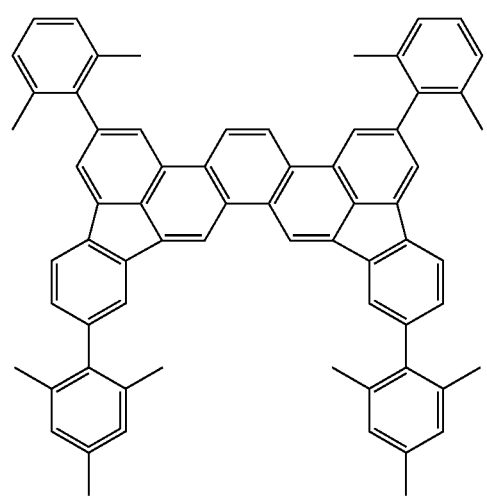

G-9
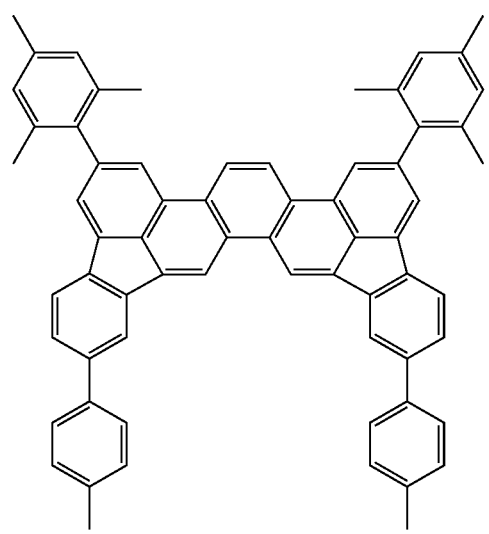
G-10
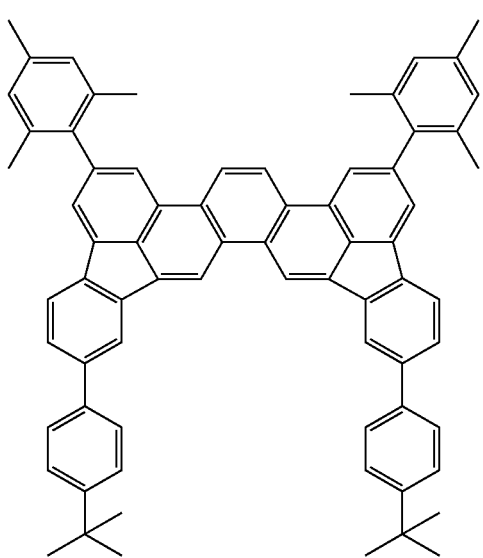
G-11
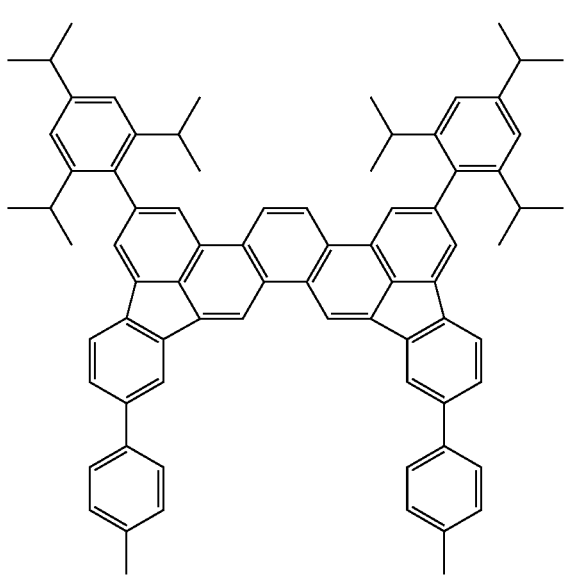
G-12
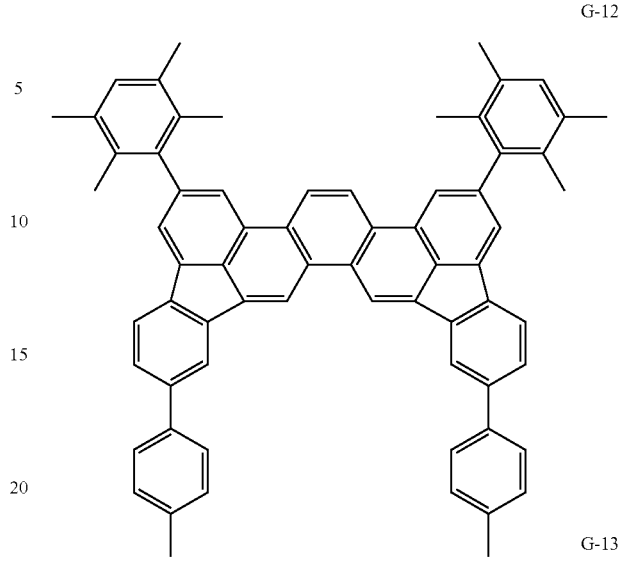
G-13
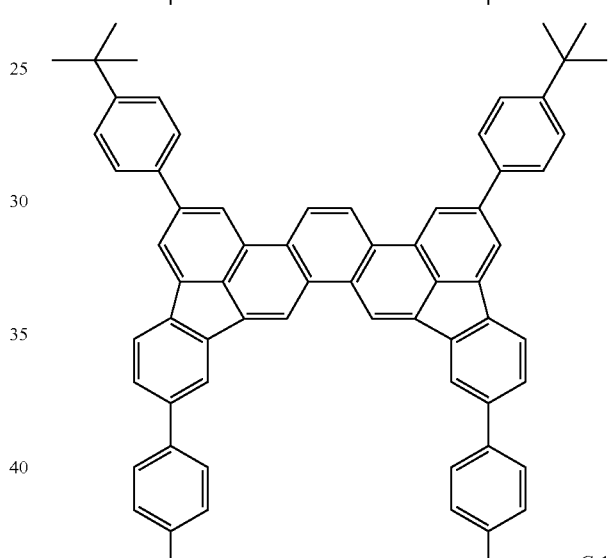
G-14
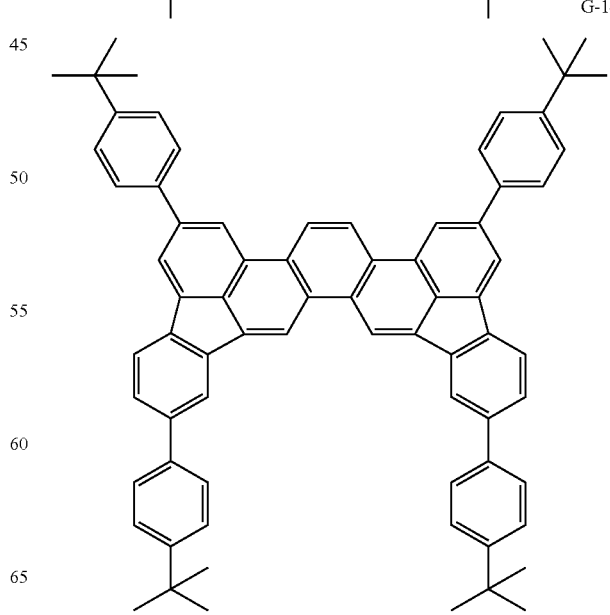

-continued
G-15
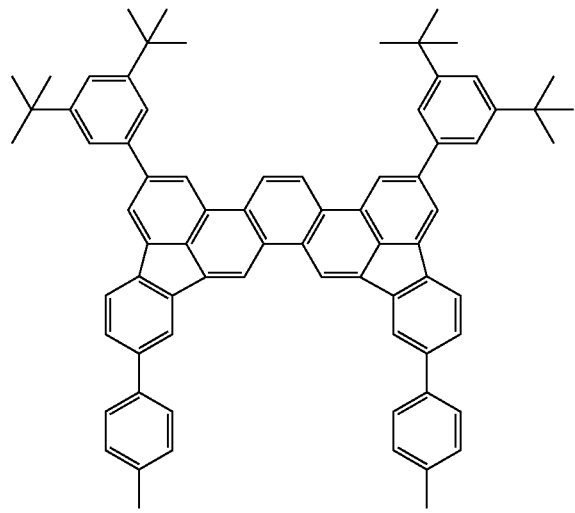
Formula 17
G-16
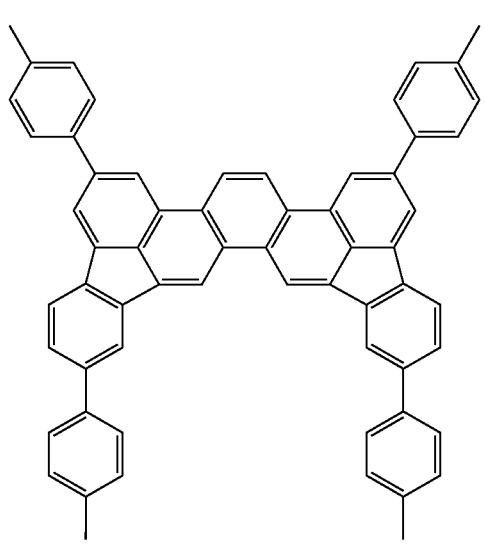
G-17
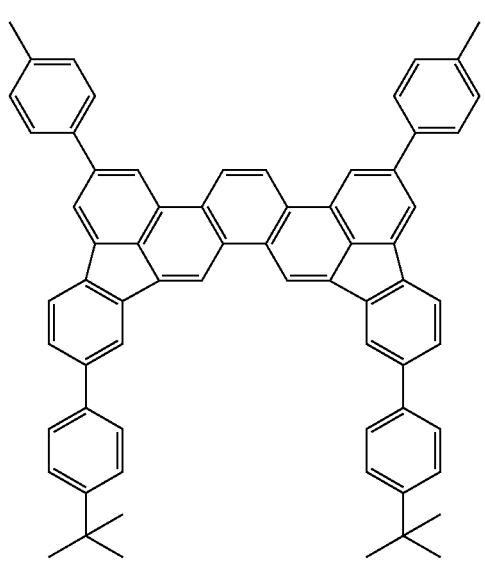
-continued
G-18
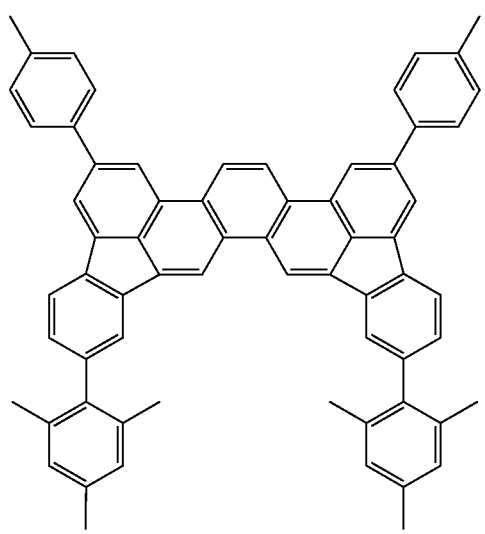
G-19
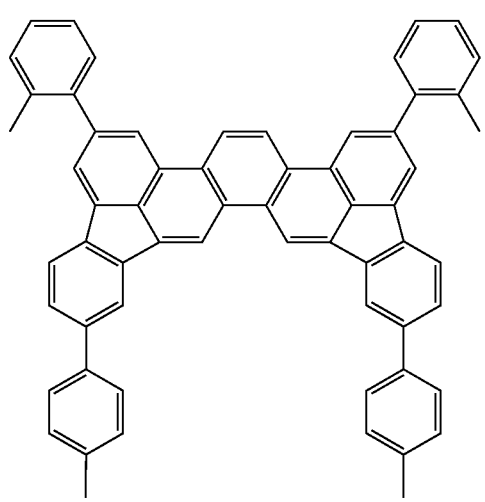
G-20
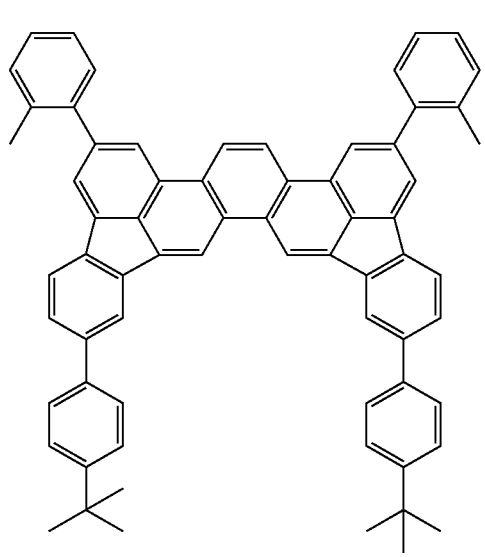

-continued
G-21
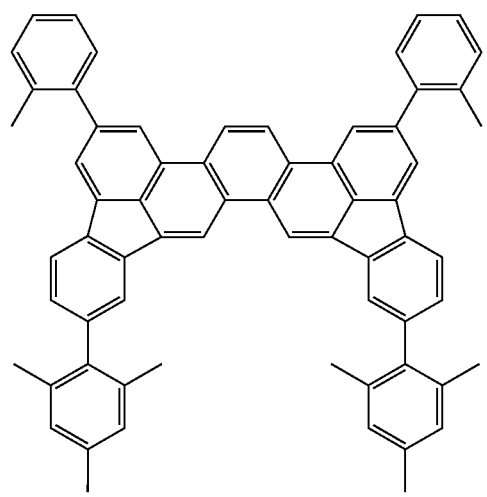
G-22
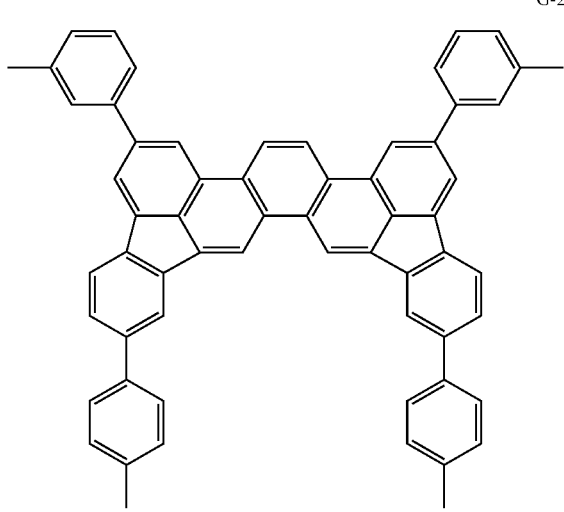
G-23
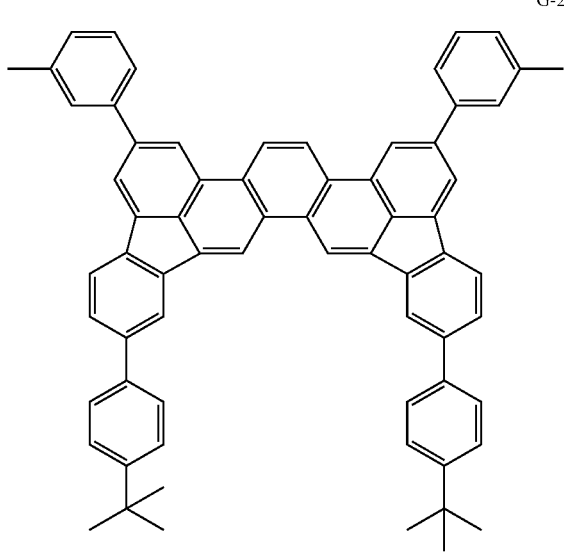
-continued
G-24
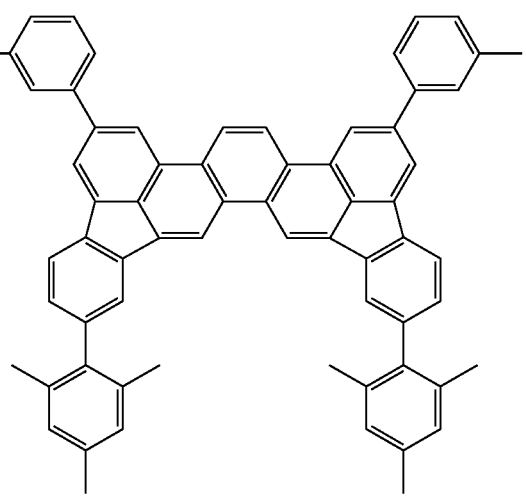
G-25
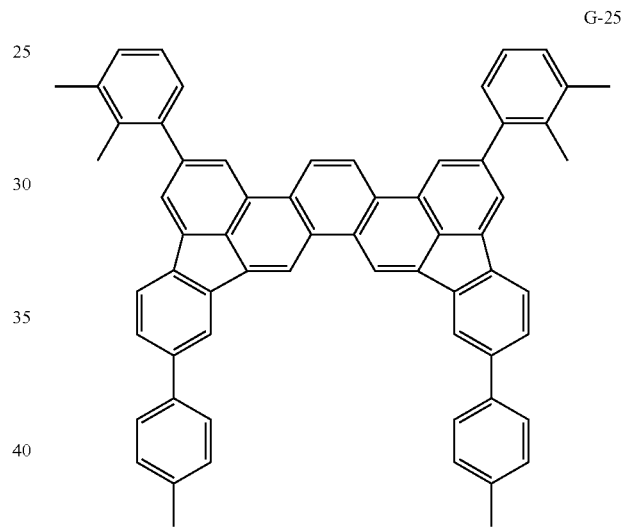
G-26
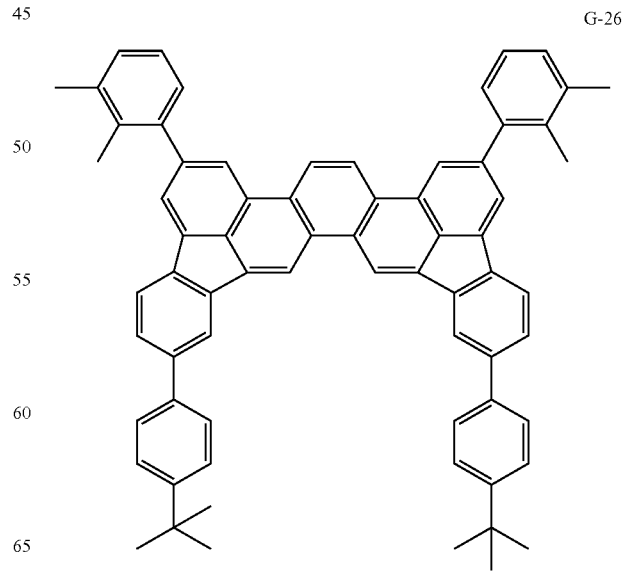

G-27

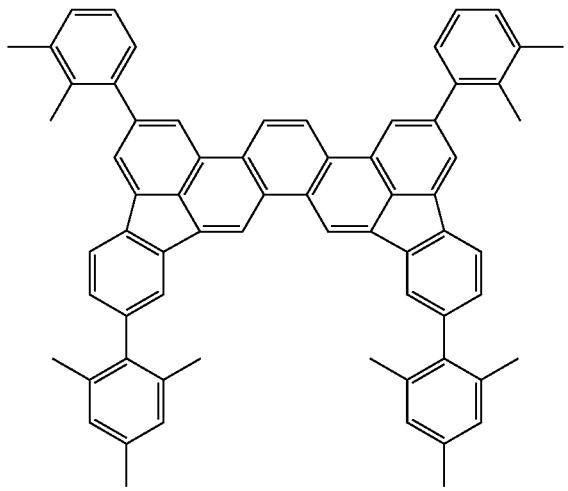

Next, the organic light emitting device of the present invention will be described. The organic light emitting device of the present invention includes an anode, a cathode and an organic compound layer sandwiched in between the anode and the cathode. In the organic light emitting device of the present invention, it is preferable that the anode or the cathode be formed of a transparent or semitransparent electron material.

Hereinafter, the organic light emitting device of the present invention will be further described in detail with reference to the drawings.

First, reference numerals in the drawings are described. Reference numeral 1 denotes a substrate; reference numeral 2 denotes an anode; reference numeral 3 denotes a light emitting layer; reference numeral 4 denotes a cathode; reference numeral 5 denotes a hole transport layer; reference numeral 6 denotes an electron transport layer; reference numeral 7 denotes a hole injection layer; reference numeral 8 denotes a hole/exciton blocking layer; and reference numerals 11, 12 to 15 each denote an organic light emitting device. FIGS. 1A, 1B, 1C, 1D and 1E are a cross-sectional schematic diagram illustrating an exemplary embodiment in an organic light emitting device according to the present invention. In the organic light emitting device 11 illustrated in FIG. 1A, the anode 2, the light emitting layer 3 and the cathode 4 are provided in this order over the substrate 1. The organic light emitting device 11 is useful in the case where the light emitting layer 3 is formed of a compound having all the capabilities of hole transportability, electron transportability and light emitting ability, and in the case where the light emitting layer 3 is formed by incorporating a compound having any of the hole transportability, electron transportability and light emitting ability.

Figure 1B:
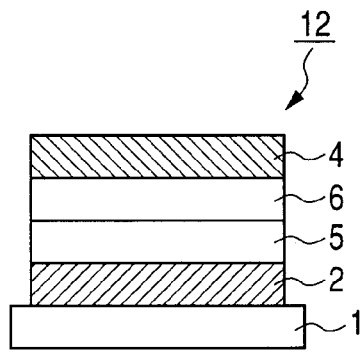

In the organic light emitting device 12 illustrated in FIG. 1B, the anode 2, the hole transport layer 5, the electron transport layer 6 and the cathode 4 are provided in this order over the substrate 1. The organic light emitting device 12 is useful in the case where a light emitting compound provided with hole transportability and/or electron transportability is used in combination with an organic compound provided with only electron transportability or only hole transportability. In the organic light emitting device 12, the hole transport layer 5 or the electron transport layer 6 also functions as a light transmitting layer.

Figure 1C:
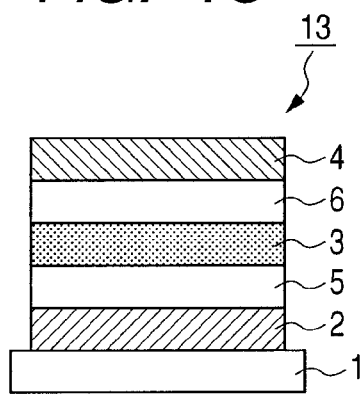

In the organic light emitting device 13 illustrated in FIG. 1C, the light emitting layer 3 is inserted between the hole transport layer 5 and the electron transport layer 6 in the organic light transmitting device illustrated in FIG. 1B. The organic light emitting device 13 is a device in which the function of carrier transport is separated from the function of light emission. Organic compounds having each hole transportability, electron transportability and light emitting ability can be suitably used in combination. Therefore, the degree of freedom in selecting materials can be greatly increased, and various organic compounds having a different light emission wavelength can be used, and thus a versatility of light emission hue can be achieved. Further, it is also possible to improve the light emitting efficiency of the organic light emitting device 13 by efficiently trapping a carrier or an exciton in the light emitting layer 3.

Figure 1D:
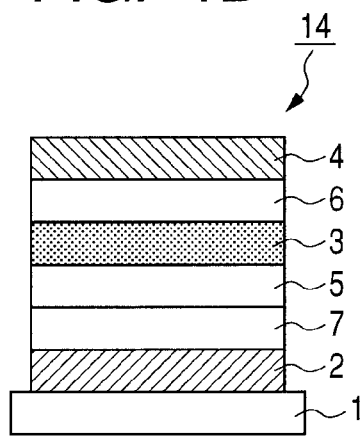

In the organic light emitting device 14 illustrated in FIG. 1D, the hole injection layer 7 is provided between the anode 2 and the hole transport layer 5 in the organic light emitting device 13 in FIG. 1C. The organic light emitting device 14 is efficient in reduction in voltage applied thereto, because the adhesion between the anode 2 and the hole transport layer 5 is increased or the injectability of holes is improved by providing the hole injection layer 7 between the anode 2 and the hole transport layer 5.

Figure 1E:
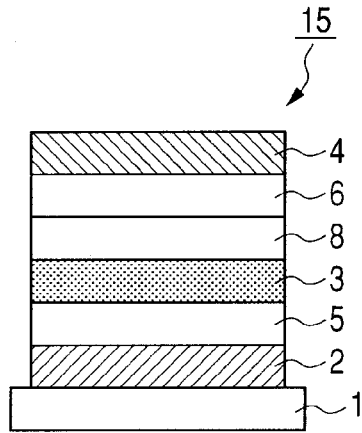

The organic light emitting device 15 illustrated in FIG. 1E, a layer (the hole/exciton blocking layer 8), which blocks holes or excitons from passing through the side of cathode 4, is inserted between the light emitting layer 3 and the electron transport layer 6 in the organic light emitting device 13 in FIG. 10. The light emitting efficiency of the organic light emitting device 15 can be increased by using an organic compound having very high ionization potential as a constituent material of the hole/exciton blocking layer 8.

Note that absolutely, the organic light emitting devices illustrated in FIGS. 1A to 1E each have a quite basic configuration, and the configuration of the organic light emitting device of the present invention is not limited thereto. The organic light emitting device of the present invention may have a variety of layer configurations, for example, a layer configuration in which an insulating layer, an adhesive layer or an interference layer is provided at the interface between an electrode and the organic compound layer; and a layer configuration in which the hole transport layer is formed of two layers having a different ionization potential.

In the organic light emitting device of the present invention, at least one diindenopicene compound of the present invention is contained in the organic compound layer. Specifically, the diindenopicene compound of the present invention is contained in any of the light emitting layer 3, the hole transport layer 5, the electron transport layer 6, the hole injection layer 7 and the hole/exciton blocking layer 8 illustrated in FIGS. 1A to 1E. Preferably, the diindenopicene compound is contained in a layer having a light transmitting ability. More preferably, the diindenopicene compound is contained in the light emitting layer 3. When the diindenopicene compound of the present invention is used as a constituent material particularly for the light emitting layer 3, the resulting organic light emitting device can improve its light emitting efficiency and show a blue light emission hue of remarkably excellent color purity. When the diindenopicene compound of the present invention is contained in the light emitting layer 3, the light emitting layer 3 may be a layer constituted only of the diindenopicene compound of the present invention, or may be a layer constituted of a dopant (guest) and a host.

When the light emitting layer 3 is constituted with a carrier-transportable host and a guest, the main process leading to light emission includes the following processes:
1. Transport of electrons/holes in light emitting layer
2. Generation of exciton of host
3. Transmission of host-intermolecular excitation energy
4. Transfer of excitation energy from host to guest Desired energy transfer and light emission in the respective processes take place in competition with deactivation processes.

To increase the light emitting efficiency of an organic light emitting device, it is needless to say that a light-emission center material itself should have a high light emission quantum yield. However, how efficiently the energy transfer can be caused between hosts or between a host and a guest is also an important point. In addition, the cause of deterioration in light emitting efficiency caused by application of an electric current is still unknown; however, it is assumed that the deterioration in light emitting efficiency relates to at least a light-emission center material itself or a change in the environment surrounding a light emitting material caused by peripheral molecules of the light-emission center material. For example, it can be considered that deterioration of light emission is caused by deterioration in a thin-film shape of a light emitting layer. The deterioration in a thin-film shape is considered attributable to crystallization of an organic thin film caused by a temperature employed in the driving environment, and heat generation at the time of driving the device. This crystallization is considered derived from the low glass transition temperature of a material used in an organic light emitting device, and thus it is desired for an organic light emitting material to have a high glass transition temperature. Since the diindenopicene compound of the present invention has a high glass transition temperature, the resulting organic light emitting device is expected to have high durability.

An organic light emitting device can improve its light emitting efficiency and show a blue light emission hue of remarkably excellent color purity by using diindenopicene compound of the present invention, particularly, as a host or guest of the light emitting layer.

When the light emitting layer is constituted with a host and a guest, the diindenopicene compound of the present invention is desirably used as the host or guest. Note that in the present invention, the term "guest" means, mainly, a compound which emits light responsive to a recombination of holes and electrons in light emitting areas of the organic light emitting device and which is contained in the light emitting layer 3 together with another compound (host) forming the light emitting areas.

Particularly when the diindenopicene compound of the present invention is used as a guest of the light emitting layer 3, it exhibits excellent effect. That is, it is possible to obtain emission of light having a light emission peak of 420 nm to 460 nm, showing a blue light emission hue of remarkably excellent color purity and having high luminance even with application of low current voltage.

When the diindenopicene compound of the present invention is used as a guest, the amount of diindenopicene compound relative to the total amount of the light emitting layer 3 is preferably 0.01% by weight to 80% by weight, more preferably 0.1% by weight to 30% by weight, and particularly preferably 0.1% by weight to 15% by weight. Note that the guest may be uniformly present in the entire layer containing a host as the main constituent, may be present with a certain concentration gradient, and may be partially contained in certain areas in the layer, without being present in other areas in the layer.

In addition, when the diindenopicene compound of the present invention is used as a guest, the light emitting layer preferably contains a host having an energy gap (a value calculated from optical absorbing edges in a measurement using UV) greater than that of the guest. With this configuration, it is possible to control the transfer of energy from the guest to host and to increase the light emitting efficiency by allowing only the guest to emit light.

Meanwhile, when the diindenopicene compound of the present invention is used as a host, as a corresponding guest, a light emitting material showing blue color and green color light emission is preferably used. When the benzofluoranthene compound of the present invention is used as a host, the amount of the diindenopicene compound relative to the total amount of the light emitting layer 3 is preferably 50% by weight to 99.9% by weight.

The diindenopicene compound of the present invention may be incorporated only into the light emitting layer 3, but may be incorporated into other layers than the light emitting layer (e.g., the hole injection layer 7, the hole transport layer 5, an electron injection layer, the electron transport layer 6, and an electron barrier layer).

The diindenopicene compound of the present invention is useful particularly as a constituent material of the light emitting layer 3, the electron transport layer 6 or the hole transport layer 5, and a layer formed using diindenopicene compound by vacuum vapor deposition or a solution coating method hardly causes crystallization and is excellent in stability with time.

The organic light emitting device of the present invention is a device in which the diindenopicene compound of the present invention is used particularly as a constituent material of the light emitting layer 3. Further, in the organic light emitting device of the present invention, a low-molecular weight- and polymer-based hole transport compound, a light emitting compound or an electron transport compound that have been known may be used as required, beside the diindenopicene compound of the present invention.

The following are examples of these compounds.

The hole injection/transport material preferably have excellent mobility facilitating injection of holes from the anode 2 and transporting the holes injected to the light emitting layer 3. Examples of the low-molecular weight material having hole injection/transport properties include triarylamine derivatives, phenylenediamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, and porphyrin derivatives. Examples of the polymer-based materials having hole injection/transport properties include poly(vinylcarbazole), poly(silylene), poly(thiophene), and other electrically conductive polymer.

Examples of the light emitting materials for use as a constituent material of the organic light emitting device of the present invention other than the diindenopicene compound of the present invention include condensed aromatic compounds (e.g., naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene); quinacridone derivatives, acridone derivatives, coumarine derivatives, pyran derivatives, nile red, pyrazine derivatives, benzimidazole derivatives, benzothiazole derivatives, benzoxazole derivatives, stilbene derivatives, organometallic complexes (e.g., organoaluminum complexes such as tris(8-quinolinolato)aluminum, and organoberyllium complex), and polymer derivatives such as poly(phenylenevinylene) derivatives, poly(fluorene) derivatives, poly(phenylene) derivatives, poly(thienylenevinylene) derivatives and poly(acetylene) derivatives.

The electron injection/transport materials may be arbitrarily selected from materials having functions to facilitate injection of electrons from the cathode 4 and to transport the electrons injected to the light emitting layer 3, in consideration of the balance with the carrier mobility of the hole transport material and the like. Examples of the material having electron injection/transport properties include oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes.

The constituent material for the anode 2 preferably has a work function as great as possible. Examples of the usable materials include elemental metals such as gold, platinum, silver, copper, nickel, palladium, cobalt, selenium, vanadium, and tungsten or alloys formed by combining two or more of them; and metal oxides such as tin oxide, zinc oxide, indium oxide, indium tin oxide (ITO), and indium zinc oxide. Further, conductive polymers such as polyaniline, polypyrrole, polythiophene, and poly(phenylene sulfide) can also be used. These electrode materials may be used alone or in combination. The anode 2 may be of either a single-layer configuration or a multi-layer configuration.

Meanwhile, the constituent material for the cathode 4 preferably has a work function as small as possible. Examples of the material include elemental metals such as lithium, sodium, potassium, calcium, magnesium, aluminum, indium, ruthenium, titanium, manganese, yttrium, silver, lead, tin, and chromium. Two or more of these metals may also be combined with each other to form alloys. For example, alloys such as lithium-indium, sodium-potassium, magnesium-silver, aluminum-lithium, aluminum-magnesium, and magnesium-indium can be used. Further, metal oxides such as indium tin oxide (ITO) can also be used. These electrode materials may be used alone or in combination. Moreover, the cathode 4 may be of either a single-layer configuration or a multi-layer configuration.

The substrate for use in the organic light emitting device of the present invention is not particularly limited. Examples thereof include opaque substrates (e.g., a metal substrate, and a ceramic substrate); and transparent substrates (e.g., glass, quartz, and plastic sheet). In addition, a color filter film, a fluorescent color-convertible filter film, or a dielectric reflection film may also be used to control the light emission.

Note that a protective layer or a sealing layer may also be provided to the device produced for the purpose of preventing contact with oxygen and moisture. Examples of the protective layer include inorganic material films (e.g., diamond thin film, metal oxide, and metal nitride), polymer films (e.g., fluororesin, polyparaxylene, polyethylene, silicone resin, and polystyrene resin); and photocurable resins. Further, it is also possible to package the device itself by a suitable sealing resin with covering it with glass, a gas-impermeable film, metal etc.

It is also possible to produce the organic light emitting device of the present invention in which a thin film transistor (TFT) is provided on the substrate to be connected thereto.

The light extraction direction of the device may be any of a bottom emission configuration (configuration of extracting light from the substrate side) and a top emission configuration (configuration of extracting light from the side opposite to the substrate).

The organic compound layer constituting the organic light emitting device of the present invention is formed by the method described below. In general, a thin film is formed by vacuum vapor deposition, ionization vapor deposition, sputtering, plasma or a known coating method (e.g., spin-coating, dip-coating, cast-coating, LB method, and inkjet method) in which an organic compound is dissolved in an appropriate solvent. Particularly when a film is formed by a coating method, it is also possible to form the film using an appropriate binder resin in combination.

The binder resin may be selected from a variety of binder resins. Examples thereof include, but are not limited to, polyvinyl carbazole resins, polycarbonate resins, polyester resins, polyarylate resins, polystyrene resins, ABS resins, polybutadiene resins, polyurethane resins, acrylic resins, methacrylic resins, butyral resins, polyvinyl acetal resins, polyamide resins, polyimide resins, polyethylene resins, polyether sulfone resins, diallyl phthalate resins, phenol resins, epoxy resins, silicone resins, polysulfone resins, and urea resins.

These resins may be used alone or in combination in the form of a mixture. Further, known additives, such as a plasticizer, an antioxidant, an ultraviolet ray absorber, may be used in combination, as required.

In the organic light emitting device of the present invention, the diindenopicene compound of the present invention is formed between the anode 2 and the cathode 4 by vacuum vapor deposition, a solution-coating method, etc. The thickness of a layer containing the diindenopicene compound is less than 10 μm, preferably 0.5 μm or less, and more preferably 0.01 μm to 0.5 μm.

EXAMPLES

Hereinafter, the present invention will be further described in detail by Examples; however, the present invention shall not be construed as being limited to these disclosed Examples.

Example 1

Synthesis Method of Exemplary Compound A-1

Exemplary Compound A-1 was synthesized according to the synthesis scheme described below.

Formula 18

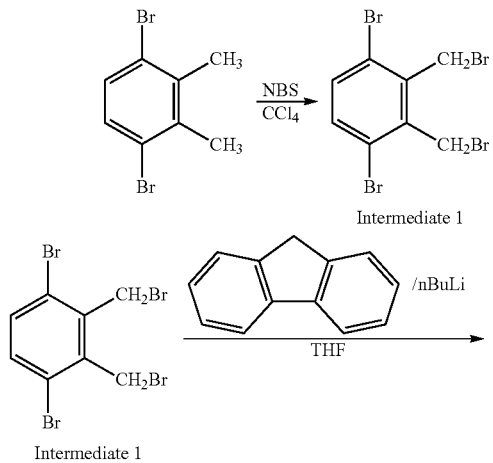

Intermediate 1

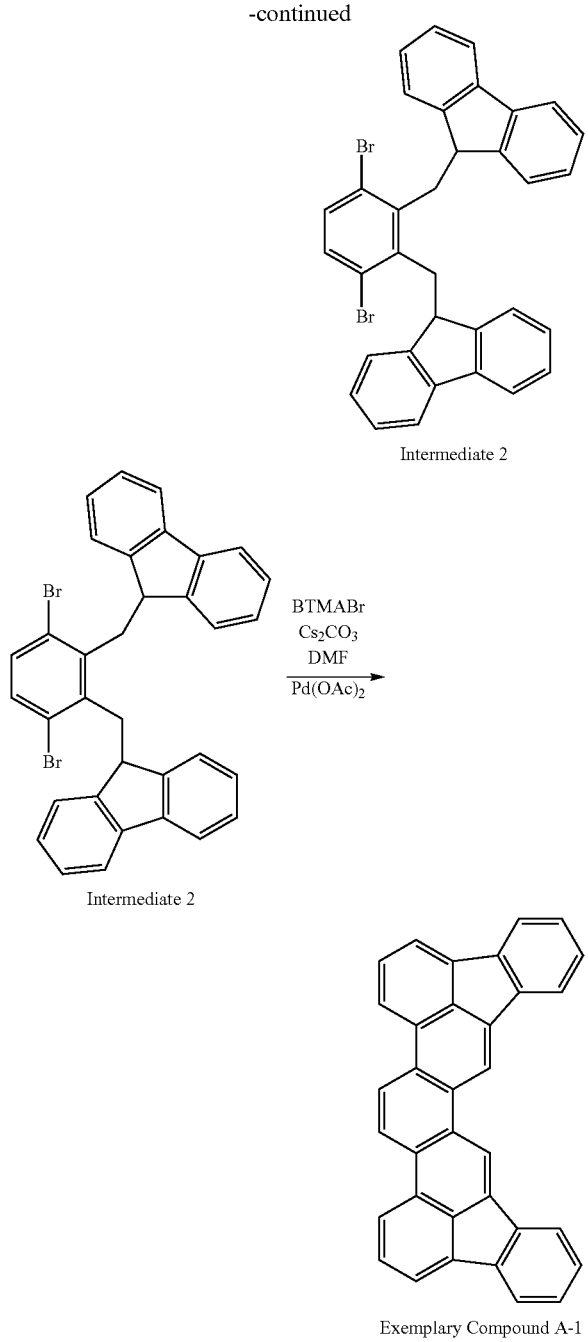

Intermediate 2

Intermediate 2

Exemplary Compound A-1

(1) Synthesis of Intermediate 1

The following reagents and solvent were placed into a reaction vessel.
1,4-dibromo-2,3-dimethylbenzene: 5.00 g (18.94 mmol)
N-bromosuccinimide (NBS): 7.41 g (41.63 mmol)
Anhydrous carbon tetrachloride: 100 ml Next, the mixture was stirred to dissolve the solid matters, and then the following reagent was placed into the reaction vessel.
Benzoyl peroxide (BPO): 30 mg (0.12 mmol)

Next, the reaction solution was stirred for 5 hours while being heated under reflux. Next, after the reaction solution was left standing to cool, insoluble matters were filtered out, and the solvent contained in the filtrate was distilled away under reduced pressure to thereby obtain a crude product.

Next, the crude product was purified by a silica gel column chromatography (developing solvent: toluene), thereby obtaining 2.98 g (yield: 37%) of Intermediate 1.

(2) Synthesis of Intermediate 2

The following reagent and solvent were placed into a reaction vessel.
9H-fluorene: 1.49 g (8.96 mmol)
Anhydrous tetrahydrofuran (THF): 50 ml Next, the mixture was cooled to −78° C., and then the following reagent was added dropwise into the mixture while the mixture being stirred at this temperature (−78° C.).
n-butyllithium (d=0.68, 1.6M): 5 ml (7.72 mmol)

Next, the temperature of the reaction solution was increased to 0° C. to thereby obtain a reddish brown reaction mixture. Next, the following reagent and solvent were mixed with the reaction mixture to prepare a THF solution.
Intermediate 1: 1.26 g (2.99 mmol)
Anhydrous tetrahydrofuran (THF): 10 ml Next the THF solution was added dropwise into the same reaction vessel. Then, the temperature of the reaction mixture was increased to room temperature, and then the reaction mixture was stirred for 2 hours while maintaining this temperature (room temperature). Next, ice chilled water was added to the reaction solution, and the reaction solution was separated into an organic layer and an aqueous layer by solvent extraction. Next, using toluene, solvent extraction was repeated three times for the aqueous layer to obtain an organic layer, and the thus obtained organic layer was mixed with the previously obtained organic layer. Next, the mixed organic layer was dried over magnesium sulfate, and then the solvent therein was distilled away under reduced pressure to thereby obtain a crude product. Next, the crude product was purified by a silica gel column chromatography (developing solvents: toluene:heptane=1:1), thereby obtaining 1.41 g (yield: 79%) of Intermediate 2.

(3) Synthesis of Exemplary Compound A-1

The following reagents and solvent were placed into a reaction vessel.
Intermediate 2: 300 mg (0.51 mmol)
Benzyl trimethyl ammonium bromide (BTMABr): 460 mg (2.00 mmol)
Cesium carbonate: 1.63 g (5.00 mmol)
Anhydrous dimethylformamide (DMF): 10 ml Next, after the inside of the reaction vessel was made to be nitrogen atmosphere, the reaction mixture was stirred to dissolve the insolubles, and then the following reagent was placed into the reaction vessel.
Palladium acetate: 226 mg (1.00 mmol)

Next, the reaction solution was stirred for 1 hour while being heated to 160° C. under reflux to thereby obtain a reddish brown reaction mixture. Next, toluene and water were added to the thus obtained reaction mixture, and an organic layer was separated from the reaction mixture by solvent extraction. Next, the organic layer was dried over magnesium sulfate, and then the solvent therein was distilled away under reduced pressure to thereby obtain a crude product. Next, the crude product was purified by a silica gel column chromatography (developing solvents: toluene:heptane=1:2), thereby obtaining 6 mg (yield: 11%) of Exemplary Compound A-1.

The resulting compound was measured for their physical properties, which were then evaluated.

Exemplary Compound A-1 was confirmed to have an $M^+$ of 426.5 and identified by matrix-assisted laser desorption/ionization time-of-flight mass spectrometry (MALDI-TOF-MS).

Example 2

Synthesis Method of Exemplary Compound D-11

Exemplary Compound D-11 was synthesized according to the following synthesis scheme.

Formula 19

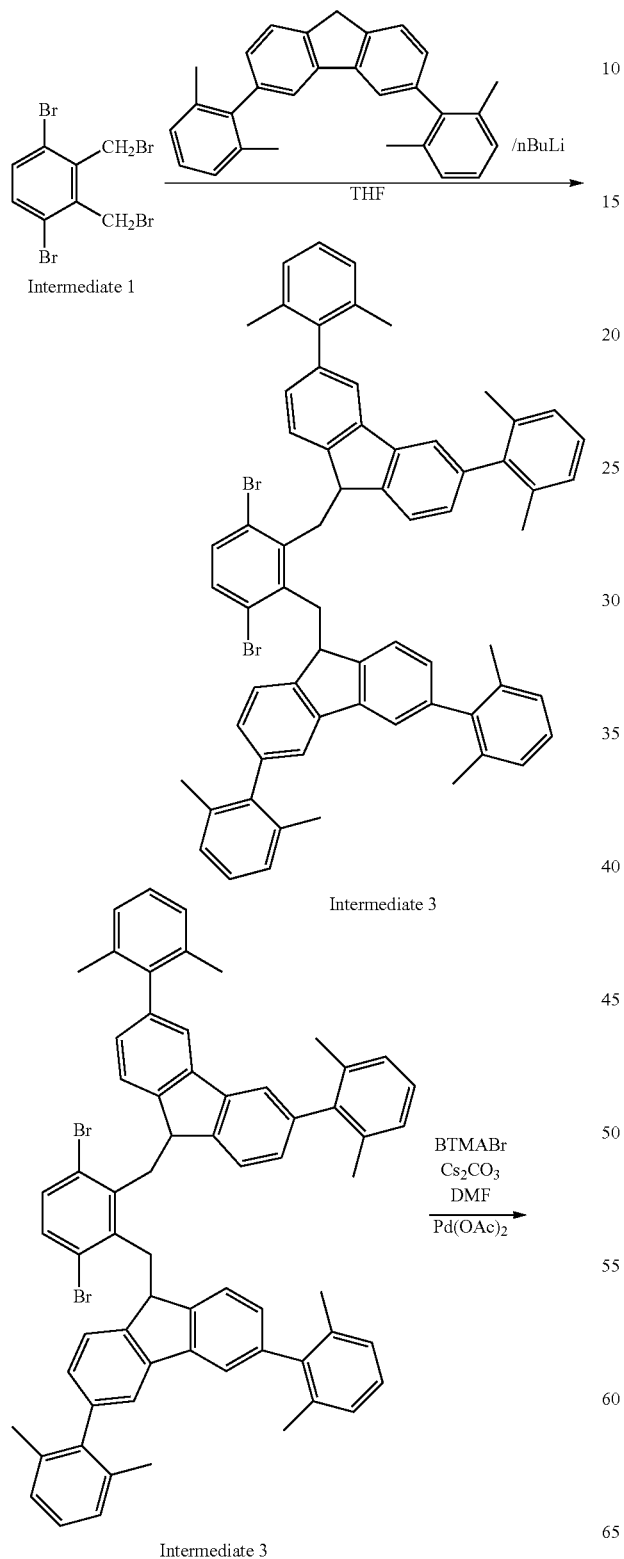

Intermediate 3

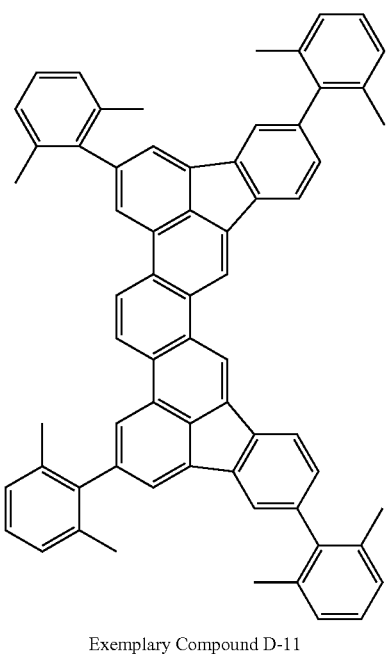

Exemplary Compound D-11

(1) Synthesis of Intermediate 3

The following reagent and solvent were placed into a reaction vessel.

3,6-bis(2,6-dimethylphenyl)-9H-fluorene: 690 mg (1.84 mmol)

Anhydrous tetrahydrofuran (THF): 50 ml

Next, the mixture was cooled to −78° C., and then the following reagent was added dropwise thereto while the mixture was stirred at this temperature (−78° C.).

n-butyllithium (d=0.68, 1.6M): 1.13 ml (1.80 mmol)

Next, the temperature of the reaction solution was increased to 0° C. to thereby obtain a reddish brown reaction mixture. Next, the following reagent and solvent were mixed with the reaction mixture to prepare a THF solution.

Intermediate 1: 278 g (0.66 mmol)

Anhydrous tetrahydrofuran (THF): 3 ml

Next the THF solution was added dropwise into the same reaction vessel. Then, the temperature of the reaction mixture was increased to room temperature, and then the reaction mixture was stirred for 2 hours while maintaining this temperature (room temperature). Next, ice chilled water was added to the reaction solution, and the reaction solution was separated into an organic layer and an aqueous layer by solvent extraction. Next, using toluene, solvent extraction was repeated three times for the aqueous layer to obtain an organic layer, and the thus obtained organic layer was mixed with the previously obtained organic layer. Next, the mixed organic layer was dried over magnesium sulfate, and then the solvent therein was distilled away under reduced pressure to thereby obtain a crude product. Next, the crude product was purified by a silica gel column chromatography (developing solvents: toluene:heptane=1:1), thereby obtaining 608 mg (yield: 91%) of Intermediate 3.

(2) Synthesis of Exemplary Compound D-11

The following reagents and solvent were placed into a reaction vessel.

Intermediate 3: 100 mg (0.10 mmol)

Benzyl trimethyl ammonium bromide (BTMABr): 226 mg (1.00 mmol)

Cesium carbonate: 326 mg (1.00 mmol)

Anhydrous dimethylformamide (DMF): 10 ml

Next, after the inside of the reaction vessel was made to be nitrogen atmosphere, the reaction mixture was stirred to dissolve the ingredients, and then the following reagent was placed into the reaction vessel.

Palladium acetate: 226 mg (1.00 mmol)

Next, the reaction solution was stirred for 1 hour while being heated to 160° C. under reflux to thereby obtain a reddish brown reaction mixture. Next, toluene and water were added to the thus obtained reaction mixture, and an organic layer was separated from the reaction mixture by solvent extraction. Next, the organic layer was dried over magnesium sulfate, and then the solvent therein was distilled away under reduced pressure to thereby obtain a crude product. Next, the crude product was purified by a silica gel column chromatography (developing solvents: toluene:heptane=1:2), thereby obtaining 18 mg (yield: 21%) of Exemplary Compound D-11.

The resulting compound was measured for their physical properties, which were then evaluated.

Exemplary Compound D-11 was confirmed to have an $M^+$ of 843.1 and identified by matrix-assisted laser desorption/ionization time-of-flight mass spectrometry (MALDI-TOF-MS).

The structure of Exemplary Compound D-11 was confirmed by NMR measurement. The following describes the attribution of peaks.

$^1$H-NMR (CDCl$_3$, 400 MHz) σ (ppm): 9.55 (s, 2H), 8.91 (s, 2H), 8.43 (s, 2H), 8.36 (d, 2H), 7.83 (s, 2H), 7.75 (s, 2H), 7.35-7.16 (m, 14H), 2.20 (s, 12H), 2.18 (s, 12H)

Figure 2:
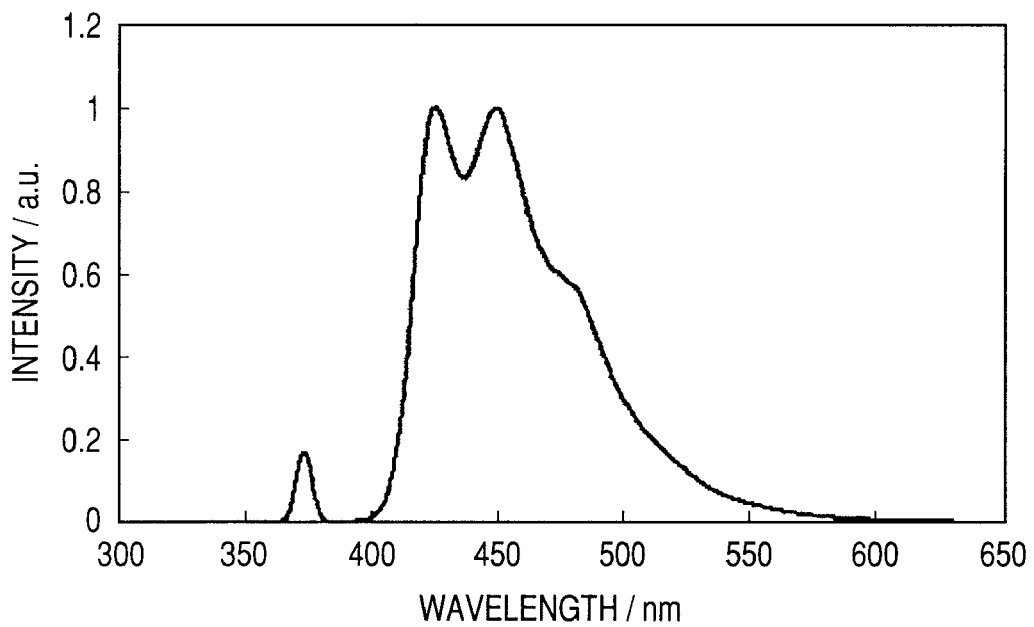
FIG. 2 is a graph illustrating a PL spectrum of a toluene solution ($1.0 \times 10^{-5}$ mol/L) of Exemplary Compound D-11.

Further, a toluene-diluted solution ($1.0 \times 10^{-5}$ mol/L) of Exemplary Compound D-11 was prepared, and then the light emission spectrum of the solution was measured by a spectrofluoro-photometer (F4500, manufactured by Hitachi Ltd.). As a result, a light emission spectrum illustrated in FIG. 2 was obtained, and it was found that the solution exhibits extremely good blue light emission. Also, from the result of FIG. 2, the maximum light emission intensity of the solution in the light emission spectrum was found to be 425 nm.

Meanwhile, an N,N-dimethylformamide solution ($1 \times 10^{-4}$ mol/L to $1 \times 10^{-6}$ mol/L) of Exemplary Compound D-11 was prepared, and the reduction potential of the solution was measured by a cyclic voltammetry method under the following conditions.

Support electrolytic substance: 0.1 mol/L of tetrabutyl ammonium perchlorate

Temperature: 25° C.

Reference electrode: Ag/AgNO$_3$

Counter electrode: platinum electrode

Working electrode: glassic carbon

The result of the measurement showed that the reduction potential was −2.00 V, and the lowest unoccupied molecular orbital (LUMO) was established to be deeper (the electron affinity was large).

Comparative Example 1

Synthesis Method of Comparative Compound 1

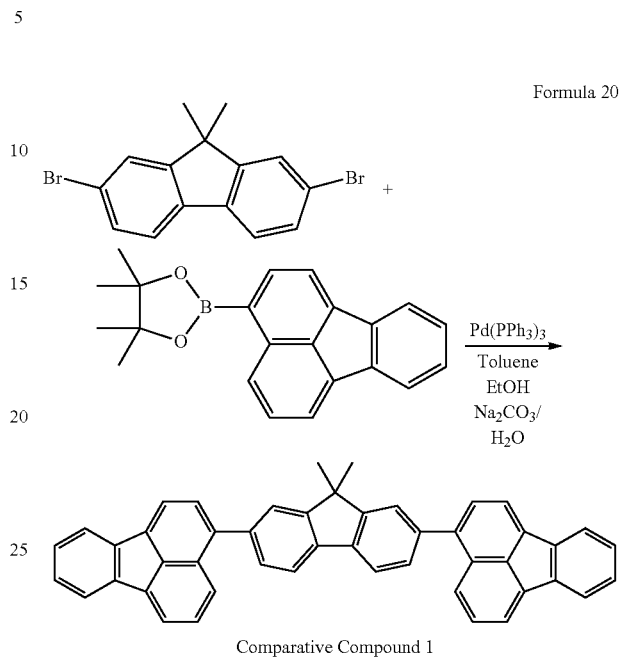

Comparative Compound 1

After the inside of the reaction vessel was made to be nitrogen atmosphere, the following reagents and solvents were placed into the reaction vessel.

2,7-dibromo-9,9-dimethyl-9H-fluorene: 0.25 g (0.73 mmol)

2-(fluoranthene-3-yl)-4,4,5,5-tetramethyl-[1,3,2] dioxaborolan: 0.48 g (1.45 mmol)

Toluene: 100 ml

Ethanol: 50 ml

Next, an aqueous solution prepared by mixing 0.95 g of cesium carbonate (2.90 mmol) with 15 ml of distilled water was added into the reaction solution, and then the reaction solution was heated to 50° C. and stirred at this temperature (50° C.) for 30 minutes.

Next, tetrakis(triphenylphosphine)palladium (0.17 g, 0.145 mmol) was added into the reaction solution, and the reaction solution was heated for 5 hours over a silicone oil bath heated at 90° C., while being stirred. Subsequently, after the reaction solution was cooled to room temperature, water, toluene and ethyl acetate were added thereto, and then an organic layer was collected by separating operation. Next, an aqueous layer obtained from the reaction solution was subjected to solvent extraction of the mixed solvent of toluene and ethyl acetate twice, and the collected organic layer was added to the previously collected organic layer. The collected organic layers were washed with saturated saline and then dried over sodium sulfate. Next, the solvents therein were distilled away under reduced pressure to thereby obtain a crude product. Next, the crude product was purified by a silica gel column chromatography (developing solvents: toluene: heptane=1:3). Crystals obtained by the production was subjected to vacuum drying at 120° C. and then to sublimation purification, thereby obtaining Comparative Compound 1 (0.3 g).

This compound was confirmed to have an M⁺ of 594.7 by matrix-assisted laser desorption/ionization time-of-flight mass spectrometry (MALDI-TOF-MS).

Figure 3:
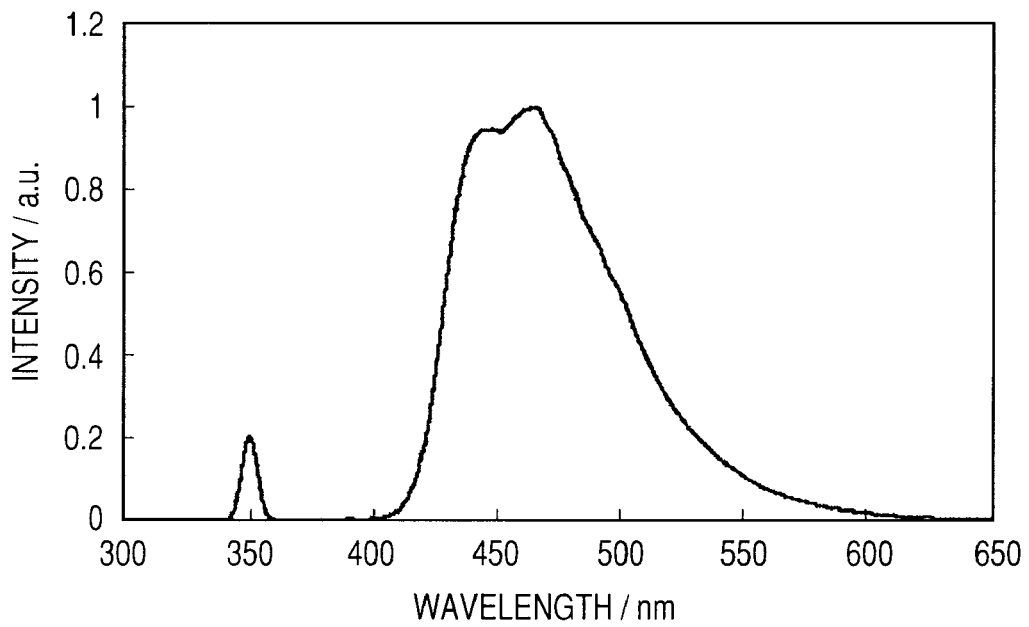
FIG. 3 is a graph illustrating a PL spectrum of a toluene solution ($1.0 \times 10^{-5}$ mol/L) of Comparative Compound 1.

Further, a toluene-diluted solution of the compound was prepared, and the light emission spectrum of the compound was measured by a spectrofluoro-photometer (F4500, manufactured by Hitachi Ltd.). As a result, as the light emission spectrum illustrated in FIG. 3, it was found that wavelengths of light emission peaks of the compound were present on the longer sides as compared to Example 2.

The reduction potential of the compound was measured by a cyclic voltammetry method and found to be −2.08 V and to have a lowest unoccupied molecular orbital (LUMO) (electron affinity) equivalent to the lowest unoccupied molecular orbital of Example 2.

Example 3

An organic luminescent device as illustrated in FIG. 1D was produced. First, Compound 1 to Compound 4, which are a material constituting the organic light emitting device, were synthesized in the following methods.

(Synthesis Method of Compound 1)

Formula 21

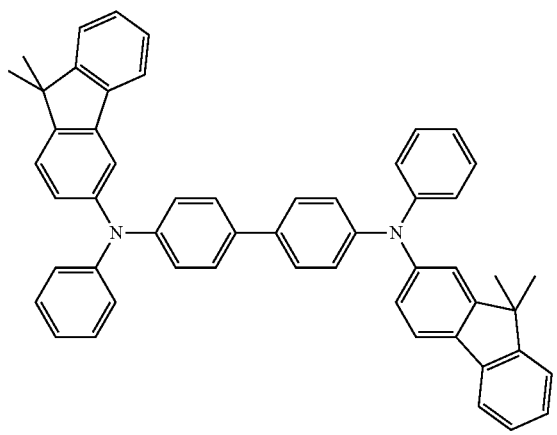

Compound 1

The following reagents and solvent were placed into a 100 ml eggplant flask.

N,N'-diphenylbenzidine: 4.88 g (14.5 mmol)

2-iodo-9,9-dimethylfluorene: 6.40 g (20 mmol)

Potassium carbonate: 4.00 g

Copper powder: 3.0 g

Orthodichlorobenzene: 30 ml

Next, a condenser was attached to the eggplant flask, and then the reaction solution was stirred for 20 hours under reflux. Next, the reaction solution was cooled and then filtered to remove solid impurities. Next, the filtrate obtained by the filtration above was condensed under reduced pressure, and orthodichlorobenzene serving as a solvent was distilled away. Next, methanol was added to the reaction solution to precipitate crude crystals, and the crude crystals were taken out from the filter. Next, the crude crystals were purified by a silica gel column chromatography (developing solvent: toluene/hexane mixed solution), thereby obtaining white color crystals of Compound 1 (7.32 g) (yield: 70%).

(Synthesis Method of Compound 2)

Formula 22

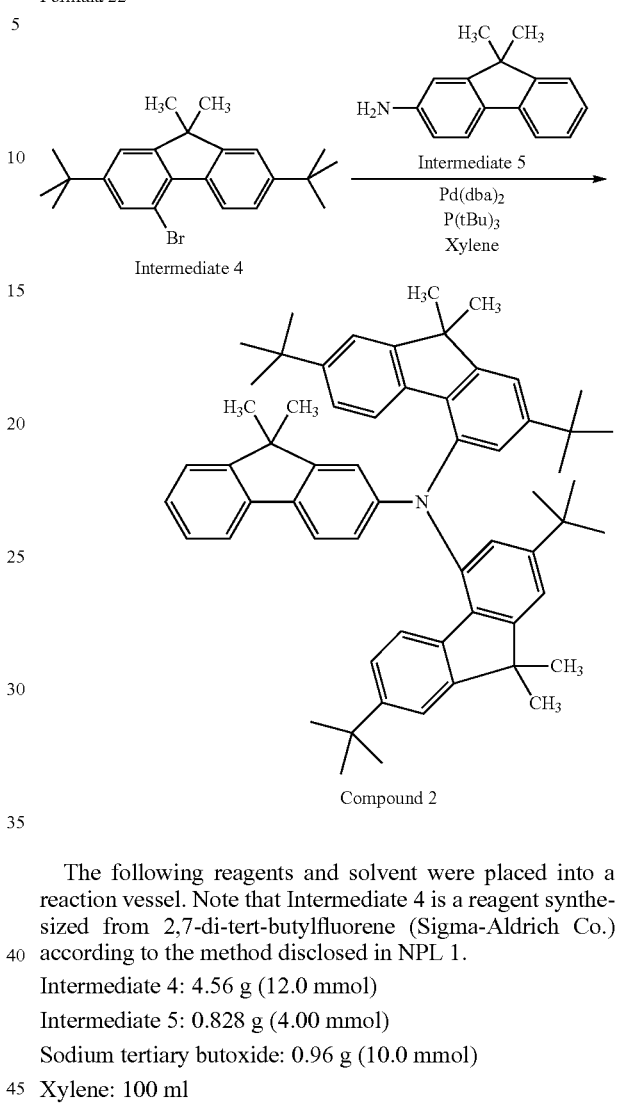

Compound 2

The following reagents and solvent were placed into a reaction vessel. Note that Intermediate 4 is a reagent synthesized from 2,7-di-tert-butylfluorene (Sigma-Aldrich Co.) according to the method disclosed in NPL 1.

Intermediate 4: 4.56 g (12.0 mmol)

Intermediate 5: 0.828 g (4.00 mmol)

Sodium tertiary butoxide: 0.96 g (10.0 mmol)

Xylene: 100 ml

Next, the inside of the reaction system was made to be nitrogen atmosphere, and the reaction solution was stirred at room temperature. Next, tri-tertiary-butylphosphine 34.4 mg (0.17 mmol) was added to the reaction solution. Next, palladium-dibenzylidene acetone 48.9 mg (0.085 mmol) was added to the reaction solution.

Next, the temperature of the reaction solution was increased to 125° C. and then the reaction solution was stirred for 3 hours at this temperature (125° C.). After completion of the reaction, an organic layer was extracted using toluene, dried over anhydrous sodium sulfate, and then the solvent was distilled away under reduced pressure to thereby obtain a crude product. Next, the crude product was purified by a silica gel column chromatography (developing solvent: heptane-toluene mixed solvent), thereby obtaining white color crystals of Compound 2 (2.53 g) (yield: 78.0%).

The compound was confirmed to have an M⁺ of 817.5 by mass spectrometry. Further, the compound was confirmed to have a melting point of 267° C. and a glass transition temperature of 143° C. by differential scanning calorimetry (DSC).

(Synthesis Method of Compound 3)

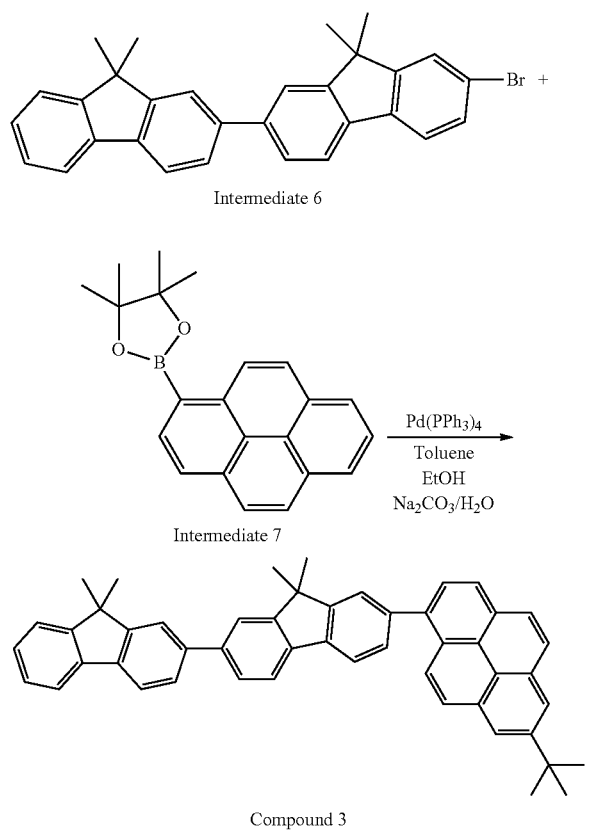

(Synthesis of Compound 4)

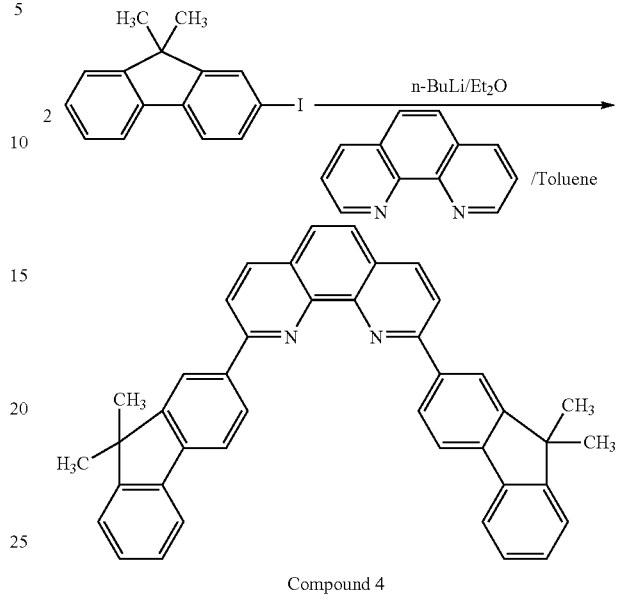

The following reagents and solvent were placed into a 100 ml flask.

Intermediate 6: 698 mg (1.5 mmol)

Intermediate 7: 576 mg (1.5 mmol)

Toluene: 15 ml

Ethanol: 7.5 ml 2M sodium carbonate aqueous solution: 15 ml

Tetrakis(triphenylphosphine)palladium (0): 100 mg (0.09 mmol)

Next, the reaction solution was heated to 80° C. while passing a current of nitrogen gas through the flask and then stirred for 8 hours at this temperature (80° C.). After completion of the reaction, an organic layer was collected from the reaction solution by solvent extraction using toluene. Next, the collected organic layer washed with water and dried over magnesium sulfate. Next, the organic layer was condensed under reduced pressure to thereby obtain a crude product. Next, the resulting crude product was purified by a silica gel column chromatography (developing solvent: toluene) and then subjected to recrystallization with a toluene/ethanol mixed solvent. The resulting crystals were subjected to vacuum drying and then to sublimation purification, thereby obtaining Compound 3 (570 mg) (yield: 59.1%).

This compound was confirmed to have an M⁺ of 642.3 and identified by matrix-assisted laser desorption/ionization time-of-flight mass spectrometry (MALDI-TOF-MS).

The following reagent and solvent were placed into a 300 ml three-necked flask.

2-iodo-9,9-dimethylfluorene: 5.8 g (18.1 mmol)

Ethyl ether: 80 ml

Next, the inside of the reaction system was made to be nitrogen atmosphere, and then the reaction solution was cooled to −78° C. Next, n-butyllithium (15% hexane solution) (11.7 ml (18.1 mmol)) was added dropwise into the reaction solution while the reaction solution being stirred at this temperature (−78° C.). Next, the temperature of the reaction solution was increased to room temperature, and the reaction solution was stirred for 1 hour at this temperature (room temperature). Next, the reaction solution was cooled to −20° C., and then a toluene dispersion liquid prepared by mixing phenanthroline 0.81 g (4.51 mmol) with toluene (100 ml) was added dropwise into the reaction solution. Next, the temperature of the reaction solution was increased to room temperature, and the reaction solution was stirred for 12 hours at this temperature (room temperature). Next, after water was added to the reaction solution, an organic layer was extracted from the reaction solution using chloroform. Next, this organic layer was dried over anhydrous sodium sulfate, and then the solvent was distilled away under reduced pressure to thereby obtain a crude product. Next, the crude product was purified by an alumina column chromatography (developing solvent: hexane-chloroform mixed solvent), thereby obtaining white color crystals of Compound 9 (2.04 g) (yield: 80%).

(Production of Organic Light Emitting Device)

A film of indium tin oxide (ITO) was formed on a glass substrate (substrate 1) by sputtering to form an anode 2. At this time, the anode 2 was formed to have a film thickness of 120 nm. Next, the substrate having the anode 2 formed on its surface was subjected to ultrasonic cleaning sequentially with acetone, and isopropyl alcohol (IPA), and subsequently with pure water, and was dried. In addition, the substrate was subjected to UV/ozone washing. The resulting substrate was used as a transparent conductive support substrate.

Next, Compound 1 and chloroform were mixed to prepare a chloroform solution having a concentration of 0.1% by weight.

Next, the chloroform solution was added dropwise onto the anode 2, and spin-coated first at 500 rpm for 10 seconds and then at 1,000 rpm for 40 seconds to thereby form a film on the anode 2. Next, the substrate was dried in a vacuum oven at 80° C. for 10 minutes to completely remove the solvent in the thin film, thereby forming a hole injection layer 7. At this time, the hole injection layer 7 was formed to have a film thickness of 11 nm.

Next, Compound 2 was deposited on hole injection layer 7 by vacuum vapor deposition to form a hole transport layer 5. At this time, the hole transport layer 5 was formed to have a film thickness of 15 nm.

Next, Compound 3 serving as a host and Exemplary Compound D-11 serving as a light emitting dopant were co-deposited by vacuum vapor deposition so that the concentration of Exemplary Compound D-11 was 5% by weight to the total concentration of the resulting layer, thereby forming a light emitting layer 3. At this time, the light emitting layer 3 was formed to have a film thickness of 25 nm. Note that Compound 3 and Exemplary Compound D-11 were co-deposited from different boats.

Next, Compound 5 was deposited on the light emitting layer 3 by vacuum vapor deposition to form an electron transport layer 6. At this time, the electron transport layer 6 was formed, under the conditions: a film thickness: 25 nm; a degree of vacuum at the time of deposition: $1.0 \times 10^{-4}$ Pa; and a deposition rate: 0.1 nm/sec to 0.3 nm/sec.

Next, lithium fluoride (LiF) was deposited on the electron transport layer 6 by vacuum vapor deposition to form a first electron injection electrode, under the conditions: a film thickness of lithium fluoride: 0.5 nm; a degree of vacuum at the time of deposition: $1.0 \times 10^{-4}$ Pa; and a deposition rate: 0.01 nm/sec. Next, aluminum was deposited on the first electron injection electrode to form a second electron injection electrode, under the conditions: a film thickness of the second electron injection electrode: 100 nm; a degree of vacuum at the time of deposition: $1.0 \times 10^{-4}$ Pa; and a deposition rate: 0.5 nm/sec to 1.0 nm/sec. According to the procedure described above, an organic light emitting device was obtained.

When a direct current voltage of 5 V was applied to the thus obtained organic light emitting device provided with the ITO electrode (anode 2) serving as a positive electrode and the Al electrode (cathode 4) serving as a negative electrode, the current flowed into the device with a current density of 35 mA/cm$^2$, and light emission of blue color was observed with a luminance intensity of 1,500 cd/m$^2$. The chromaticity of the device was NTSC (X,Y)=(0.15, 0.16).

As having been described with reference to embodiments and Examples, according to the present invention, it is possible to provide an organic light emitting device which shows a blue light emission hue of remarkably excellent color purity with high-light emitting efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-229314, filed Oct. 1, 2009, which is hereby incorporated by reference herein in its entirety.

The invention claimed is:

1. A diindenopicene compound represented by general formula [1] described below:

Formula 1

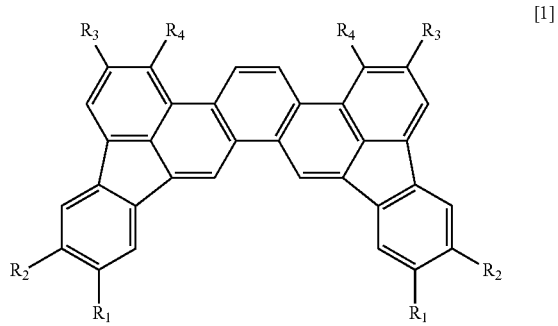

wherein $R_1$ to $R_4$ are each a hydrogen atom, an alkyl group, an unsubstituted phenyl group or a phenyl group substituted by an alkyl group, provided that a combination of substituents represented by $R_1$ to $R_4$ is any of the following (1) to (4):
(1) $R_1$, $R_2$, $R_3$ and $R_4$ are all hydrogen atoms;
(2) $R_1$ and $R_4$ are each an alkyl group, an unsubstituted phenyl group or a phenyl group substituted by an alkyl group, and $R_2$ and $R_3$ are each a hydrogen atom, wherein $R_1$ and $R_4$ are identical or different;
(3) $R_2$ and $R_3$ are each an alkyl group, an unsubstituted phenyl group or a phenyl group substituted by an alkyl group, and $R_1$ and $R_4$ are each a hydrogen atom, wherein $R_2$ and $R_3$ are identical or different;
(4) $R_1$ is an alkyl group, an unsubstituted phenyl group or a phenyl group substituted by an alkyl group, $R_2$ and $R_4$ are each a hydrogen atom, and $R_3$ is a hydrogen atom, an unsubstituted phenyl group or a phenyl group substituted by an alkyl group, wherein when both $R_1$ and $R_3$ are an unsubstituted phenyl group or a phenyl group substituted by an alkyl group, $R_1$ and $R_3$ are identical or different.

2. An organic light emitting device comprising:
an anode,
a cathode, and
an organic compound layer sandwiched between the anode and the cathode,
wherein at least one diindenopicene compound according to claim 1 is contained in the organic compound layer.

3. The organic light emitting device according to claim 2, wherein the diindenopicene compound is contained in a light emitting layer.

4. An apparatus comprising an organic light emitting device according to claim 2 or 3 and a substrate, wherein light emitted from the organic light emitting device travels outside the apparatus through the substrate side.

5. An apparatus comprising an organic light emitting device according to claim 2 or 3 and a substrate, wherein light emitted from the organic light emitting device travels outside the apparatus from the side opposite to the substrate.

6. An apparatus comprising an organic light emitting device according to claim 2 or 3 and a substrate, wherein the apparatus further comprises a color filter.

* * * * *